US012060581B2

(12) United States Patent
Polo et al.

(10) Patent No.: US 12,060,581 B2
(45) Date of Patent: Aug. 13, 2024

(54) METHODS AND CELLULAR STRUCTURES

(71) Applicant: Monash University, Clayton (AU)

(72) Inventors: Jose Polo, Clayton (AU); Xiaodong Liu, Clayton (AU); Jia Ping Tan, Clayton (AU)

(73) Assignee: MONASH UNIVERSITY, Clayton (AU)

( * ) Notice: Subject to any disclaimer, the term of this patent is extended or adjusted under 35 U.S.C. 154(b) by 14 days.

(21) Appl. No.: 17/534,592

(22) Filed: Nov. 24, 2021

(65) Prior Publication Data

US 2022/0259566 A1 Aug. 18, 2022

(30) Foreign Application Priority Data

| Nov. 24, 2020 | (AU) | ................................ | 2020904338 |
| Mar. 10, 2021 | (AU) | ................................ | 2021900685 |
| Sep. 3, 2021 | (AU) | ................................ | 2021902865 |
| Oct. 26, 2021 | (AU) | ................................ | 2021903427 |

(51) Int. Cl.
*C12N 5/074* (2010.01)

(52) U.S. Cl.
CPC ......... *C12N 5/0696* (2013.01); *C12N 5/0607* (2013.01); *C12N 2501/115* (2013.01); *C12N 2501/15* (2013.01); *C12N 2501/155* (2013.01); *C12N 2501/415* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/608* (2013.01); *C12N 2506/03* (2013.01); *C12N 2510/02* (2013.01)

(58) Field of Classification Search
None
See application file for complete search history.

(56) References Cited

U.S. PATENT DOCUMENTS

| 8,058,065 | B2 * | 11/2011 | Yamanaka | ............ | C12N 5/0696 435/373 |
| 2022/0162550 | A1 | 5/2022 | Polo et al. | | |

FOREIGN PATENT DOCUMENTS

| WO | WO 2009/101407 A2 | 8/2009 |
| WO | WO 2011/037270 A1 | 3/2011 |
| WO | WO 2011/055851 A1 | 5/2011 |
| WO | WO 2011/090221 A1 | 7/2011 |
| WO | WO 2011/091475 A1 | 8/2011 |
| WO | WO 2011/158967 A1 | 12/2011 |
| WO | WO 2012/036299 A1 | 3/2012 |
| WO | WO 2012/060473 A1 | 5/2012 |
| WO | WO 2013/176233 A1 | 11/2013 |
| WO | WO 2014/065435 A1 | 5/2014 |
| WO | WO 2014/171824 A1 | 10/2014 |
| WO | WO 2014/200114 A1 | 12/2014 |
| WO | WO 2015/056804 A1 | 4/2015 |
| WO | WO 2014/200030 A1 | 2/2017 |
| WO | WO 2017/219232 A1 | 12/2017 |
| WO | WO 2018/046929 A1 | 3/2018 |
| WO | WO 2018/175691 A1 | 9/2018 |
| WO | WO 2019/073055 A1 | 4/2019 |
| WO | WO 2021/067854 A1 | 4/2021 |

OTHER PUBLICATIONS

Blakeley et al., "Defining the three cell lineages of the human blastocyst by single-cell RNA-seq", Development, 2015, 142(20): 3613.
Boroviak, T. et al. "Single cell transcriptome analysis of human, marmoset and mouse embryos reveals common and divergent features of preimplantation development", Human Development, 2018, 145, 26 pages.
Butler, et al. "Integrating single-cell transcriptomic data across different conditions, technologies, and species", Nature Biotechnology, 2018, 36:411-420.
Chen et al., "Chemically defined conditions for human iPS cell derivation and culture", Nat Methods, 2011, 8(5): 424-429.
Deglincerti, A. et al. "Self-organization of the in vitro attached human embryo", Nature, 2016, 533:251-254.
Dobin, A. et al. "STAR: ultrafast universal RNA-seq aligner", Bioinformatics, 2013, 29: 15-21.
Durruthy-Durruthy et al., "Spatiotemporal Reconstruction of the Human Blastocyst by Single-Cell Gene-Expression Analysis Informs Induction of Naive Pluripotency", Dev Cell, 2016, 38: 100-115.
Fogarty et al., "Genome editing reveals a role for OCT4 in human embryogenesis", Nature, 2017, 550: 67-73.
Guo et al. "Naive Pluripotent Stem Cells Derived Directly from Isolated Cells of the Human Inner Cell Mass", Stem Cell Reports, 2016, 6:437-446.
Hafemeister C. & Satija, R. "Normalization and variance stabilization of single-cell RNA-seq data using regularized negative binomial regression", Genome Biology, 2019, 20-296, 15 pages.
Harrison et al., "Assembly of embryonic and extraembryonic stem cells to mimic embryogenesis in vitro", Science, 2017, 356(6334): eaal1810.
Huang et al. "Vireo: Bayesian demultiplexing of pooled single-cell RNA-seq data without genotype reference", Genome Biology, 2019, 20-273, 12 pages.
Hyun et al. "Toward Guidelines for Research on Human Embryo Models Formed from Stem Cells", Stem Cell Reports, 2020, 14:169-174.
Kime et al., "Induced 2C Expression and Implantation-Competent Blastocyst-like Cysts from Primed Pluripotent Stem Cells", Stem Cell Reports, 2019, 13: 485-498.

(Continued)

*Primary Examiner* — Kara D Johnson
*Assistant Examiner* — Maytee Marie Contes De Jesus
(74) *Attorney, Agent, or Firm* — COOLEY LLP; Matthew Pavao; Robert E. Powers

(57) ABSTRACT

The invention provides methods and compositions for producing a multi-layered cellular structure or blastocyst-like structure from a cell population of reprogrammed somatic cells.

26 Claims, 45 Drawing Sheets
(39 of 45 Drawing Sheet(s) Filed in Color)
Specification includes a Sequence Listing.

(56) References Cited

OTHER PUBLICATIONS

Kolde, R. & Vilo, J. Gosummaries: an R Package for Visual Functional Annotation of Experimental Data [version 1; peer review:2 approved], F1000Research, 2015, 4: 574, 23 pages.
Kovacic et al. "Developmental capacity of different morphological types of day 5 human morulae and blastocysts", Reproductive Biomedicine Online, 2004, 8(6): 687-694.
Kuijk, E. W. et al. "The roles of FGF and MAP kinase signaling in tlle segregation of the epiblast and hypoblast cell lineages in bovine and human embryos", Development, 2012, 139: 871-882.
Lam, A. Q. et al. "Rapid and Efficient Differentiation of Human Pluripotent Stem Cells into Intermediate Mesoderm That Forms Tubules Expressing Kidney Proximal Tubular Markers", J. Am. Soc. Nephrol., 2014, 25: 1211-1225.
Li et al., "Generation of Blastocyst-like Structures from Mouse Embryonic and Adult Cell Cultures", Cell, 2019, 179(3): 687-702.
Linneberg-Agerholm et al. "Naïve human pluripotent stem cells respond to Wnt, Nodal and LIF signalling to produce expandable naïve extra-embryonic endoderm", Development, 2019, 146, 15 pages.
Liu et al., "Modelling human blastocysts by reprogramming fibroblasts into iBlastoids", Nature, 2021, 591(7851), 627-632.
Liu X, et al., "Comprehensive characterization of distinct states of human naive pluripotency generated by reprogramming", Nat Methods, 2017, 14: 1055-1062.
Liu et al. An integrated chromatin accessibility and transcriptome landscape of human pre-implantation embryos, Nature Communications, 2019, 10:364, 11 pages.
Liu et al., "Reprogramming roadmap reveals route to human induced trophoblast stem cells", Nature, 2020, 586:101-107.
Niakan et al. "Analysis ofhumanembryosfromzygotetoblastocystrevealsdistinctgene expression patternsrelativetothemouse", Developmental Biology, 2013, 375:54-64.
Nichols & Smith., "Naive and Primed Pluripotent States", Cell Stem Cell, 2009, 4: 487-492.
Okae et al., "Derivation of Human Trophoblast Stem Cells", Cell Stem Cell, 2018, 22, 50-63.
Petropoulos et al., "Single-Cell RNA-Seq Reveals Lineage and X Chromosome Dynamics in Human Preimplantation Embryos", Cell, 2016, 165(4): 1012-1026.
Qin et al., "YAP Induces Human Naive Pluripotency", Cell Reports, 2016, 14: 2301-2312.
Rivron et al., "Blastocyst-like structures generated solely from stem cells", Nature, 2018, 557(7703): 106-111.
Roode, et al. "Human hypoblast formation is not dependent on FGF signalling", Developmental biology, 2012, 361:358-363.
Rossant et al. "New Insights into Early Human Development: Lessons for Stem Cell Derivation and Differentiation", Cell Stem Cell, 2017, 20:18-28.
Scialdone, A et al. "Computational assignment of cell-cycle stage from single-cell transcriptome data", Methods, 2015, 85:54-61.
Shahbazi et al., "Self-organization of the human embryo in the absence of maternal tissues", Nat Cell Biol, 2016, 18: 700-708.
Sozen et al., "Self-assembly of embryonic and two extra-embryonic stem cell types into gastrulating embryo-like structures", Nat Cell Biol, 2018, 20(8): 979-989.
Sozen et al., "Self-Organization of Mouse Stem Cells into an Extended Potential Blastoid", Dev Cell, 2019, 51(6): 698-712.
Stuart, T. et al. "Comprehensive Integration of Single-Cell Data", Cell 2019, 177, 1888-1902.e21.
Takahashi et al. "Induction of Pluripotent Stem Cells from Adult Human Fibroblasts by Defined Factors", Cell, 2007, 131: 861-872.
Takahashi et al. "Induction of pluripotency in human somatic cells via a transient state resembling primitive streak-like mesendoderm", Nature Communications, 2014, 5, 3678, 9 pages.
Tan et al., "Generation of human blastocyst-like structures by somatic cell reprogramming", protocol exchange, 2021, DOI:10.21203/rs.3.pex-1347/v1.
The International Stem Cell Initiative, "Characterization of human embryonic stem cell lines by the International Stem Cell Initiative", Nature Biotechnology, 2007, 25(7): 803-816.
Thermo Fisher Scientific, 'Culturing Pluripotent Stem Cells (PSCs) in Essential 8TM Medium', [retrieved from internet on Jan. 13, 2022]. <URL:https://tools.thermofisher.com/content/sfs/manuals/feeder_free_PSCs_in_essential8_medium.pdf> published on Sep. 27, 2015 as per Wayback Machine.
Thomson et al., "Embryonic Stem Cell Lines Derived from Human Blastocysts", Science, 1998, 282(5391): 1145-1147.
Tyser et al. "A spatially resolved single cell atlas of human gastrulation", Nature, 2020, 32 pages.
O'Rahilly et al. "Developmental stages in human embryos: revised and new measurements", Cells Tissues Organs, 2010, 192: 73-84.
Wamaitha, S. E. et al. "IGF1-mediated human embryonic stem cell self-renewal recapitulates the embryonic niche", Nature Communications, 2020, 11:764.
WARNOCK—Report of the Committee of Inquiry into Human Fertilisation and Embryology, Ir. Nurs. News, 1985, 5, 7-8.
Wu et al., "Comparative Analysis and Refinement of Human PSC-Derived Kidney Organoid Differentiation with Single-Cell Transcriptomics", Cell Stem Cell, 2018, 23: 869-881.
Xiang et al., "A developmental landscape of 3D-cultured human pre-gastrulation embryos", Nature, 2020, 577(7791): 537-542.
Yamaguchi "The Kyoto Collection of Human Embryos and Fetuses: History and Recent Advancementsin Modern Methods", Cells Tissues Organs, 2018, 205:314-319.
Zhang et al., "Implantation initiation of self-assembled embryo-like structures generated using three types of mouse blastocyst-derived stem cells", Nat Commun, 2019, 10(1): 496.
"The Istanbul consensus workshop on embryo assessment: proceedings of an expert meeting", Human Reproduction, 2011, 26: 1270-1283.

\* cited by examiner

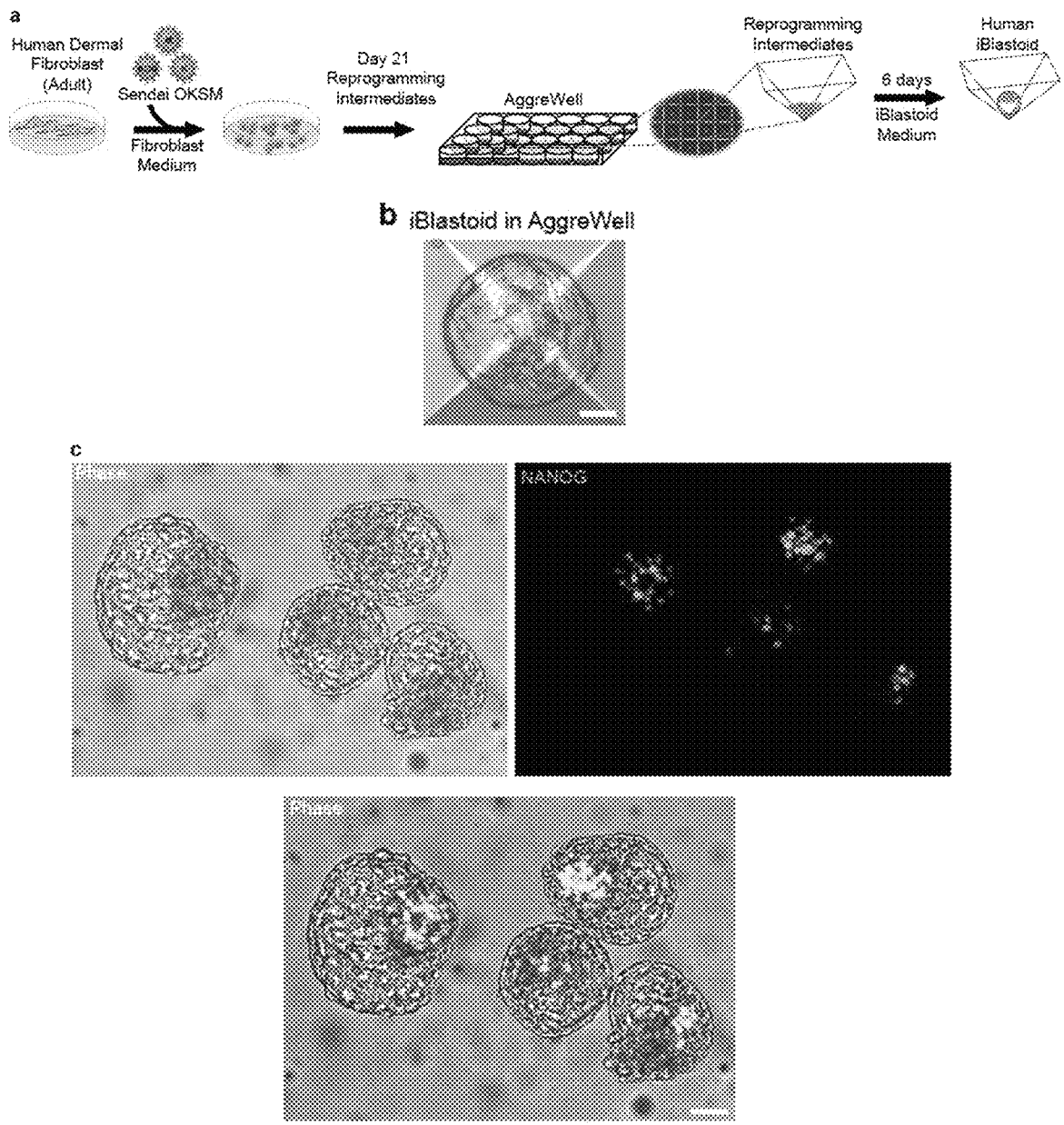

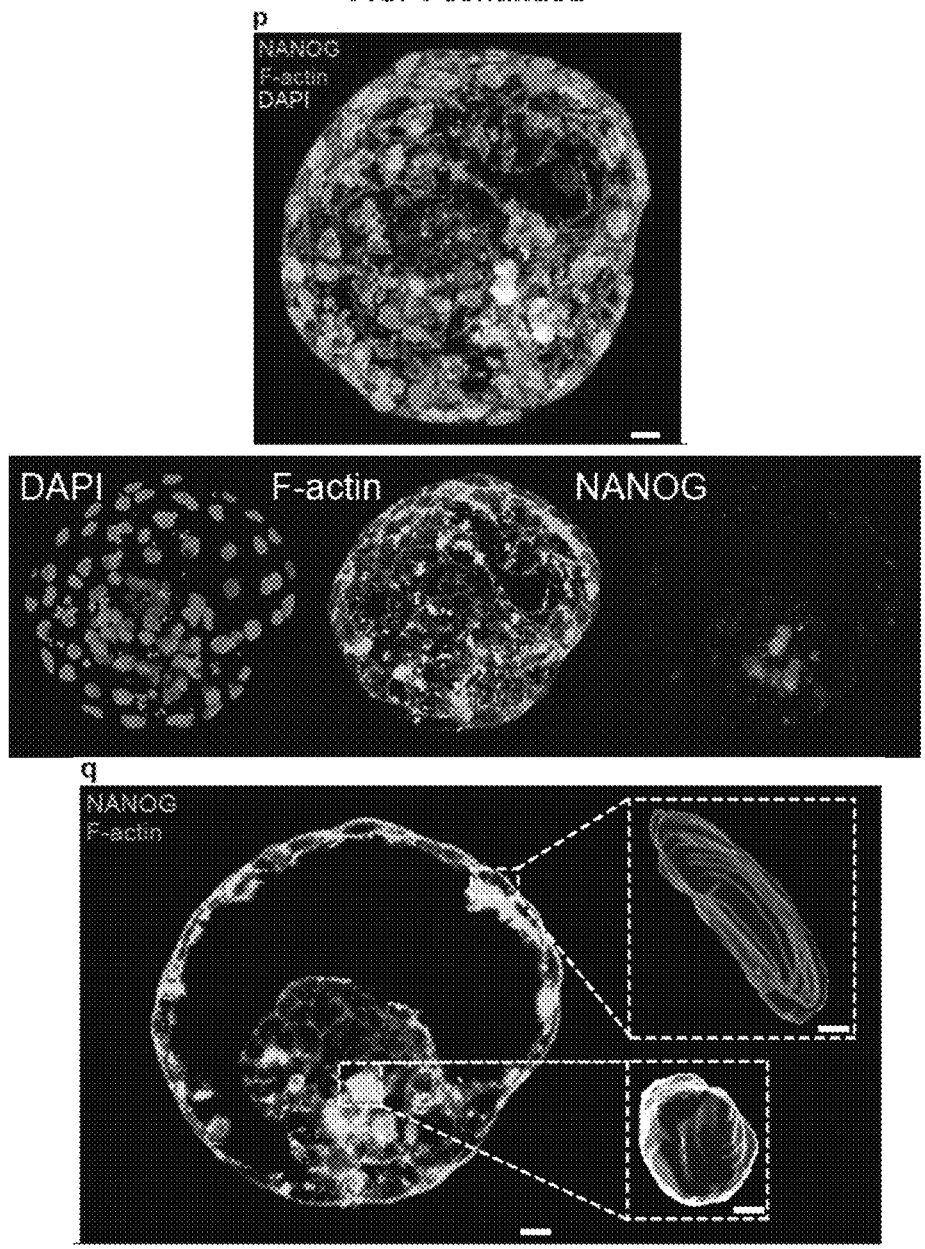

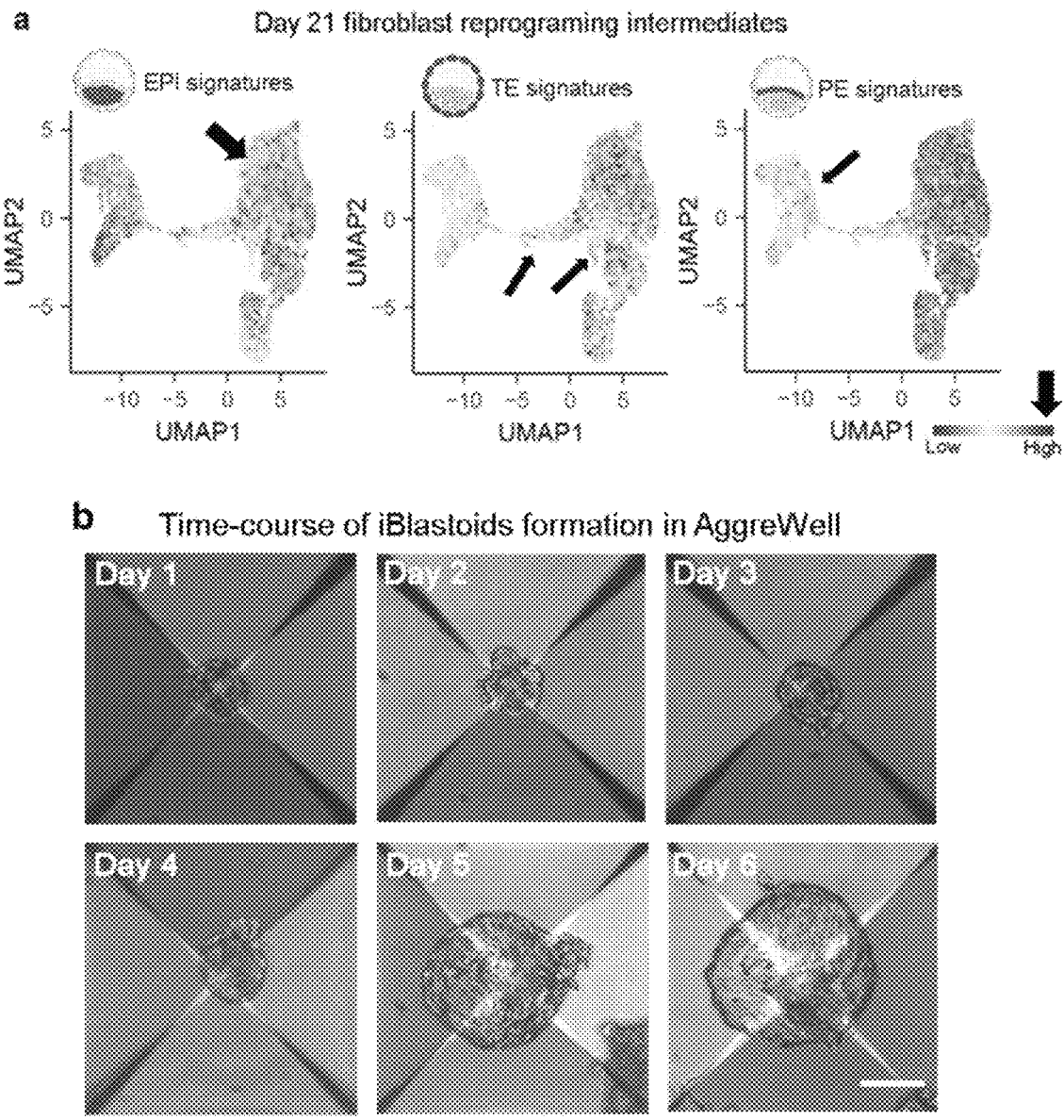

FIG. 2 continued

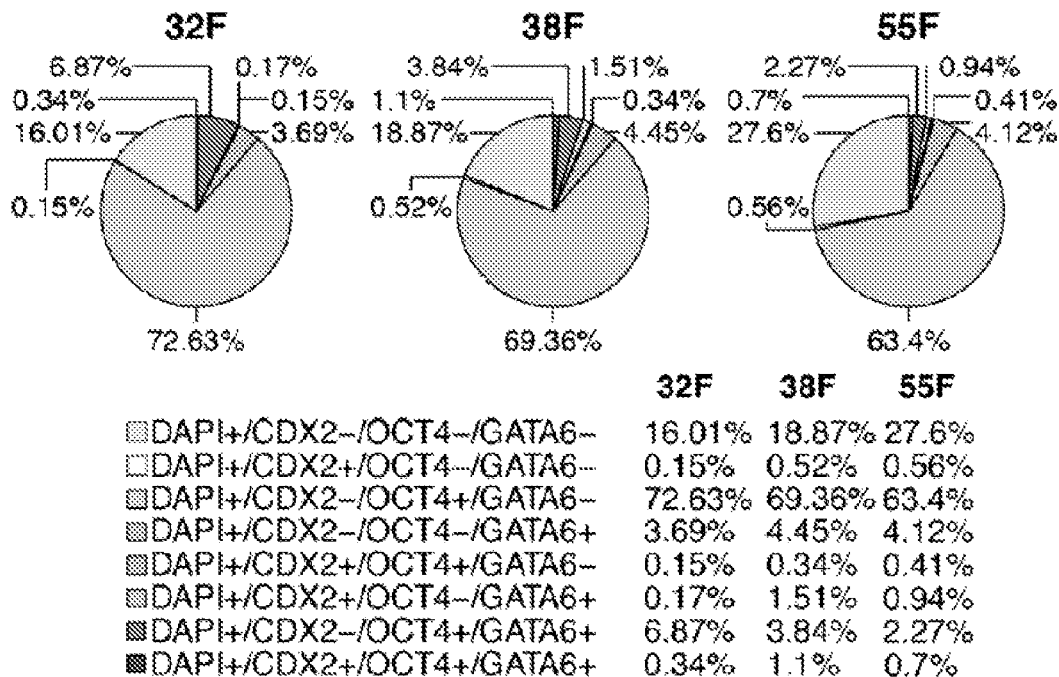

| | Grade | Rating | Description |
|---|---|---|---|
| Stage of development | 1 | | Early |
| | 2 | | Blastocyst |
| | 3 | | Expanded |
| | 4 | | Hatched/hatching |
| ICM | 1 | Good | Prominent, easily discernible, with many cells that are compacted and tightly adhered together |
| | 2 | Fair | Easily discernible, with many cells that are loosely grouped together |
| | 3 | Poor | Difficult to discern, with few cells |
| TE | 1 | Good | Many cells forming a cohesive epithelium |
| | 2 | Fair | Few cells forming a loose epithelium |
| | 3 | Poor | Very few cells | j k k l m

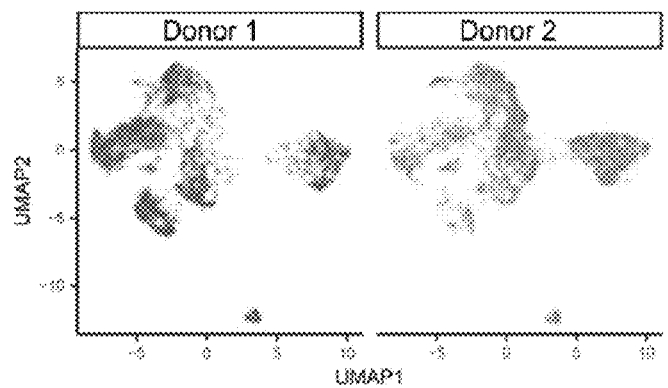
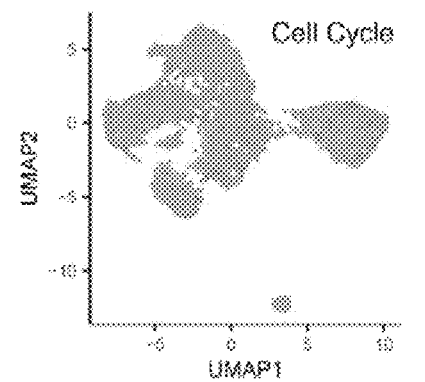
FIG. 4B
FIG. 4C
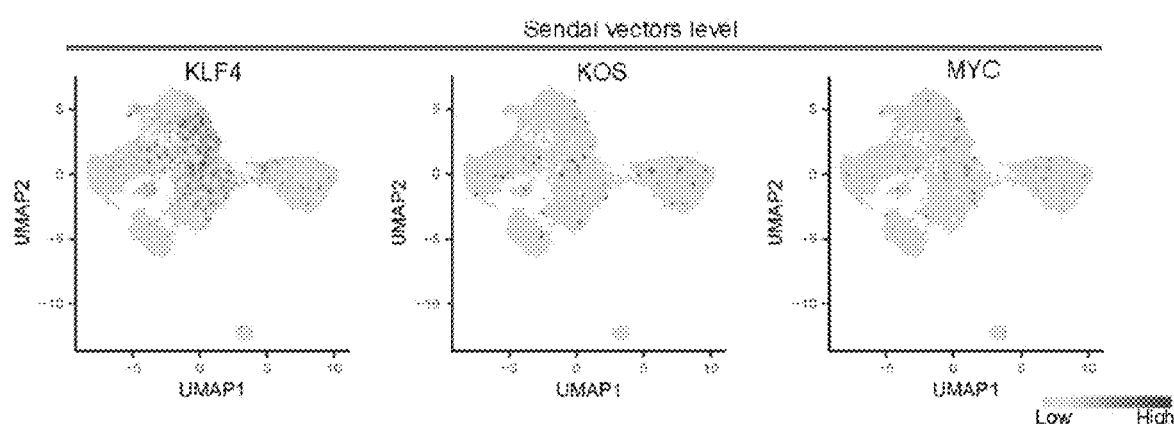
FIG. 4D h i j k

METHODS AND CELLULAR STRUCTURES

RELATED APPLICATIONS

This application claims priority to, and the benefit of from Australian Patent Application No. 2020904338, filed Nov. 24, 2020, Australian Patent Application No. AU 2021900685, filed Mar. 10, 2021, Australian Patent Application No. 2021902865, filed Sep. 3, 2021 and Australian Patent Application No. 2021903427, filed Oct. 26, 2021. The contents of each of the aforementioned patent applications are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Nov. 23, 2021, is named "FRPA-024_001 US_SeqList.txt" and is about 2,571 bytes in size.

FIELD OF THE INVENTION

The invention relates to methods and compositions for generating human blastocyst-like structures.

BACKGROUND OF THE INVENTION

Mammalian embryogenesis begins with the totipotent zygote that is capable of developing into the morula, followed by the formation of a blastocyst. As the embryo implants, cells of the epiblast (EPI) lineage within the blastocyst will develop into the embryo proper and amnion, whereas cells of the trophectoderm (TE) and primitive endoderm (PE) will eventually give rise to the placenta and yolk sac, respectively.

When isolated and cultured in vitro, cells of the epiblast give rise to human embryonic stem cells (hESCs). Alternatively, adult cells can be reprogrammed into human induced pluripotent stem cells (hiPSCs) by transcription factor-mediated reprogramming. These pluripotent in vitro cultured cells can be differentiated into all the cell types of the body and, as such, they have been pivotal for the development of human 'mini organs' or organoid models. Moreover, a number of in vitro models have been developed using hESCs/hiPSCs to study early human development, including micropatterned embryonic disc-like structures, embryonic sac-like structures, and human gastruloids. This technological and medical revolution has been of great importance for disease modelling, drug screening, and our understanding of the molecular mechanisms of several diseases, embryo and organ development.

However, despite the importance for the entire future of the individual on the complex spatio-temporal/cellular and molecular changes occurring during the early phases of blastocyst development, an EPI/TE/PE integrated in vitro model of the human blastocyst has not been reported. To date, the only way to study the critical first days of human development is through the use of donated blastocysts consented to research following in vitro fertilization (IVF). This poses a myriad of challenges, as the purpose of IVF in most cases is to generate embryos for reproductive purposes, with only surplus (potentially lower quality) embryos used for research. This, combined with the myriad ethical, legal, and policy constraints in different countries around the world vastly limits the number of laboratories permitted to work with human blastocysts, and therefore our understanding of early human embryo development.

In the last few years, different groups have successfully generated in vitro models of mouse blastocysts, called blastoids. These mouse blastoids have been generated using two different approaches: (1) by assembling different blastocyst-like cells together including mouse embryonic stem cells (ESCs) with trophoblast stem cells (TSCs); ESCs, TSCs, and extraembryonic endoderm (XEN) stem cells; extended (or expanded) pluripotent stem cells (EPSCs) with TSCs or by (2) differentiating EPSCs into blastocyst-like structures.

However, there are no reports of generating human blastoids, likely due to the challenges in deriving and maintaining stem cell types of the human blastocyst in culture.

Accordingly, there is a need to produce a human blastoid or a structure of human cells that models a human blastocyst.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

In one aspect, the present invention provides a method of producing a multi-layered cellular structure, the method comprising:
 a) obtaining a cell population of reprogrammed somatic cells exhibiting epiblast (EPI), trophectoderm (TE), and/or primitive endoderm (PE) transcriptional signatures; and
 b) culturing the reprogrammed somatic cells under conditions that allow aggregation to obtain a multi-layered cellular structure;
 thereby producing a multi-layered cellular structure.

In one aspect, the present invention provides a method of producing a blastocyst-like structure, the method comprising:
 a) obtaining a cell population of reprogrammed somatic cells exhibiting epiblast (EPI), trophectoderm (TE), and/or primitive endoderm (PE) transcriptional signatures; and
 b) culturing the reprogrammed somatic cells under conditions that allow aggregation to obtain a blastocyst-like structure;
 thereby producing a blastocyst-like structure.

In any aspect, obtaining a cell population of reprogrammed somatic cells exhibiting epiblast (EPI), trophectoderm (TE), and primitive endoderm (PE) transcriptional signatures comprises:
 increasing the protein expression or amount of one or more factors in a population of somatic cells, wherein the factors are for reprogramming the somatic cells towards a dedifferentiated or pluripotent state; and
 culturing the cells for a sufficient time and under conditions to allow the reprogramming of the cells towards a dedifferentiated or pluripotent state.

In any aspect, the population of cells exhibiting transcriptional signatures of the epiblast (EPI), trophectoderm (TE), and/or primitive endoderm (PE) lineages preferably exhibits transcriptional signature of each of the epiblast (EPI), trophectoderm (TE), and primitive endoderm (PE) lineages.

In any aspect, a population of cells exhibiting transcriptional signatures of the EPI, TE or PE lineage comprises a population of cells expressing at least one of the markers listed in Table 1 herein. More preferably, a transcriptional signature of the EPI lineage comprises expression of at least 2, at least 3, at least 4, at least 5, at least 10, at least 15, at least 20, at least 30, at least 40, at least 50, at least 60, at least 70 or more or all of the markers of the EPI lineage as listed in Table 1 herein. More preferably, a transcriptional signature of the TE lineage comprises expression of at least 2, at least 3, at least 4, at least 5, at least 10, at least 15, at least 20, at least 30, at least 40, at least 50, at least 60, at least 70 or more or all of the markers of the TE lineage as listed in Table 1 herein. More preferably, a transcriptional signature of the PE lineage comprises expression of at least 2, at least 3, at least 4, at least 5, at least 10, at least 15, at least 20, at least 30, at least 40, at least 50, at least 60, at least 70 or more or all of the markers of the PE lineage as listed in Table 1 herein.

In one aspect, the present invention provides a method of producing a blastocyst-like structure, the method comprising the following steps in order:
  a) increasing the protein expression or amount of one or more factors in a population of somatic cells, wherein the factors are for reprogramming the somatic cells towards a dedifferentiated or pluripotent state;
  b) culturing the cells for a sufficient time and under conditions to allow the reprogramming of the cells towards a dedifferentiated pluripotent state, to obtain a population of cells exhibiting one or more characteristics of the EPI, TE and PE lineages;
  c) contacting the cells with a culture medium comprising an agent for activating WNT pathway signalling (optionally a GSK-3 inhibitor), at least one, preferably two, TGF-3 inhibitors, an HDAC inhibitor, EGF, and BMP4, under conditions that allow aggregation;
  d) culturing the cells in the culture medium for a sufficient time and under conditions to allow the cells to exhibit at least one characteristic of a blastocyst-like structure as described herein,
  thereby producing a blastocyst-like structure.

Preferably, the culture medium in step c) further comprises a Rho-kinase (ROCK) inhibitor. Preferably, the cells are contacted with the culture medium comprising the ROCK inhibitor for a period of at least about 6 hours, at least about 12 hours, or at least about 24 hours before the cells are subsequently contacted with the culture medium without the ROCK inhibitor.

It will be understood that any method for reprogramming a somatic cell towards a de-differentiated or pluripotent state can be used in accordance with the methods of the present invention. As such, the present invention is not limited by the particular method for increasing the protein expression or amount of relevant factors, or culturing conditions to allow the somatic cell to commence reprogramming towards plasticity or pluripotency. Such methods are known in the art and are further described herein.

In preferred embodiments, the factors for reprogramming the somatic cell towards a dedifferentiated or pluripotent state are transcription factors. The transcription factors may comprise one or more of, or consist or consist essentially of the factors: OCT4, SOX2, KLF4 and MYC (OSKM); SOX2, KLF4 and OCT4 (SKO); OCT4, SOX2, KLF4 and GLIS1 (OSKG); OCT4, SOX2, NANOG and LIN28 (OSNL); or OCT4, SOX2, KLF4, c-MYC, NANOG and LIN28 (OKSMNL). In particularly preferred embodiments, the transcription factors comprise all four of the factors OCT4, SOX2, KLF4 and MYC (OSKM), or variants thereof. In another embodiment, the transcription factors comprise, consist or consisting essentially of SOX2, KLF4 and OCT4 (SKO). In another embodiment, the transcription factors comprise, consist or consisting essentially of OCT4, SOX2, KLF4 and GLIS1 (OSKG). In another embodiment, the transcription factors comprise, consist or consisting essentially of OCT4, SOX2, NANOG and LIN28 (OSNL). In another embodiment, the transcription factors comprise, consist or consist essentially of OCT4, SOX2, KLF4, c-MYC, NANOG and LIN28 (OKSMNL).

Accordingly, in another aspect, the present invention provides a method of producing a blastocyst-like structure, the method comprising the following steps in order:
  a) increasing the protein expression or amount of one or more of the transcription factors OCT4, SOX2, KLF4 and MYC (OSKM), SOX2, KLF4 and OCT4 (SKO), OCT4, SOX2, KLF4 and GLIS1, or OCT4, SOX2, NANOG and LIN28 (OSNL), or any other combination of transcription factors described herein, in a population of somatic cells;
  b) culturing the cells for a sufficient time and under conditions to allow the reprogramming of the cells towards a dedifferentiated pluripotent state, preferably wherein the culturing of the cells is in media that is suitable for maintenance of somatic cells;
  c) contacting the cells with a culture medium comprising an agent for activating WNT pathway signalling (optionally a GSK-3 inhibitor), at least one, preferably two, TGF-3 inhibitors, a HDAC inhibitor, EGF, and BMP4 under conditions that allow aggregation;
  d) culturing the cells in the culture medium for a sufficient time and under conditions to allow the cell to exhibit at least one characteristic of a blastocyst-like structure as described herein,
  thereby producing a blastocyst-like structure.

Typically, the protein expression, or amount, of a transcription factor as described herein is increased by contacting the cells with an agent which increases the expression of the transcription factor. Preferably, the agent is selected from the group consisting of: a nucleotide sequence, a protein, an aptamer and small molecule, ribosome, RNAi agent, microRNAs, long non-coding RNAs and peptide-nucleic acid (PNA) and analogues or variants thereof. In some embodiments, the agent is exogenous. The present invention also contemplates the use of a transcriptional activation system (e.g., a gRNA for use in a gene activation system such as CRISPR/Cas9 or TALEN) for increasing the expression of the one or more transcription factors.

Typically, the protein expression, or amount, of a transcription factor as described herein is increased by introducing at least one nucleic acid (eg an mRNA) comprising a nucleotide sequence encoding a transcription factor, or encoding a functional fragment thereof, in the cell. The at least one nucleic acid encoding a transcription factor may be transfected into the population of somatic cells multiple time, for example 2, 3, 4, 5 or 6 times, for example each day for 2, 3, 4, 5 or 6 days, respectively.

In a preferred embodiment of the invention, the nucleic acid sequence encoding a transcription factor protein is introduced into a cell by a plasmid. One or more nucleic acids encoding one or more transcription factors may be used. Therefore, it is apparent that one or more plasmids may be used for the purpose of increasing the expression or amount of the required one or more transcription factors. In other words, the nucleic acid sequences may be in or on a single plasmid, or provided to the somatic cell in two or more plasmids.

In any embodiment of the present invention, the plasmid containing the nucleic acid encoding the one or more transcription factors for use according to the invention may be an episomal plasmid.

Preferably, the nucleic acid further includes a heterologous promoter. Preferably, the nucleic acid is in a vector, such as a viral vector or a non-viral vector. Preferably, the vector is a viral vector comprising a genome that does not integrate into the host cell genome. The viral vector may be a retroviral vector, a lentiviral vector an adenovirus or Sendai virus.

In certain embodiments, the protein expression or amount of the factors is increased in the somatic cell by transduction or transfection of the somatic cell with one or more vectors encoding said transcription factors. The vector may be a viral vector, including an integrating or non-integrating viral vector. In further embodiments, the vector may be an episomal vector.

It will also be understood that the somatic cell does not need to have completed reprogramming to the pluripotent state prior to the step of contacting the cell with the culture medium defined in step c). In other words, the cell is preferably at an intermediate state, transitioning from differentiated state to a more plastic state or towards a pluripotent state when it is contacted with the culture medium. Therefore, the cells at the end of step b) and before culturing in step c) may be referred to as "reprogramming intermediates". As described herein, the population of reprogramming intermediates exhibits epiblast (EPI), trophectoderm (TE), and/or primitive endoderm (PE) transcriptional signatures. A population of reprogramming intermediates made according to the present invention may also be characterised by reference to the proportion of different cell populations staining positive or negative for markers OCT4, GATA6 and CDX2, as show in FIG. 2h herein.

In certain embodiments, the period of time for culturing the cell to commence reprogramming towards a dedifferentiated or pluripotent state is at least 1 day following increasing the protein expression, or amount of the one or more factors or starting from when the cells are contacted with an agent to increase protein expression, or amount of the one or more factors. The period of time may be 2, 3, 4, 5, 6, 7, 8, 9, 10, 11, 12, 13, 14, 15, 16, 17, 18, 19, 20 or 21 or more days after increasing the protein expression, or amount of the one or more factors. In any embodiment, the period of time for culturing the cell to commence reprogramming towards a dedifferentiated or pluripotent state may be any period of time provided that it enables the reduction of markers associated with the somatic cell and/or causes a reduction or loss of somatic cell identify and gain of cell plasticity.

In one embodiment, the step of culturing the cells for a sufficient time and under conditions to allow the reprogramming of the cells towards a dedifferentiated or pluripotent state comprises culturing the cells in media for maintaining the somatic cells in culture. Preferably, this step comprises culturing the cells in media which is not intended for promoting pluripotency. In other words, if the somatic cells being reprogrammed are fibroblasts, preferably the cells are cultured in media suitable for maintaining fibroblasts. If the somatic cells being reprogrammed are epithelial cells, preferably the cells are cultured in media suitable for maintaining epithelial cells. Suitable media for the culturing and maintain various somatic cells types are known to the skilled person and also further defined herein in Table 3b.

In another embodiment, the step of culturing the cells for a sufficient time and under conditions to allow the reprogramming of the cells towards a dedifferentiated or pluripotent state comprises culturing the cells in media which is not intended for promoting only pluripotency. Exemplary media includes NACL, PA or t2iLGo medium defined herein, including in Table 3a.

In further embodiments of the invention, the methods above include culturing the somatic cells towards a dedifferentiated or pluripotent state in a medium that induces upregulation of the EPI, TE and PE lineage transcriptional signatures. Preferably, when the somatic cells are fibroblasts, the medium is a fibroblast medium, for example the fibroblast medium defined herein, including in Table 3a or 3b.

In any embodiment, the period of time between increasing the protein expression or amount of the factors and contacting the cell with the culture medium in step c) may be any period of time provided that it enables the reduction of markers associated with the somatic cell. In further examples, the period of time between increasing the protein expression or amount of the factors and contacting the cell with the culture medium in step c) may be any period of time provided that it enables the cell to proceed through mesenchymal to epithelial transition states. In further or alternative embodiments, the period of time can be any period provided that it enables the expression of epiblast (EPI), trophectoderm (TE), and primitive endoderm (PE) transcriptional signatures.

As used herein, the culture medium in step c) (i.e., the culture medium for contacting reprogramming intermediates exhibiting EPI, TE and PE lineage transcriptional signatures) may also be referred to as a blastocyst promoting medium or "iBlastoid" medium. Preferably, the blastocyst promoting medium or iBlastoid medium is any as defined herein. In any embodiment, the cells are cultured in the culture medium in step c) for a period of at least about 1, at least about 2, at least about 3, at least about 4, at least about 5, at least about 6, at least about 7, at least about 9, at least about 12, at least about 14, at least about 16, at least about 20, at least about 24, or at least about 28 or more days.

In any aspect, conditions that allow aggregation or self-organisation may comprise culturing on any culture plate, culture vessel, microfluidic devices or culture system that allows three-dimensional aggregation or self-organisation of cells. For example, the cells may be seeded at a density of at or about 0.5 to $2 \times 10^5$ cells per well, at or about 0.6 to $2 \times 10^5$ cells per well, at or about 0.8 to $2 \times 10^5$ cells per well, at or about 1 to $2 \times 10^5$ cells per well, at or about $0.6 \times 10^5$ cells per well, at or about $0.8 \times 10^5$ cells per well, at or about $1 \times 10^5$ cells per well, at or about $1.2 \times 10^5$ cells per well, at or about $1.4 \times 10^5$ cells per well, at or about $1.6 \times 10^5$ cells per well, at or about $1.8 \times 10^5$ cells per well, or at or about $2 \times 10^5$ cells per well. It will be appreciated that within one well (in a 24-well format AggreWell™), there are 1200 microwells. Accordingly, the cells may be seeded at a density of at or about 1 to 100 cells per microwell, preferably about 10 to 200 cells per microwell, more preferably at a density of about 50 to 100 cells per microwell. In one embodiment, the culture plate or culture vessel is any one described herein. In certain embodiments, the culture plate or culture vessel is a 24-well AggreWell™.

A somatic cell may be any cell type described herein, including a diseased cell. Preferably the somatic cell is a human somatic cells. The somatic cell may be an adult cell or a cell derived from an adult which displays one or more detectable characteristics of an adult or non-embryonic cell. The diseased cell may be a cell displaying one or more detectable characteristics of a disease or condition, for example aneuploidy, Hydatidiform mole, or Cornelia de Lange syndrome. Further, the somatic cells may have been gene edited, for example by CRISPR technology (e.g. CRISPR-Cas9, -Cas12a, -Cas13 or related CRISPR/nuclease systems).

In preferred embodiments, the somatic cell is a fibroblast, preferably a dermal fibroblast, most preferably a human fibroblast.

In a further aspect, the present invention provides a method of producing a multi-layered cellular structure or blastocyst-like structure, the method comprising:
culturing an iPSC and iTSC cell under conditions that allow assembly and aggregation of the cells to obtain a multi-layered cellular structure;
thereby producing a multi-layered cellular or blastocyst-like structure.

Preferably, the iPSC and iTSCs are derived from human cells (e.g., obtained from reprogramming of human somatic cells). Preferably, the iPSCs and iTSCs are derived from reprogramming of fibroblasts.

In this aspect of the invention, the iPSCs and iTSCs may be generated by any method known in the art and as further described herein.

In this aspect of the invention, the conditions allowing assembly and aggregation of the cells preferably comprise co-culturing of the iPSCs and iTSCs in any culture vessel described herein, which promotes self-organisation and assembly of the cells. Preferably, the cells are cultured in any culture medium for promoting cells (e.g. a blastocyst promoting medium or iBlastoid medium) to exhibit at least one characteristic of a blastocyst-like structure as described herein. Preferably, the culture medium is an iBlastoid medium as shown in Table 3a.

Preferably, the iPSC and iTSC are co-cultured in the same well at respective 1:2.5 ratio with a total number of $1.2 \times 10^5$ cells per well. It will be appreciated that within one well (in a 24-well format AggreWell™), there are 1200 microwells. Accordingly, the cells may be seeded at a density of at or about 10 to 200 cells per microwell, preferably at a density of about 50 to 100 cells per microwell.

The invention also provides a multi-layered cellular structure or blastocyst-like structure, preferably wherein the multi-layered cellular structure is obtained or obtainable by any method as described herein. Such multi-layered cellular structures or blastocyst-like structures may also be termed in vitro-derived or in vitro-generated blastoids or blastocyst-like structures or "iBlastoids". Accordingly, the invention also provides an in vitro-derived or an in-vitro generated blastoid or blastocyst-like structure. Preferably, the in vitro-derived or an in-vitro generated blastoid or blastocyst-like structure is obtainable or obtained by any method described herein. In any embodiment, the multi-layered cellular structure or blastocyst-like structure is a human multi-layered cellular structure or human blastocyst-like structure (or human blastoid or iBlastoid). Preferably, the multi-layered cellular structure or blastocyst-like structure only contains, or was derived or generated from, human cells.

In any aspect described herein, the multi-layered cellular structure or blastocyst-like structure comprises an inner cell layer and an outer cell layer, the inner cell layer comprises cells that exhibit one or more characteristics of cell of the epiblast and/or the primitive endoderm lineage, and the outer cell layer comprises cells that exhibit one or more characteristics of a cell of the trophectoderm. Preferably the characteristic may be determined by analysis of cell morphology, gene expression profiles, activity assay, protein expression profile, surface marker profile, differentiation ability or a combination thereof. Examples of characteristics or markers include those that are described herein and those known to the skilled person.

In any aspect, the inner cell layer further comprises a cluster of cells that exhibit one or more characteristics of the PE. Preferably the cells that exhibit one or more characteristics of the PE are, or are predominantly, peripheral to the cells that exhibit one or more characteristics of a cell of the epiblast.

In any aspect, the characteristic of an EPI cell is the presence of any one or more of the markers NANOG, OCT4 (also known as POU5F1) or SOX2. In one embodiment, more cells in the multi-layered cellular structure or blastocyst-like structure express OCT4 than express NANOG.

In any aspect, the characteristic of an EPI cell is the morphology of a rounded columnar appearance.

In any aspect, the characteristic of a TE cell is the presence of one or more of the markers CDX2 and GATA2.

In any aspect, the characteristic of a TE cell is a flattened or elongated epithelial morphology.

In any aspect, the characteristic of a PE cell is the presence of the marker SOX17 or GATA6.

In any aspect, a marker of the EPI, PE or TE lineage is as described in Petropoulos et al., *Cell* 165, 1012-1026 (2016) or as set forth in Table 1 herein.

In any aspect, the multi-layered cellular structure or blastocyst-like structure may further comprises GATA6 positive cells (optionally with low or weak CDX2 staining) neighbouring OCT4 positive cells.

In any aspect, the multi-layered cellular structure or blastocyst-like structure exhibits the main morphological features of pre-implantation human blastocysts at E5-7. Further, the multi-layered cellular structure or blastocyst-like structure may also comprise cells that exhibit one or more characteristics of cell of the epiblast, primitive endoderm and trophectoderm cells where those cells adopt the same or similar relative spatial arrangement as epiblast, primitive endoderm and trophectoderm cells, respectively, in human blastocysts at E5-7, preferably E6-7.

In any aspect, the multi-layered cellular structure or blastocyst-like structure also comprises a cell free cavity, or blastocoel-like cavity.

In any aspect, the multi-layered cellular structure or blastocyst-like structure is capable of forming a primitive yolk sac, similarly to the yolk sac formed by a naturally occurring embryo.

In any aspect, the multi-layered cellular structure or blastocyst-like structure has an x- and y-axis diameter, x:y aspect ratio and/or projection area of a size of between about 50% to 200% of previously published measurements of human blastocysts at embryonic day 5-7 (E5-7) post-fertilization. For example, the x- and/or y-axis diameter of the multi-layered cellular structure or blastocyst-like structure is from about 100 to about 300 μm. Preferably, the x/y axis ratio is about 1. The projection area of the multi-layered cellular structure or blastocyst-like structure is about 5,000 to about 10,000 μm², about 10,000 to about 40,000 μm², about 40,000 μm² to about 60,000 μm², preferably about 20,000 to about 40,000 μm².

In any aspect, the multi-layered cellular structure or blastocyst-like structure comprises at least about 100 to 400 total cells, or at least about 300 to about 600 cells.

In any aspect, when cultured in IVC1 media (as defined herein) for 1 day and subsequently cultured in IVC2 media (as defined herein) from day 2 to day 4.5, the multi-layered cellular structure or blastocyst-like structure may attach to a surface (such as a glass surface) and exhibit one of more of the following:
a) increase in size, flattening and progressing to form an outgrowth;
b) an increase in the number of NANOG and OCT4/SOX2 positive cells;
c) a spread of CDX2 and GATA2 positive cells;
d) SOX17 and GATA6 positive cells localize to the perimeter of the NANOG or OCT4 positive cells;
e) expression of keratin KRT7 or other trophoblast marker in the outer cell layer or cells exhibiting at least one characteristic of a TE cell;
f) presence of cells which morphologically resemble syncytiotrophoblast (ST) and extravillous cytotrophoblasts (EVT) (e.g. ST and EVT-like cells, respectively), for example a multi-nucleated phenotype and spindle-like morphology;
g) presence of cells expressing hCG (an exemplary ST marker), and MMP2 (an exemplary EVT marker);
h) presence of cells exhibiting upregulation of the ST marker CSH1 and EVT marker ITGA1.

In another aspect, the present invention provides a culture medium for promoting cells (e.g. a blastocyst promoting medium or iBlastoid medium) to exhibit at least one characteristic of a blastocyst-like structure, the culture medium comprising:
an agent for activating signalling of the WNT pathway, optionally a GSK-3 inhibitor;
at least one, preferably two, TGF-3 inhibitors,
a HDAC inhibitor,
a GSK-3 inhibitor,
EGF, and
BMP4.

In this aspect, the activator of WNT pathway signalling, TGF-3 inhibitor(s), and HDAC inhibitor may be any one known in the art, including any one described herein.
Preferably, the culture medium further comprises:
ITS-X;
L-Glutamine;
N-acetyl-L-cysteine;
B-estradiol;
Progesterone;
2-mercaptoethanol;
L-ascorbic acid;
Transferrin (e.g. human);
Insulin (e.g. human);
N2 supplement; and
B27 supplement.
Preferably, the progesterone, transferrin and insulin are provided in a N2 supplement as described herein, further including putrescine and selenite.
Preferably, the B27 supplement comprises biotin, DL alpha tocopherol acetate, DL alpha tocopherol, Vitamin A (Acetate), BSA, catalase, Insulin (human), superoxide dismutase, corticosterone, D-galactose, Ethanolamine HCL, Glutathione, L-Carnitine HCL, Linoleic Acid, Linolenic Acid, Progesterone, Putrescine 2HCl, Sodium Selenite, T3 (triodo-l-thyronine).
In any embodiment, the culture medium further comprises an antibiotic, for example penicillin-streptomycin.
In one embodiment, the culture medium comprises:
IVC1 medium, N2B27 basal medium and TSC basal medium as defined herein in a respective 2:1:1 ratio,
an activator of WNT pathway signalling (optionally a GSK-3 inhibitor),
at least one, preferably two, TGF-3 inhibitors,
a HDAC inhibitor,
EGF, and
BMP4.

In any aspect herein, an agent for activating WNT pathway signalling may include any small molecule that directly or indirectly activates WNT signalling. In certain embodiments, the agent for activating WNT pathway signalling may be a GSK-3 inhibitor.

In any aspect, a TGF-β pathway inhibitor is selected from SB431542 and A83-01, the histone deacetylase (HDAC)1 inhibitor is VPA (Valproic Acid), the GSK-3 Inhibitor is CHIR99021.

In any aspect, a GSK-3 Inhibitor is at a concentration of, or about, 2 µM, the TGF-β pathway inhibitor is at a concentration of, or about, 0.5 µM or 1 µM, histone deacetylase (HDAC)1 inhibitor is at a concentration of, or about, 0.8 mM, EGF is at a concentration of, or about, 50 ng/ml, and BMP4 is at a concentration of, or about, 10 ng/ml.

In any aspect or embodiment, the culture medium further comprises a ROCK inhibitor or any growth factor or kinase inhibitor capable of promoting cell survival after single-cell dissociation. Preferably, the ROCK inhibitor is Y-27632. Preferably, the ROCK inhibitor is at a concentration of, or about, 10 µM.

In another aspect, the culture medium for use in step c) comprises or consists of the Fibroblast medium, the N2B27 basal medium, the TSC basal medium, the IVC1 medium, the IVC2 medium or the Human iBlastoid medium as defined in Table 3a.

In any aspect, the culture medium defined in step c) of any method of the invention may be any culture medium of the invention, including but not limited to the Human iBlastoid medium as defined herein, including in Table 3a.

In any aspect, the somatic cells may have a disease genotype. For example, the somatic cells may be derived from an individual having a genetic disease, preferably an early developmental disease. Examples of early developmental diseases are Aneuploidy, Hydatidiform mole, and Cornelia de Lange syndrome.

The multi-layered cellular structure or blastocyst-like structure(s) (iBlastoids) of the invention, preferably made in accordance with the methods of the invention, may be utilized as a representative model to understand the side effects of xenobiotics and other potential environmental hazards during the delicate stages of human early development, which would likely also facilitate the prediction and subsequent formulation of specific drug regimens for patients preparing for pregnancy.

The multi-layered cellular structure or blastocyst-like structure(s) of the invention, preferably made according to the methods of the present invention, can be used as a platform for a variety of other uses including: for use in testing/developing CRISPR-based technology, to develop/improve in vitro attachment assays, for studying embryonic development and development of extra-embryonic tissues (such as the placenta).

In another aspect, the present invention also provides a method of identifying an agent capable of modulating blastocyst development (optionally to improve approaches associated with in vitro fertilisation technology) and/or activity, the method comprising:
contacting a multi-layered cellular structure or blastocyst-like structure of the invention, preferably made according to the present invention, with a candidate agent;
comparing development and/or activity of the a multi-layered cellular structure or blastocyst-like structure following the contacting with the agent, to the development and/or activity of a multi-layered cellular structure or blastocyst-like structure without the agent, wherein the effect of the agent on the development and/or activity of the a multi-layered cellular structure or blastocyst-like structure above a predetermined level relative to the development of the a multi-layered cellular structure or blastocyst-like structure without the agent is indicative that the agent modulates trophoblast development and/or activity.

In another aspect, the present invention provides a method for obtaining a compound or particle produced by a multi-layered cellular structure or blastocyst-like structure, the method comprising culturing a multi-layered cellular structure or blastocyst-like structure according to the present invention and isolating from the culture medium a compound or particle secreted by the cells, thereby obtaining the compound produced by the multi-layered cellular structure or blastocyst-like structure. The compound may be a hormone or growth factor. The particle may be an extracellular vesicle, such as an exosome.

The multicellular structure or blastocyst-like structure(s) of the present invention, preferably produced according to a method described herein, may be useful in the generation of chimeric organs or organoids. Accordingly, the present invention also provides a use of a multicellular structure or blastocyst-like structure(s) of the present invention, preferably produced according to a method described herein, in the generation of a chimeric organ or organoid. Such chimeric organoids may be useful for the study of various conditions or diseases or for screening therapeutic agents.

In another aspect, the present invention also relates to kits for producing a multi-layered cellular structure or blastocyst-like structure as disclosed herein. In some embodiments, a kit comprises a somatic cell, reprogramming factors, and one or more culture medium as disclosed herein. Preferably, the kit can be used to produce a multi-layered cellular structure or blastocyst-like structure. Preferably, the kit can be used with a somatic cell that is a fibroblast. In some embodiments, the kit further comprises instructions for reprogramming a somatic cell to a multi-layered cellular structure or blastocyst-like structure according to the methods as disclosed herein. Preferably, the present invention provides a kit when used in a method of the invention described herein.

In further aspects, the present invention provides a cell or population of cells derived from, isolated from or obtained from the multicellular structure or blastocyst-like structure(s) of the invention, preferably produced according to a method described herein. The cell or population of cells may exhibits one or more characteristics of the EPI lineage, or one or more characteristics of the PE lineage, or one or more characteristics of the TE lineage.

Typically, the cells or population of cells derived from, isolated from, or obtained from a multicellular structure or blastocyst-like structure of the invention, preferably produced according to the methods of the invention, are capable of self-renewal. In other words, the cells or population of cells derived from, isolated from, or obtained from a multicellular structure or blastocyst-like structure of the invention, preferably produced according to the methods of the invention, are characterised in that they can be maintained in culture.

In further aspects, the present invention also provides an organoid derived from or obtained from a cell or cell population described herein. The organoid may also comprise a chimeric organoid derived from the multicellular structure or blastocyst-like structure of the invention, preferably produced according to a method described herein.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 4A-G. scRNA-seq pipeline and quality controls. FIG. 4A shows a scRNA-seq analysis strategy (see Methods for details). FIG. 4B shows a UMAP representation of donor cell distribution for iBlastoids. FIG. 4C shows a UMAP representation of the cell cycles for iBlastoids scRNA-seq library. FIG. 4D shows expression of Sendai-KLF4, Sendai-KOS and Sendai-MYC in iBlastoids. FIG. 4E shows Expression of EPI markers (POU5F1 and NANOG), TE markers (CDX2 and GATA2), and PE markers (SOX17 and GATA6) for Petropoulos scRNA-seq library (Petropoulos). FIG. 4F and FIG. 4G show expression of non-reprogramming signature and IFI27 expression on UMAP of iBlastoid dataset.

DETAILED DESCRIPTION OF THE EMBODIMENTS

Figure 1:
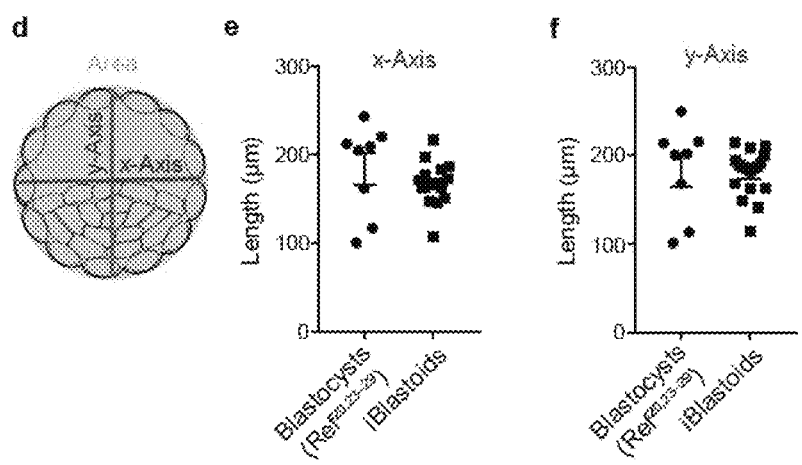
FIG. 1. Generation of human iBlastoids by reprogramming. a, Experimental design for reprogramming and iBlastoid derivation. b, Phase-contrast image of iBlastoid (n=5). Scale bar, 50 µm. c, Phase-contrast and immunostaining images of iBlastoids for NANOG (n=5). Scale bar, 50 µm. d-h, Measurement of x- and y-axis diameter, x/y aspect ratio, projection area of iBlastoids (n=18) compared to human blastocysts (Shahbazi, M. N. et al. Nat. Cell Biol. 18, 700-708 (2016); Blakeley, P. et al. Development 142, 3613 (2015); Petropoulos, S. et al. Cell 165, 1012-1026 (2016); Xiang, L. et al. Nature 577, 537-542 (2020); Qin, H. et al. Cell Rep. 14, 2301-2312 (2016); Liu, L. et al. Nat. Commun. 10, 364 (2019); Durruthy-Durruthy, J. et al. Dev. Cell 38, 100-115 (2016); Fogarty, N. M. E. et al. Nature 550, 67-73 (2017)) (n=8). i, Total cell number estimation of iBlastoids (n=14). j, 3D and 2D representation of iBlastoids stained for CDX2 and NANOG (n=5). Scale bar, 20 µm. k-l, Representative DIC representation and CDX2, NANOG immunostaining of iBlastoids (n=5) illustrating the blastocoel-like cavity as indicated by the arrowhead. Scale bar, 10 µm. m, Immunostaining of iBlastoids for GATA2, OCT4 and SOX2 (n=3). Scale bar, 20 µm. n, iBlastoid stained for GATA2, NANOG and SOX17 with ICM-like compartment-zoom showing SOX17 positive PE-like cells (n=2). o, iBlastoids stained for CDX2, OCT4 and GATA6 with ICM-like compartment-zoom showing CDX2 low and GATA6 positive PE-like cells (n=2). Scale bar for n-o=10 µm. p-q, Representative images of iBlastoids stained for F-actin and NANOG with EPI-like and TE-like cells zoom-in (q) highlighting their morphological differences (n=2). r, 3D segmentation of the iBlastoids in (p) based on F-actin (light blue) and NANOG (orange). Scale bar for p-r=10 µm for whole iBlastoids, 2 µm for ICM zoom. s, F-actin, OCT4 and KRT8 co-staining, n=2.
Figure 1:
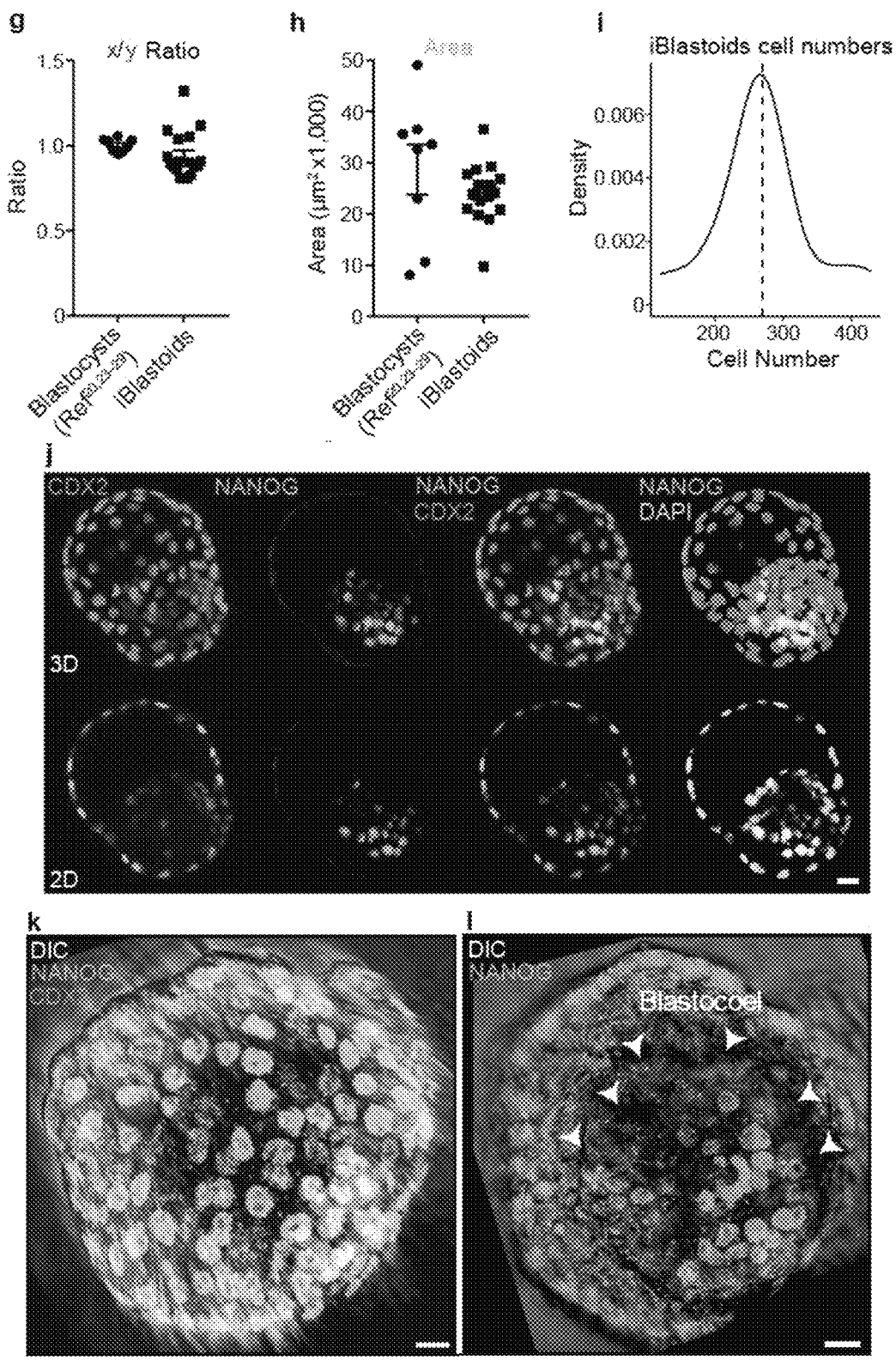
Figure 1:
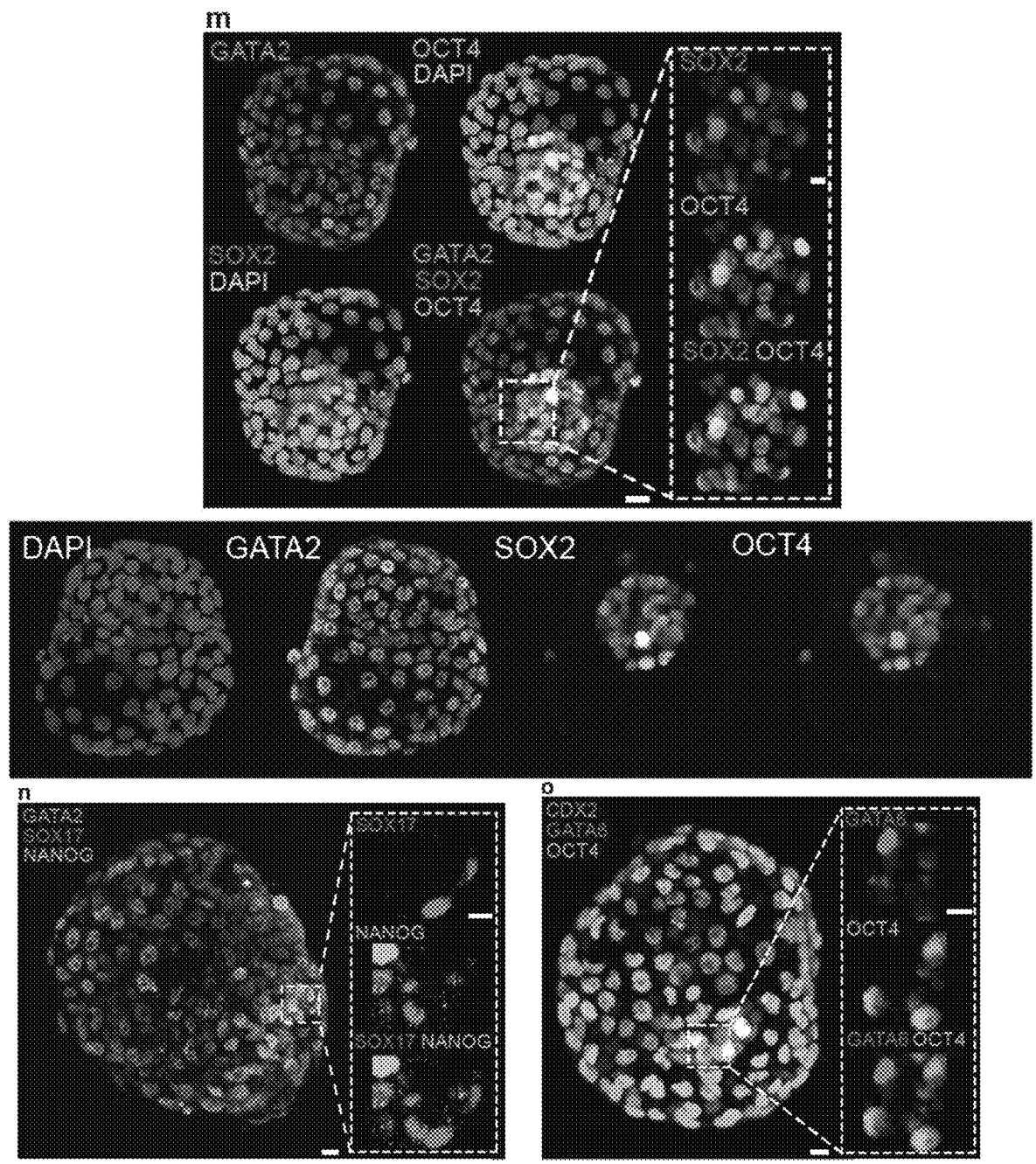
Figure 1:
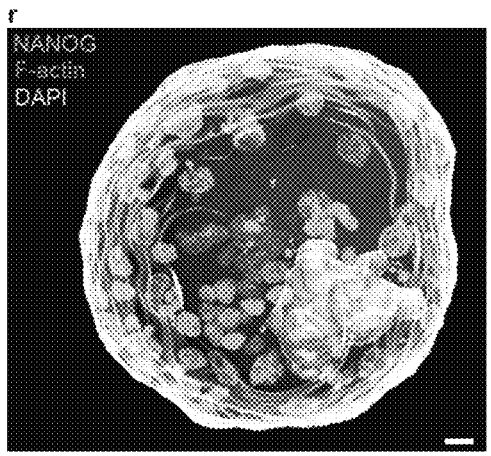
Figure 1:
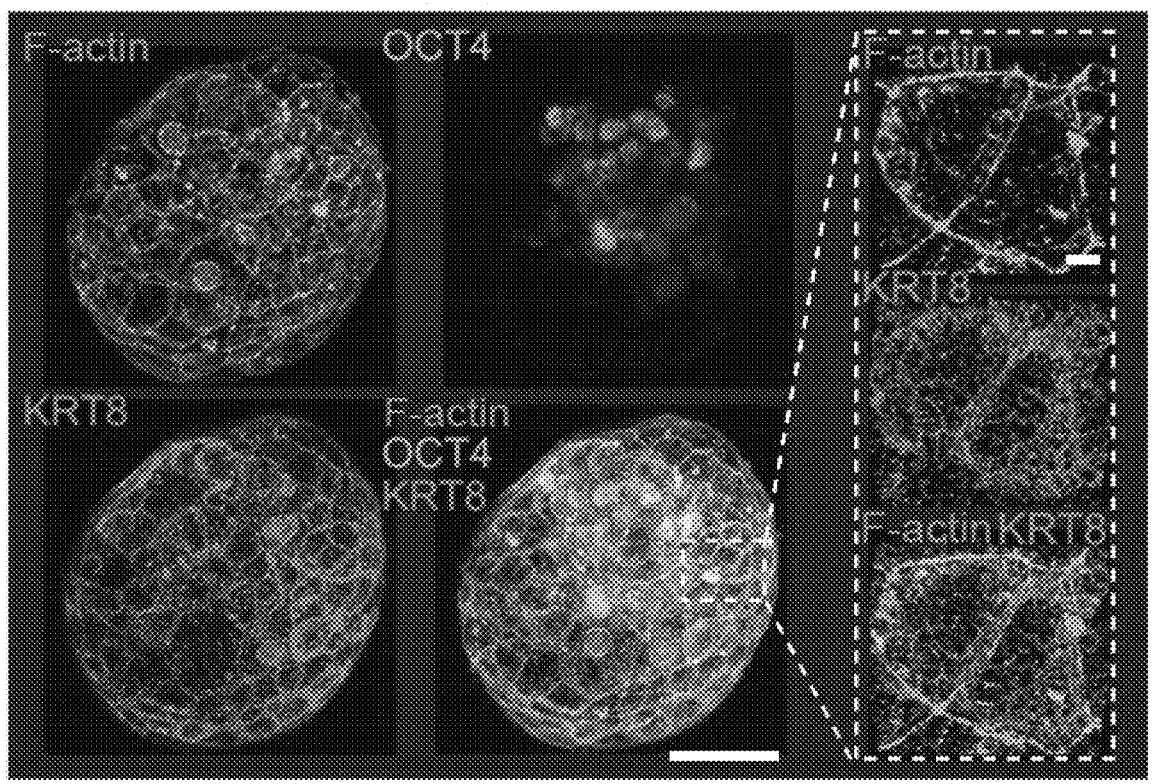

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

For purposes of interpreting this specification, terms used in the singular will also include the plural and vice versa.

The inventors have developed a novel culturing method which derives from the unexpected finding that human somatic cells (e.g. fibroblasts) can be directly reprogrammed into human multi-layered cellular structures or blastocyst-like structures (hereon also termed iBlastoids) that faithfully recapitulate the morphology, spatial interactions, and molecular makeup of the human blastocyst. Moreover, iBlastoids can mimic many aspects of early human embryonic development as validated by an in vitro attachment assay using human embryo attachment culture. Therefore, for the first time, the inventors report the generation of human iBlastoids, which represent a unique and experimentally tractable system to model and interrogate the complex cellular and molecular interactions that occur during early human embryogenesis.

Cells

The methods of the present invention include the use of reprogrammed somatic cells, wherein the cells exhibit epiblast (EPI), trophectoderm (TE), and primitive endoderm (PE) transcriptional signatures, to generate multi-layered cellular structures that resemble a blastocyst. It will be understood, as is further described herein, that in certain aspects, the methods of the invention may include an approach that commences with a somatic cell prior to reprogramming and prior to obtaining the reprogrammed somatic cells that exhibit epiblast (EPI), trophectoderm (TE), and primitive endoderm (PE) transcriptional signatures. In such cases, the methods will require a first step of commencing reprogramming of the somatic cells, in accordance with the methods further described herein. In alternative aspects, the methods of the invention may comprise starting with a reprogramming intermediate (e.g., a somatic cell that has been cultured in conditions to promote reprogramming towards a pluripotent state, but may or may not have completed reprogramming towards a fully pluripotent state, and as such is termed a reprogramming intermediate).

The somatic cells may be healthy somatic cells or diseased cells or may be derived from a healthy individual, or an individual having or being suspected of having one or more medical conditions or diseases. The somatic cell may also be from a deceased individual. The somatic cell may be an adult cell or a cell derived from an adult which displays one or more detectable characteristics of an adult or non-embryonic cell. The diseased somatic cell may be a cell displaying one or more detectable characteristics of a disease or condition.

The somatic cell for use in accordance with the present invention may be derived from an iPSC or other embryonic or adult stem cell or may be derived from a tissue explant from a subject. In particular examples, the somatic cell for use in accordance with the present invention comprises an inducible expression cassette encoding factors for reprogramming towards a dedifferentiated or pluripotent state, is differentiated from an iPSC or other embryonic or adult stem cell and is then dedifferentiated through inducing expression of the expression cassette.

The population of somatic cells will preferably comprise a population of cells that is homogenous (i.e., a population of somatic cells of the same type, such as a homogenous population of fibroblasts or a homogenous population of keratinocytes etc, wherein the population of cells does not comprise somatic cells of another cell type). It will be understood that in order to obtain such a homogenous cell population, it may be necessary to subject a population of cells (e.g., obtained from an individual), to culturing and other steps necessary to isolate the somatic cell of interest from a heterogeneous population of cells, so as to obtain a homogenous cell population.

In certain embodiments, the population of somatic cells used for reprogramming to cells that exhibit epiblast (EPI), trophectoderm (TE), and primitive endoderm (PE) transcriptional signatures, does not comprise embryonic stem cells, and preferably does not comprise extended (or expanded) pluripotent stem cells.

In preferred embodiments, the somatic cell is a fibroblast (preferably a dermal fibroblast), a keratinocyte (preferably epidermal keratinocyte), a monocyte or an endothelial cell or a mesenchymal stem cell. Preferably, the somatic cells for use in the methods of the present invention comprise only fibroblast cells. Alternatively, the somatic cells for use in the methods of the present invention may be peripheral blood mononuclear cells (PBMCs), preferably human. Alternatively, the somatic cells for use in the methods of the present invention may be mesenchymal stem cells (MSCs), preferably human. Morphological and gene expression markers characteristic of somatic cells will be known to the skilled person. Consequently, it will be within the purview of the skilled person to test for and observe reductions of markers characteristic of a somatic cell during the course of the methods of the present invention. In certain examples, where the somatic cell is a dermal fibroblast, morphological characteristics include a flattened mesenchymal morphology and markers include:CD13 (ANPEP), CD44, TWIST1 and ZEB1.

Keratinocyte markers include keratin1, keratin14 and involucrin and the cell morphology is cobblestone appearance. Endothelial cell markers include CD31 (Pe-CAM), VE-Cadherin and VEGFR2 and the cell morphology may be a capillary-like structure. Markers of an epithelial cell include cytokeratin 15 (CK15), cytokeratin 3 (CK3), involucrin and connexin 4. Preferably the observed morphology is a cobblestone appearance. Markers of haemaotopoietic stem cells may comprise CD45 (pan haematopoietic marker), CD19/20 (B-cell markers), CD14/15 (myeloid), CD34 (progenitor/SC markers), CD90 (SC). Markers of mesenchymal stem cells comprise: CD13, CD29, CD90, $CD10^5$, CD10, CD45.

As used herein, the term "stem cell" refers to a cell which is not terminally differentiated, i.e., it is capable of differentiating into other cell types having a more particular, specialised function. The term encompasses embryonic stem cells, fetal stem cells, adult stem cells or committed/progenitor cells.

As used herein, a "somatic cell" refers to a terminally differentiated cell. As used herein, the term "somatic cell" refers to any cell forming the body of an organism, as opposed to germline cells. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated stem cells—is a somatic cell: internal organs, skin, bones, blood, and connective tissue are all made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro. The somatic cells may be immortalized to provide an unlimited supply of cells, for example, by increasing the level of telomerase reverse transcriptase (TERT). For example, the level of TERT can be increased by increasing the transcription of TERT from the endogenous gene, or by introducing a transgene through any gene delivery method or system.

Differentiated somatic cells, including cells from a fetal, newborn, juvenile or adult primate, including human, individual, are suitable somatic cells for use in the methods of the invention. Suitable somatic cells include, but are not limited to, bone marrow cells, epithelial cells, endothelial cells, fibroblast cells, peripheral blood mononuclear cells, hematopoietic cells, keratinocytes, hepatic cells, intestinal cells, mesenchymal cells, myeloid precursor cells and spleen cells. Alternatively, the somatic cells can be cells that can themselves proliferate and differentiate into other types of cells, including blood stem cells, muscle/bone stem cells, brain stem cells and liver stem cells. Suitable somatic cells are receptive, or can be made receptive using methods generally known in the scientific literature, to uptake of transcription factors including genetic material encoding the transcription factors. Uptake-enhancing methods can vary depending on the cell type and expression system. Exemplary conditions used to prepare receptive somatic cells having suitable transduction efficiency are well-known by those of ordinary skill in the art. The starting somatic cells can have a doubling time of about twenty-four hours.

The term "isolated cell" as used herein refers to a cell that has been removed from an organism in which it was originally found or a descendant of such a cell. Optionally the cell has been cultured in vitro, e.g., in the presence of other cells. Optionally the cell is later introduced into a second organism or re-introduced into the organism from which it (or the cell from which it is descended) was isolated.

Multi-Layered Cellular Structure or Blastocyst-Like Structures

The present invention provides multi-layered cellular structure or blastocyst-like structures, or compositions comprising the same. Preferably the multi-layered cellular structure is obtained or obtainable by any method as described herein. Such multi-layered cellular structures or blastocyst-like structures may also be termed in vitro-derived or in vitro-generated blastoids or blastocyst-like structures or "iBlastoids".

It will be appreciated that the multi-layered cellular structures or blastocyst-like structures of the invention can be characterised by a number of structural and functional features, such as those further described below. Importantly, and as described further below, while the structures of the invention exhibit the main morphological features of human blastocysts at E5-7, the structures are also characterised by features that are different from naturally occurring human blastocysts, such as the absence of a zona pellucida, which exists in naturally occurring blastocysts, but not in the structures of the present invention. Thus the in vitro-derived or generated blastocyst structures of the invention can clearly be distinguished from naturally occurring blastocysts.

In any aspect, the multi-layered cellular structure or blastocyst-like structure comprises an inner cell layer and an outer cell layer, the inner cell layer comprises cells that exhibit one or more characteristics of cell of the epiblast and/or the primitive endoderm lineage, and the outer cell layer comprises cells that exhibit one or more characteristics of a cell of the trophectoderm. Preferably the characteristic may be determined by analysis of cell morphology, gene expression profiles, activity assay, protein expression profile, surface marker profile, differentiation ability or a combination thereof. Examples of characteristics or markers include those that are described herein and those known to the skilled person. The multi-layered cellular structure or blastocyst-like structure may or may not have a cavity/blastocoel.

In any aspect, the inner cell layer further comprises a cluster of cells that exhibit one or more characteristics of the PE. Preferably the cells that exhibit one or more characteristics of the PE are, or are predominantly, peripheral to the cells that exhibit one or more characteristics of a cell of the epiblast.

In any aspect, the characteristic of a TE cell is the presence of one or more of the markers CDX2 and GATA2.

In any aspect, the characteristic of a TE cell is a flattened or elongated epithelial morphology.

In any aspect, the characteristic of a PE cell is the presence of the marker SOX17 or GATA6.

TABLE 1

EPI, TE and PE transcriptional signatures

| Lineage | Marker (gene that is expressed) |
|---|---|
| EPI | ACE, ARGFX, ASH2L, BTLA, CASP8, CFLAR, CPT1A, DPPA2, DPPA4, DPPA5, FOXD3-AS1, HEY2, ITFG3, KLF17, LAPTM4B, LDLRAP1, MT1X, NGEF, PBX3, PLA2G4F, POU5F1, PRDM14, PSORS1C2, SERPINB6, SH3PXD2A, SHPK, SLC25A12, SOX2, SUSD2, TNFRSF8, UBTDI, AARS2, ABHD12B, ANKRD45, APOBEC3C, APOBEC3D, ATP8B2, BCOR, CAMKV, CAPG, CBFA2T2, CCDC80, CDHR1, CHST2, CREBL2, CXCL12, DND1, DOCK6, ESRG, ETV1, ETV4, FAM124A, FAM46B, FBP1, FGF4, GDF3, GGT1, GK, GPRC5C, GUCA1A, IFITM1, IGSF1, L23A, LIM2, LINC01108, LRP4, MAN1C1 , MAP4K1, MEG3, MIAT, MUC4, NANOG, NLRP9, NODAL, NRBP2, PIM2, PITPNM2, PRUNE2, RASD1, RRAD, SAT1, SEPT6, SERINC5, SLC16A9, ST6GALNAC3, TBC1D16, TDGF1, TDGF1P3, TRIM56, UNC5B, UPP1, USP28, UTF1, VASH2, VENTX, VSNL1, WNT3, ZIC3, ZSCAN10, ZYG11A |
| PE | BMP6, CELA3A, CELA3B, DEPDC7, DPP4, DYNLT3, FN1, GATA6, GCNT3, HNF4A, OTX2, P4HA1, RGS5, SERPINE2, ABHD6, ADD3, ALDH1A1, AMBN, AMOTL1, APOA1, APOA2, BMP2, CACHD1, CADM1, CAMK2D, COAT1, CDH11, CDH2, CERS6, CMBL, CNIH3, COL4A1, COL4A2, CPN1, CTSE, DENND2C, DUSP4, EDEM1, FLRT3, FOXA2, FRMD6, FRZB, FST, GATA4, GNA13, GPC3, HMGCR, HNF1B, ID2, IGF1, KCNJ16, KIFAP3, KIT, LEPRE1, LINC00261, LOC101929344, LOC101929767, LOC400043, LRRC16A, MAP2K6, MARCKS, MYL4, NID1, NID2, NOG, PAPSS1, PDGFRA, PDPN, PGM1, PHLDB2, PIK3R1, PITX2, POMC, PROP, PROS1, PTK2B, RNASE1, ROBO1, RSPO3, SALL1, SLCO2A1, SMAD9, SP8, TMEM123, TMEM88, TRIM2, VIL1, VWA5A, ANKRD1, CALCR, COL18A1, FAM198B, FGG, GCKR, GPR161, HABP2, ITIH5, MTTP, SYT13, TNIP3, SOX17 |
| TE | FRMD4B, GLIPR2, HSPB11, MYC, MYLPF, OSBPL6, PDLIM1, PIP5K1B, SYBU, TMEM171, VAMP8, ABCG2, ADAM15, ADK, ALPP, ANKRD6, ANXA6, ARHGAP23, ARHGEF26, ATP8B1, BASP1, C4BPB, CAST, CD24, CD53, CITED4, CLDN3, DAB2, DNAJC6, ELOVL6, EMP2, ENPEP, FABP3, FAM101B, FASN, FBXL18, FHL2, GAB2, GALNT10, GATA2, GM2A, GREB1L, HP1, JDP2, KRT19, LAD1, LRP2, LRRFIP1, MYCT1, MYO6, NIM1K, NPC2, OLFML1, PALLD, PLAC8, PPME1, PPT1, PWWP2B, S100A6, SH3GL3, SLC19A3, SLC28A3, SLC34A2, SLC7A2, SLC7A4, TACSTD2, TAGLN2, TCF7L1, TEAD1, TFRC, TMEM106C, TMPRSS13, TMPRSS2, TSPAN15, WNT7A, ACTN1, ATP6V0A4, ATP6V1B1, CLDN10, CLDN4, CYP26A1, EFNA1, FOLR1, GATA3, GPRC5A, GRHL2, GYLTL1B, KRT18, KRT8, MYOF, PDGFA, PRSS8, PTGES, RAB25, S100A16, SLC12A3, SLC7A5, SUN3, TET2, TGFBR3 |

In any aspect, the inner cell layer is an inner cell mass-like tissue that behaves essentially as a naturally-formed inner cell mass.

In any aspect, the outer cell layer is a trophectoderm-like tissue that behaves essentially as a naturally-formed trophectoderm.

The multi-layered cellular structure or blastocyst-like structure may also be referred to as an artificial blastocyst comprising a trophectoderm-like tissue that surrounds a blastocoel and an inner cell mass-like tissue.

In any aspect, the population of cells exhibiting transcriptional signatures of the epiblast (EPI), trophectoderm (TE), and/or primitive endoderm (PE) lineages preferably exhibits transcriptional signature of each of the epiblast (EPI), trophectoderm (TE), and primitive endoderm (PE) lineages.

In any aspect, the characteristic of an EPI cell is the presence of any one or more of the markers NANOG, OCT4 (also known as POU5F1) or SOX2. In one embodiment, more cells in the multi-layered cellular structure or blastocyst-like structure express OCT4 than NANOG.

In any aspect, the characteristic of an EPI cell is the morphology of a rounded columnar appearance.

In any aspect, the multi-layered cellular structure or blastocyst-like structure may further comprises GATA6 positive cells (optionally with low or weak CDX2 staining) neighbouring OCT4 positive cells.

In any aspect, the multi-layered cellular structure or blastocyst-like structure exhibits the main morphological features of human blastocysts at E5-7, preferably E6-7. The main morphological features of human blastocysts at E5-7, and E6-7 are known to the skilled person. Such features may include a spherical or predominantly spherical layered cell aggregate or structure comprising at least two radially positioned layers, and comprising an inner cell layer (as defined herein) and an outer cell layer (as defined herein) with a zona pellucida and a fluid-filled cavity, called the blastocoel. The blastocyst has a diameter of approximately 0.1-0.2 mm and typically comprises about 200-300 cells. Generally the cells that exhibit one or more characteristics of cell of the epiblast and/or the primitive endoderm lineage are present in a single cluster located on the inside of the aggregate or structure, while that exhibit one or more characteristics of a cell of the trophectoderm are present on the outside.

Further characteristics and features of human blastocysts are described for example, in Blakeley, P. et al. (2015) Development 142, 3613; Petropoulos, S. et al. (2016) Cell 165, 1012-1026; Shahbazi, M. N. et al. (2016) Nat. Cell Biol. 18, 700-708; Xiang, L. et al. (2020) Nature 577, 537-542; Qin, H. et al. (2016) Cell Rep. 14, 2301-2312; Liu, L. et al. (2019) Nat. Commun. 10, 364; Durruthy-Durruthy, J. et al. (2016) Dev. Cell 38, 100-115; Fogarty, N. M. E. et al. (2017) Nature 550, 67-73.

Further, the multi-layered cellular structure or blastocyst-like structure may also comprise cells that exhibit one or more characteristics of cell of the epiblast, primitive endoderm and trophectoderm, where those cells adopt the same or similar relative spatial arrangement as epiblast, primitive endoderm and trophectoderm cells, respectively, in human blastocysts at E5-7, preferably E6-7. As used herein, "the same or similar relative spatial arrangement" with respect to human blastocysts shall be taken to mean having at least two radially positioned layers, and comprising an inner cell layer (as defined herein) and an outer cell layer (as defined herein). There may be more than two cell layers but it generally holds that the cells that exhibit one or more characteristics of cell of the epiblast and/or the primitive endoderm lineage are present in a single cluster located on the inside of the aggregate or structure, while those that exhibit one or more characteristics of a cell of the trophectoderm are present on the outside. In other words, the outer layer of cells in the structure are typically cells of the TE (and express TE markers such as CDX2 and GATA2), while cells indicative of the epiblast (and which express markers such as NANOG and OXT4 and SOX2) are found in the ICM-like compartments within the structure.

In any aspect, the multi-layered cellular structure or blastocyst-like structure also comprises a cell free cavity, or blastocoel-like cavity. The multi-layered cellular structure or blastocyst-like structure may undergo cavitation, thereby allowing the blastocoel to form. Following the formation of the blastocoel-like cavity, the inner mass-like tissue may position itself in one portion of the inner cavity, while the rest of the cavity is filled with fluid.

The multi-layered cellular structure or blastocyst-like structures produced by the methods of the present invention generally differ from naturally arising human blastocysts in that the structures of the present invention do not form or comprise a zona pellucida.

As used herein, the term "zona pellucida" refers to the glycoprotein layer that surrounds the plasma membrane of mammalian oocytes. Following fertilisation of an oocyte, the zona pellucida remains intact and thus, naturally occurring blastocysts comprise a zona pellucida up to around five days following fertilisation, at which time the blastocysts performs so-called "zona hatching" wherein the zona pellucida degenerates and decomposes as part of implantation.

The structures of the invention may also be differentiated from naturally occurring blastocysts in that the structures may comprise cells having an overall gene signature not found in cells of a blastocyst which is typically a mixed gene expression profile such that the cells express genes that are characteristic of both the PE and TE, both the PE and EPI, both the TE and EPI, or a combination of the PE, TE and EPI.

In other words, some cells in the structures of the invention may have mixed transcription signatures that are characteristic of more than one lineage. In other words, one or more individual cells may have mixed transcription signatures that are characteristic of more than one lineage The transcriptional signatures associated with each lineage are described further herein, for example above at [117]-[122] and Table 1.

In any aspect, the multi-layered cellular structure or blastocyst-like structure has an x- and y-axis diameter, x:y aspect ratio and/or projection area of a comparable size to previously published measurements of human blastocysts at embryonic day 5-7 (E5-7) post-fertilization. For example, the x- and/or y-axis diameter of the multi-layered cellular structure or blastocyst-like structure is from about 100 to about 300 µm. Preferably, the x/y axis ratio is about 1. The projection area of the multi-layered cellular structure or blastocyst-like structure is about 5,000 to about 10,000 µm$^2$, about 10,000 to about 40,000 µm$^2$, about 40,000 µm$^2$ to about 60,000 µm$^2$, preferably about 20,000 to about 40,000 µm$^2$.

As used herein, a "comparable" x- and y-axis diameter or x:y aspect ratio to previously published measurements of human blastocysts at E5-7 may comprise x- and y-axis diameter or x:y aspect ratios that are between about 50% to 200% of the previously published measurements, preferably at least about 50%, at least about 60%, at least about 70%, at least about 80%, at least about 90%, at least about 100%, at least about 110%, at least about 1200%, at least about 120%, at least about 130%, at least about 140%, at least about 150%, at least about 160%, at least about 170%, at least about 180%, at least about 190% or at least about 200% of previously published measurements.

As used herein, a "comparable" projection area to previously published measurements of human blastocysts at E5-7 may comprise projection areas that are between about 50% to 200% of the previously published measurements for human blastocysts. Preferably, comparable projection areas comprise areas that are at least about 50%, at least about 60%, at least about 70%, at least about 80%, at least about 90%, at least about 100%, at least about 110%, at least about 1200%, at least about 120%, at least about 130%, at least about 140%, at least about 150%, at least about 160%, at least about 170%, at least about 180%, at least about 190% or at least about 200% of values ranging from 5,000 to about 40,000 µm$^2$. In other words, a comparable projection area may be an area that is between about 5,000 to about 10,000 µm$^2$, about 10,000 to about 40,000 µm$^2$, about 40,000 µm$^2$ to about 60,000 µm$^2$, preferably about 20,000 to about 40,000 µm$^2$.

In the context of the invention, the multi-layered cellular structure or blastocyst-like structure is a layered cell aggregate or structure comprising at least two radially positioned layers. Preferably, it is a spherical, or predominantly spherical cell aggregate or structure comprising an inner cell layer (as defined herein) and an outer cell layer (as defined herein). There may be more than two cell layers but it generally holds that the cells that exhibit one or more characteristics of cell of the epiblast and/or the primitive endoderm lineage are present in a single cluster located on the inside of the aggregate or structure, while that exhibit one or more characteristics of a cell of the trophectoderm are present on the outside.

In any aspect, the multi-layered cellular structure or blastocyst-like structure comprises about 100 to 400 total cells.

In preferred embodiments, the present invention provides an in vitro-derived or generated blastocyst or blastoid structure (i.e., a multi-layered cellular structure or blastocyst-like structure) having 1, 2, 3, 4, 5, 6, 7, 8, 9, 10, 11, 12 or 13 of the following characteristics:

a spherical or predominantly spherical layered cell aggregate or structure comprising at least two radially positioned layers, and comprising an inner cell layer and an outer layer with no zona pellucida;

the inner cell layer comprising cells that exhibit one or more characteristics of cell of the epiblast (EPI) the characteristic of an EPI cell being the presence of any one or more of the markers NANOG, OCT4 (also known as POU5F1) or SOX2 and a rounded columnar appearance;

the inner cell layer also comprising a cluster of cells that exhibit one or more characteristics of the primitive endoderm (PE) lineage, wherein the cells that exhibit one or more characteristics of the PE are, or are predominantly, peripheral to the cells that exhibit one or more characteristics of a cell of the epiblast; the characteristic of a PE cell being the presence of the marker SOX17 or GATA6.

the outer cell layer comprising cells that exhibit one or more characteristics of a cell of the trophectoderm (TE), the characteristic of a TE cell being the presence of one or more of the markers CDX2 and GATA2 and a flattened or elongated epithelial morphology;

a diameter of approximately 0.1-0.2 mm;

about 100-400 cells;

wherein more cells in the multi-layered cellular structure or blastocyst-like structure express OCT4 than NANOG;

GATA6 positive cells (optionally with low or weak CDX2 staining) neighbouring OCT4 positive cells;

an x- and/or y-axis diameter of the multi-layered cellular structure or blastocyst-like structure is from about 100 to about 300 μm;

an x/y axis ratio of about 1;

a projection area of about 5,000 to about 10,000 μm$^2$, about 10,000 to about 40,000 μm$^2$, about 40,000 μm$^2$ to about 60,000 μm$^2$, preferably about 20,000 to about 40,000 μm$^2$;

optionally, a fluid-filled cavity, called the blastocoel; and optionally wherein the cells that exhibit one or more characteristics of cell of the epiblast and/or the primitive endoderm lineage are present in a single cluster located on the inside of the aggregate or structure, while those that exhibit one or more characteristics of a cell of the trophectoderm are present on the outside.

The multi-layered cellular structures or blastocyst-like structures of the invention and/or obtained according to the methods of the present invention typically exhibit characteristics that mimic many aspects of early human embryonic development. In certain embodiments, the structures mimic the characteristics of human embryos in in vitro attachment assays, which may be utilised to study embryo implantation. For example, when cultured in IVC1 media (as defined herein) for 1 day and subsequently cultured in IVC2 media (as defined herein) from day 2 to day 4.5, the multi-layered cellular structure or blastocyst-like structure may exhibit one of more of the following:

i) increases in size, flattens and progresses to form an outgrowth;

j) an increase in the number of NANOG and OCT4/SOX2 positive cells;

k) a spread of CDX2 and GATA2 positive cells;

l) SOX17 and GATA6 positive cells localize to the perimeter of the NANOG or OCT4 positive cells;

m) expression of keratin KRT7 or other trophoblast marker in the outer cell layer or cells exhibiting at least one characteristic of a TE cell;

n) presence of cells which morphologically resemble syncytiotrophoblast (ST) and extravillous cytotrophoblasts (EVT) (e.g. ST and EVT-like cells, respectively), for example a multi-nucleated phenotype and spindle-like morphology;

o) presence of cells expressing hCG (an exemplary ST marker), and MMP2 (an exemplary EVT marker); and p) presence of cells exhibiting upregulation of the ST marker CSH1 and EVT marker ITGA1.

It will be appreciated that an "increase" as used herein, whether in relation to an increase in size or an increase in number of cells positive for a particular marker, refers to a change of greater than about 5%. As such an "increase", in the context of size of a multi-layered cellular or blastocysts-like structure, will be understood to include an increase in size of at least 5%, at least 10%, at least 20%, at least 30%, at least 40%, at least 50%, at least 60%, at least 70%, at least 80%, at least 90%, at least 100%, at least 150%, at least 200%, at least 250%, at least 300% or more, compared to the size of the structure prior to being cultured in an in vitro-attachment assay (such as described herein. Similarly, an "increase" in the number of cells positive for particular markers (such as NANOG and OCT4/SOX2) may be a an increase in the number of cells that is at least %, at least 10%, at least 20%, at least 30%, at least 40%, at least 50%, at least 60%, at least 70%, at least 80%, at least 90%, at least 100%, at least 150%, at least 200%, at least 250%, at least 300% or more, compared to the number of marker positive cells in the structure prior to being cultured in an in vitro-attachment assay It will be appreciated that in accordance with the first aspect of the invention, the multi-layered cellular structure or blastocyst-like structure is obtained from a population of reprogrammed somatic cells (preferably reprogrammed human somatic cells), exhibiting epiblast (EPI), trophectoderm (TE), and primitive endoderm (PE) transcriptional signatures. The multi-layered cellular structure or blastocyst-like structure may alternatively be generated by assembly of an iPSC and iTSC, or population of iPSCs and iTSCs. For example, a method of producing a multi-layered cellular structure comprises:

culturing an iPSC and iTSC cell under conditions that allow aggregation to obtain a multi-layered cellular structure;

thereby producing a multi-layered cellular structure.

Alternatively, there is a method of producing an in vitro-derived blastocyst-like structure, the method comprising:

culturing an iPSC and iTSC cell under conditions that allow aggregation to obtain a blastocyst-like structure;

thereby producing a blastocyst-like structure.

Methods for generating iPSCs and iTSCs are known in the art. Exemplary methods for generating iPSCs are described for example in: Takahashi et al., (2007) Cell, 131: 861-872, WO 2017/219232, WO 2014/200114, WO 2014/065435, WO 2019/073055, Liu et al., (2017) Nat. Methods, 14: 1055-1062; the entire contents of which are hereby incorporated by reference in their entirety. Exemplary methods for generating iTSCs are described in Liu et al., (2020) Nature, 586: 101-107, the contents of which are also incorporated herein by reference.

In one embodiment, the iPSC and iTSC may be co-cultured in any culture vessel described herein, for example, a 24-well AggreWell™400 plate. Preferably, the cells are cultured in any culture medium for promoting cells (e.g. a blastocyst promoting medium or iBlastoid medium) to exhibit at least one characteristic of a blastocyst-like structure as described herein. Preferably, the culture medium is an iBlastoid medium as shown in Table 3a.

Preferably, the iPSC and iTSC are co-cultured in the same well at respective 1:2.5 ratio with a total number of $1.2 \times 10^5$ cells per well.

In another aspect, the present invention also provides a multi-layered cellular structure or blastocyst-like structure produced by any method as described herein.

Reprogramming

Various methods for reprogramming a somatic cell towards a dedifferentiated or pluripotent state are known in the art. Reprogramming of somatic cells typically involves the expression of reprogramming factors (including transcription factors), followed by culture in particular conditions for promoting the loss of markers of differentiation, and the gain of pluripotency/plasticity markers.

In accordance with the methods of the present invention, somatic cells are reprogrammed towards a dedifferentiated or pluripotent state, in order to obtain a population of cells exhibiting transcriptional signatures of the EPI, TE or PE lineages, prior to being subjected to culturing conditions for promoting formation of a multi-layered cellular structure or blastocyst-like structure. Accordingly, it will be appreciated that the population of cells comprise reprogramming intermediates at the time of being subjected to culturing conditions for promoting formation of a multi-layered cellular structure or blastocyst-like structure. The reprogramming intermediates exhibit transcriptional signatures of the EPI, TE and/or PE lineages. Preferably the population of intermediates exhibits transcriptional signatures of all three of the EPI, TE and PE lineages.

Figure 2:
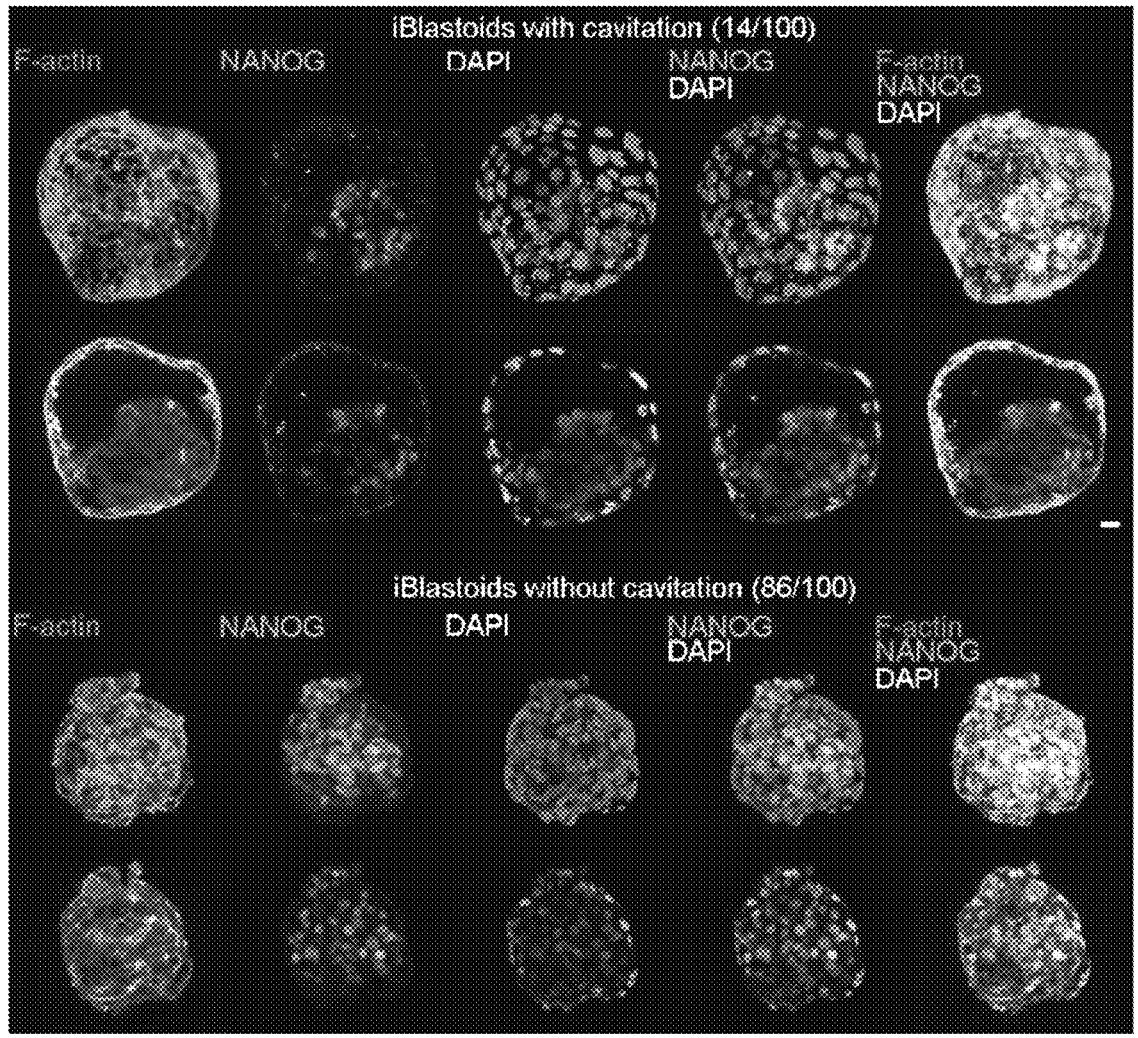
FIG. 2. Generation and characterization of iBlastoids. a, scRNA-seq analysis of day 21 reprogramming intermediates showing the presence of EPI, TE, and PE-like populations. b, Time-course phase-contrast images of iBlastoid formation (n=5). Scale bar, 100 µm. c, Quantification of iBlastoids with cavity formation (n=100). Scale bar, 20 µm. d, Representative phase-contrast images of the refractory HDFa adhering to the microwell edges during iBlastoid formation, which propagated in fibroblast medium with a classic fibroblast morphology (n=2). Scale bar, 100 µm. e, 3D and 2D representation of iBlastoids stained for CDX2 and NANOG (n=5). Scale bar, 20 µm. f, iBlastoid stained for GATA2, NANOG, and SOX17 (n=2). g, iBlastoids stained for CDX2, OCT4, and GATA6 (n=2). Scale bar, 20 µm for f-g. h, Quantification of different existing cell populations in day 21 reprogrammed cells; n=3. *i*, Assessment criteria used for scoring of iBlastoids. *j*, Phase-contrast images of iBlastoids included for scoring assessment, n=24. Scale bar, 100 μm. *k*, Average grade of ICM and TE for iBlastoids in (i) according to (h), n=24.
Figure 2:
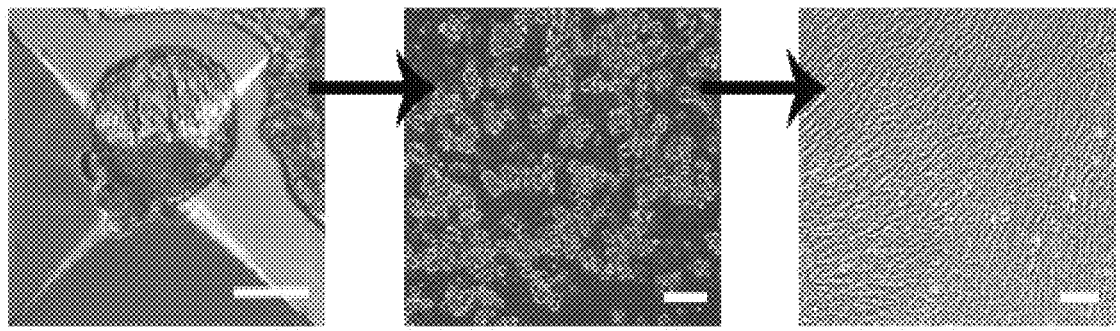
Figure 2:
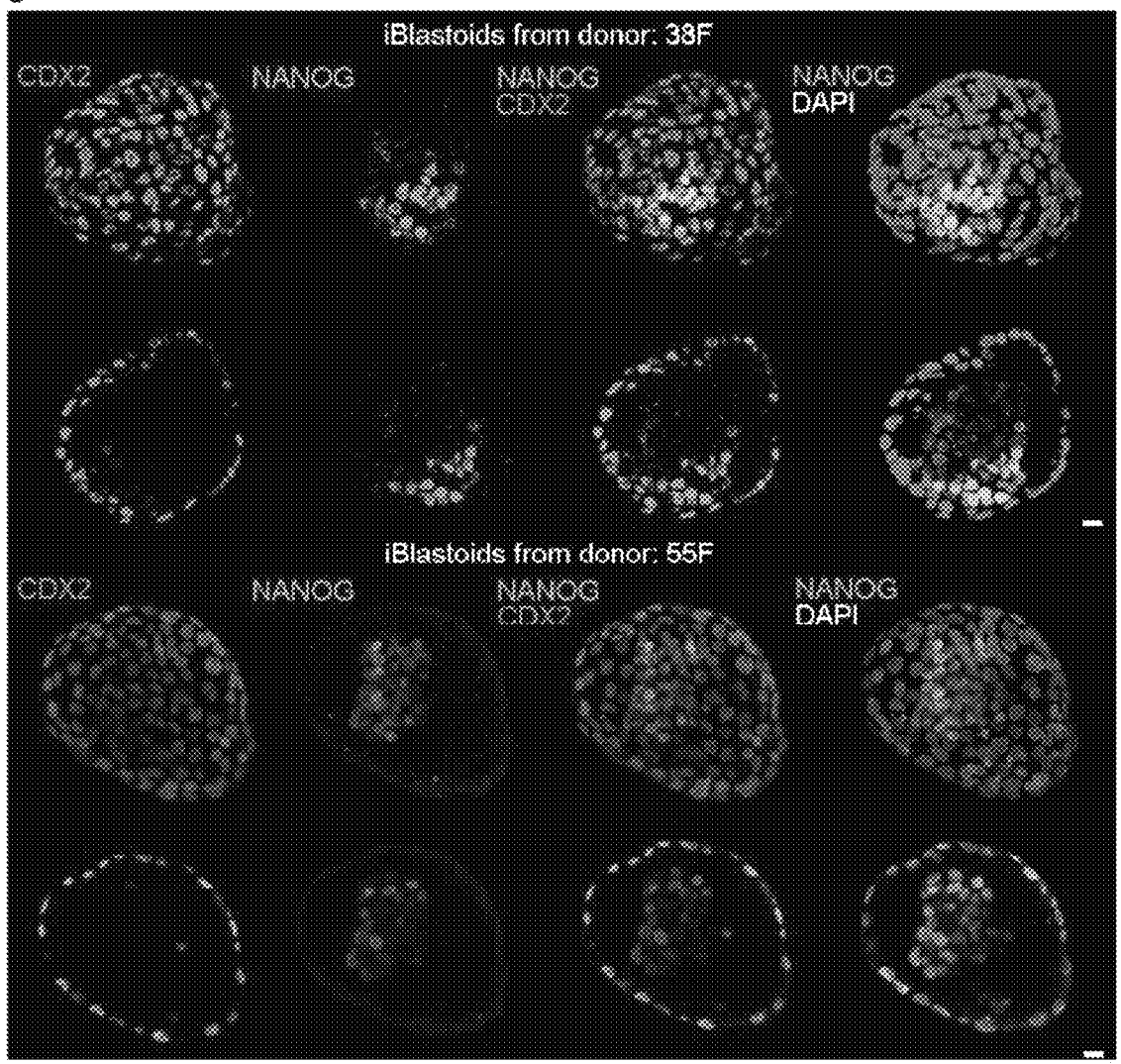
Figure 2:
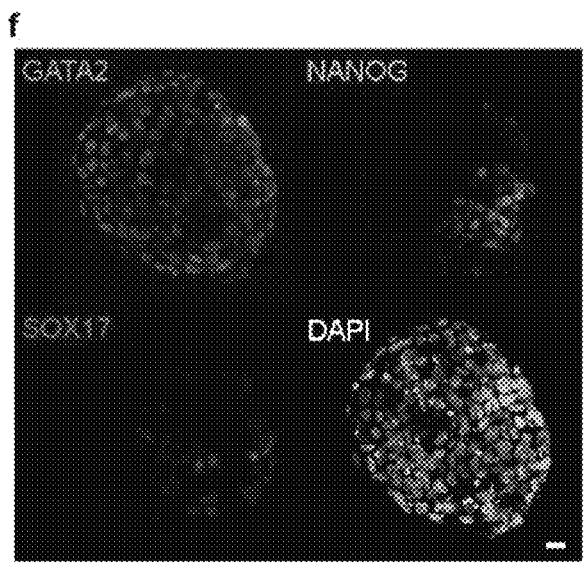
Figure 2:
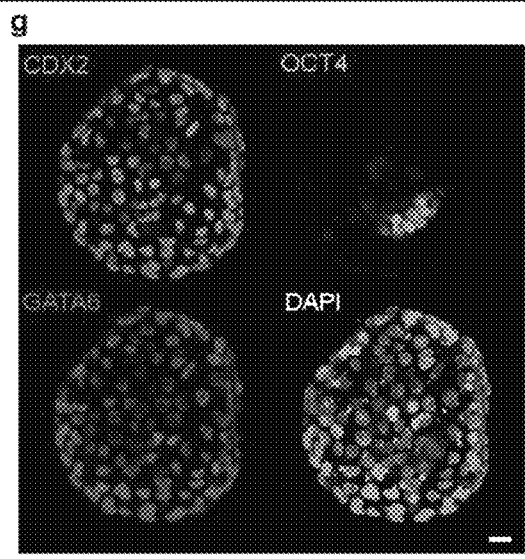
Figure 2:
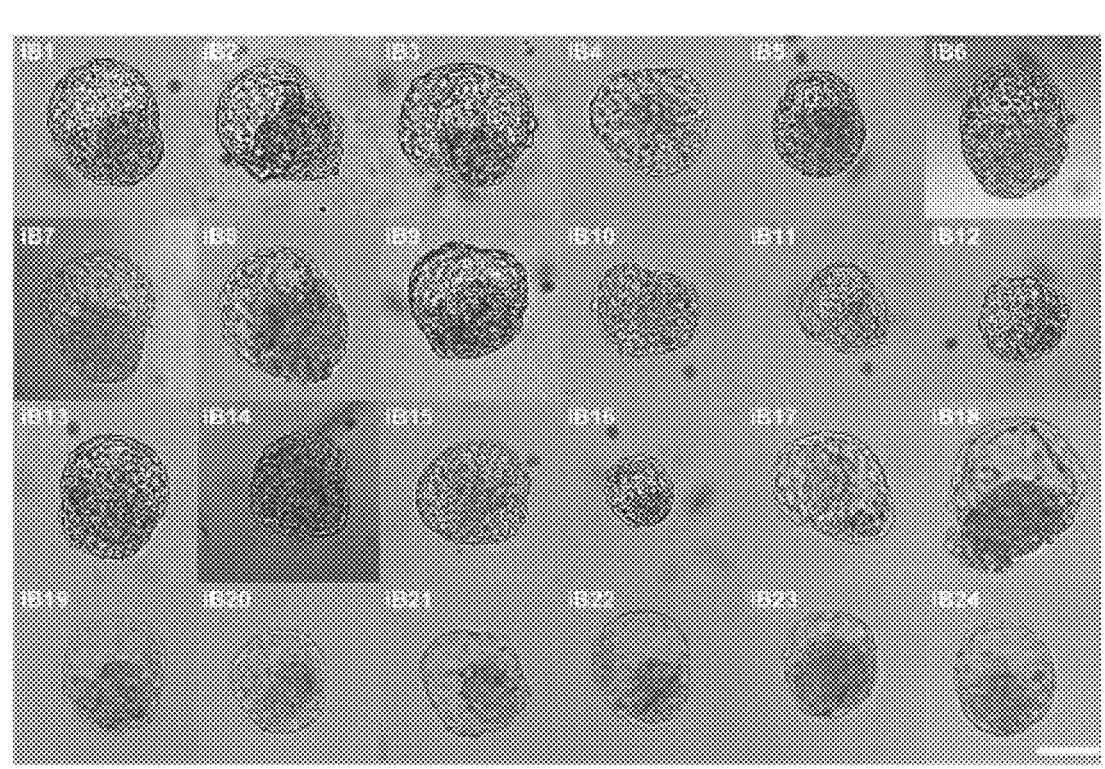
Figure 2:
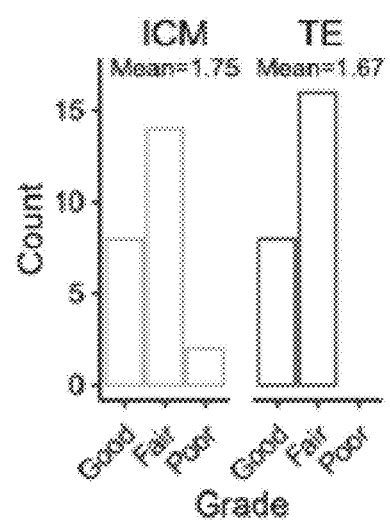

A population of reprogramming intermediates made according to the present invention may also be characterised by reference to the proportion of different cell populations staining positive or negative for markers OCT4, GATA6 and CDX2, as show in FIG. 2h herein.

In any aspect, a population of cells exhibiting transcriptional signatures of the EPI, TE or PE lineage comprises a population of cells expressing at least one of the markers listed in Table 1 herein.

Preferably, a transcriptional signature of the EPI lineage comprises expression of at least 2, at least 3, at least 4, at least 5, at least 10, at least 15, at least 20, at least 30, at least 40, at least 50, at least 60, at least 70 or more or all of the markers of the EPI lineage as listed in Table 1 herein. More preferably, a transcriptional signature of the TE lineage comprises expression of at least 2, at least 3, at least 4, at least 5, at least 10, at least 15, at least 20, at least 30, at least 40, at least 50, at least 60, at least 70 or more or all of the markers of the TE lineage as listed in Table 1 herein. More preferably, a transcriptional signature of the PE lineage comprises expression of at least 2, at least 3, at least 4, at least 5, at least 10, at least 15, at least 20, at least 30, at least 40, at least 50, at least 60, at least 70 or more or all of the markers of the PE lineage as listed in Table 1 herein.

In particular preferred embodiments, a transcriptional signature of the EPI lineage comprises expression of any one, two, three, four, five, six, seven, eight or nine, or of all of the markers: ARGFX, NANOG, GDF3, SUSD2, DPPA5, POU5F1, UTF1, TDGF1, PDLIM1 and USP28; a transcriptional signature of the TE lineage comprises expression of any one, two, three, four, five, six, seven, eight or nine, or of all of the markers: KRT18, KRT8, NODAL, UPP1, TAGLN2, KRT19, SLC7A5, FAM101B, CDX2, and GATA2; and a transcriptional signature of the PE lineage is expression of any one, two, three, four, five, six, seven, eight or nine, or of all of the markers: PALLD, FST, NOG, CLDN10, SERPINB6, MIAT, CHST2, VSNL1, MT1X, PDPN, SOX17, and GATA6.

Examples of suitable methods for reprogramming somatic cells are replete in the art, and are exemplified in WO 2009/101407, WO 2014/200030, WO 2015/056804, WO 2014/200114, WO 2014/065435, WO 2013/176233, WO 2012/060473, WO 2012/036299, WO 2011/158967, WO 2011/055851, WO 2011/037270, WO 2011/090221, the contents of which are hereby incorporated by reference. Typically, such methods comprise increasing the amount one or more factors or agents, that are capable of (or for the purposes of) reprogramming the cell towards a pluripotent state, in a starting cell type (or source cell).

In certain embodiments, the factors or agents for reprogramming the somatic cell, or which are capable of reprogramming the somatic cell are transcription factors. Alternatively, the factors or agents indirectly increase the levels of one or more transcription factors in a cell, as further described herein. Particularly preferred transcription factors, and nucleic acid sequences thereof, that may be used to reprogram a somatic cell (e.g., a fibroblast) in accordance with the methods of the invention are shown in Table 2. In accordance with the present invention, it will be understood that one or more, two or more, three or more, four or more, five or more, or all 6 of the transcription factors listed in Table 2 may be used in order to reprogram a somatic cell. It will be understood however that the present invention is not limited to the use of the transcription factors recited in Table 2 in order to reprogram a somatic cell.

The transcription factors and other protein factors referred to herein are referred to by the HUGO Gene Nomenclature Committee (HGNC) Symbol. Table 2 provides exemplary Ensemble Gene ID and Uniprot IDs for the transcription factors recited herein. The nucleotide sequences are derived from the Ensembl database (Flicek et al. (2014). Nucleic Acids Research Volume 42, Issue D1. Pp. D749-D755) version 83. Also contemplated for use in the invention is any variant, homolog, ortholog or paralog of a transcription factor referred to herein.

In certain embodiments, only a single cell type is subjected to reprogramming in accordance with the methods of the invention. In other words, preferably the population of cells that is subjected to reprogramming, is a homogenous or substantially homogenous population of cells. For example preferably, the population of cells is comprised only of, or predominantly comprised of fibroblasts, or of keratinocytes, or of any other somatic cell type as described herein. As such, it will be understood that only one starting cell type needs to be considered when determining relevant factors suitable for reprogramming the somatic cell towards a pluripotent state.

In other embodiments, the population of heterogeneous cells (such as PBMCs) may be reprogrammed according to the methods described herein.

The skilled person will appreciate that this information may be used in performing the methods of the present invention, for example, for the purposes of providing increased amounts of transcription factors in somatic cells, or providing nucleic acids or the like for recombinantly expressing a transcription factor in a somatic cell.

TABLE 2

Accession numbers identifying exemplary nucleotide sequences and amino acid sequences of transcription factors referred to herein.

| Transcription factor Associated Gene Name | Ensembl Gene ID | Uniprot ID |
|---|---|---|
| OCT4 (also called POU5F1) | ENSG00000204531 | Q01860 |
| SOX2 | ENSG00000181449 | P48431 |
| cMYC | ENSG00000136997 | P01106 |
| KLF4 | ENSG00000136826 | O43474 |
| LIN28 | ENSG00000131914 | Q9H9Z2 |
| NANOG | ENSG00000111704 | Q9H9S0 |

The term a "variant" in referring to a polypeptide that is at least 70%, 80%, 85%, 90%, 95%, 98%, or 99% identical to the full length polypeptide. The present invention contemplates the use of variants of the transcription factors described herein. The variant could be a fragment of full length polypeptide or a naturally occurring splice variant. The variant could be a polypeptide at least 70%, 80%, 85%, 90%, 95%, 98%, or 99% identical to a fragment of the polypeptide, wherein the fragment is at least 50%, 60%, 70%, 80%, 85%, 90%, 95%, 98%, or 99% as long as the full length wild type polypeptide or a domain thereof has a functional activity of interest such as the ability to promote conversion of a somatic cell type to a target cell type. In some embodiments the domain is at least 100, 200, 300, or 400 amino acids in length, beginning at any amino acid position in the sequence and extending toward the C-terminus. Variations known in the art to eliminate or substantially reduce the activity of the protein are preferably avoided. In some embodiments, the variant lacks an N- and/or C-terminal portion of the full length polypeptide, e.g., up to 10, 20, or 50 amino acids from either terminus is lacking. In some embodiments the polypeptide has the sequence of a mature (full length) polypeptide, by which is meant a polypeptide that has had one or more portions such as a signal peptide removed during normal intracellular proteolytic processing (e.g., during co-translational or post-translational processing). In some embodiments wherein the protein is produced other than by purifying it from cells that naturally express it, the protein is a chimeric polypeptide, by which is meant that it contains portions from two or more different species. In some embodiments wherein a protein is produced other than by purifying it from cells that naturally express it, the protein is a derivative, by which is meant that the protein comprises additional sequences not related to the protein so long as those sequences do not substantially reduce the biological activity of the protein. One of skill in the art will be aware of, or will readily be able to ascertain, whether a particular polypeptide variant, fragment, or derivative is functional using assays known in the art. For example, the ability of a variant of a transcription factor to convert a somatic cell to a target cell type can be assessed using the assays as disclosed herein in the Examples. Other convenient assays include measuring the ability to activate transcription of a reporter construct containing a transcription factor binding site operably linked to a nucleic acid sequence encoding a detectable marker such as luciferase. In certain embodiments of the invention a functional variant or fragment has at least 50%, 60%, 70%, 80%, 90%, 95% or more of the activity of the full length wild type polypeptide.

The term "increasing the amount of" with respect to increasing an amount of a factor for reprogramming a cell towards a pluripotent state, refers to increasing the quantity of the factor (e.g., a transcription factor) in a cell of interest (e.g., a somatic cell such as a fibroblast). In some embodiments, the amount of factor is "increased" in a cell of interest (e.g., a cell into which an expression cassette directing expression of a polynucleotide encoding one or more factors has been introduced) when the quantity of factor is at least 10%, 20%, 30%, 40%, 50%, 60%, 70%, 80%, 90%, or more relative to a control (e.g., a fibroblast into which none of said expression cassettes have been introduced). However, any method of increasing an amount of a factor is contemplated including any method that increases the amount, rate or efficiency of transcription, translation, stability or activity of a factor (or the pre-mRNA or mRNA encoding it). In addition, down-regulation or interference of a negative regulator of transcription expression, increasing efficiency of existing translation (e.g. SINEUP) are also considered.

The term "agent" as used herein means any compound or substance such as, but not limited to, a small molecule, nucleic acid, polypeptide, peptide, drug, ion, etc. The agent may be any compound or substance which increases the amount of a factor including a transcription factor as described herein. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In certain embodiments, agents are small molecule having a chemical moiety. For example, chemical moieties included unsubstituted or substituted alkyl, aromatic, or heterocyclic moieties including macrolides, leptomycins and related natural products or analogues thereof. Compounds can be known to have a desired activity and/or property, or can be selected from a library of diverse compounds.

The term "exogenous," when used in relation to a protein, gene, nucleic acid, or polynucleotide in a cell or organism refers to a protein, gene, nucleic acid, or polynucleotide that has been introduced into the cell or organism by artificial or natural means; or in relation to a cell, refers to a cell that was isolated and subsequently introduced to other cells or to an organism by artificial or natural means. An exogenous nucleic acid may be from a different organism or cell, or it may be one or more additional copies of a nucleic acid that occurs naturally within the organism or cell. An exogenous cell may be from a different organism, or it may be from the same organism. By way of a non-limiting example, an exogenous nucleic acid is one that is in a chromosomal location different from that of natural cells, or is otherwise flanked by a different nucleic acid sequence than that found in nature. An exogenous nucleic acid may also be extra-chromosomal, such as an episomal vector.

Suitable detection means include the use of labels such as radionucleotides, enzymes, coenzymes, fluorescers, chemiluminescers, chromogens, enzyme substrates or co-factors, enzyme inhibitors, prosthetic group complexes, free radicals, particles, dyes, and the like. Such labelled reagents may be used in a variety of well-known assays, such as radioimmunoassays, enzyme immunoassays, e.g., ELISA, fluorescent immunoassays, and the like. See, for example, U.S. Pat. Nos. 3,766,162; 3,791,932; 3,817,837; and 4,233,402.

The method of the disclosure may be "miniaturized" in an assay system through any acceptable method of miniaturization, including but not limited to, multi-well plates, such as 24, 48, 96 or 384-wells per plate, microchips or slides. The assay may be reduced in size to be conducted on a micro-chip support, advantageously involving smaller amounts of reagent and other materials.

Culture Vessel

Forming a multilayered cell structure of blastocyst-like structure occurs in any suitable container, plate, system or vessel that allows aggregation or self-organisation of the cells. Typically, culturing occurs on any culture plate, culture vessel, microfluidic system or culture system that allows three-dimensional aggregation of cells.

A suitable container, plate, system or vessel preferably has a non-adherent surface. A non-adherent surface is a surface on which the cells are placed, and which has little or no adhesion tendency to the cells. Thus, the cells do essentially not adhere to this surface. Without wishing to be bound by theory, use of a non-adherent surface provides a driving force for the cells to not adhere to the surface, but instead adhere to each other, thus forming a cell structure for use in the present invention.

A non-adherent surface may be formed by coating a material with a non-adherent biological or artificial material, or a non-adherent surface may be obtained by suitably shaping a non-adherent material, or by other means known in the art. A container on or in which the cell aggregate can be formed will from hereon be called a scaffold.

Scaffolds with a non-adherent surface are made of or are coated with, for example, ethylene oxide, propylene oxide, polyethylene glycol, (PEG)-(co)polymers (for instance PLL-g-(PEG)), poly(ethylene oxide) (PEO) (co)polymers, agarose hydrogels, temperature-responsive materials below their Lower Critical Solution Temperatures (LCST) (for example Poly(N-isopropylacrylamide)), hydrophobic materials (for example olefin polymers), cell-repellent micro- and nanotopographies.

Thus, forming a cell aggregate according to the present invention is preferably achieved in a non-adherent scaffold. A non-adherent scaffold has at least one surface that does not essentially allow for the adherence of cells. Preferably, this is the side on or in which cells to form the aggregate are placed. A non-adherent scaffold can be formed from a non-adhering material, or can be formed from another material coated with a non-adherent material. A non-adherent petri dish or tube may for example be used as scaffold, but preferably, the scaffold has a plate-like shape, such as for instance a more or less hexagonal, pentagonal, square, rectangular, triangular, oval or round shape.

More preferably, the scaffold comprises at least one suitable cavity or channel. Preferably, multiple cavities or channels are present on a scaffold. It is preferred if these cavities or channels are somewhat larger than the size of the cell aggregate to be formed. Suitable cavities and channels are small, such as for instance 20-5000 µm in diameter, more preferably 100-1000 µm, and most preferred are cavities of 100-500 µm, especially approximately 200 µm in diameter. Suitable cavities or channels may be obtained by any means known in the art. The diameter is defined as the longest possible straight-line distance between any two opposite points on the circumference of the opening of the cavity or channel. The channel or cavity has a closed bottom, and at least the surface of the inside of the cavity or channel comprises a non-adherent material.

Preferably, a cavity has a shape in which the length and breadth are of approximately similar order of magnitude. The depth, also, is of approximately the same order of magnitude. Such a cavity is called a microwell. For the present invention, it is preferred if the non-adherent scaffold comprises microwells. A microwell is preferably a cavity the length of which is up to about 5 times, preferably 3 times and more preferably approximately equal to its breadth, and which depth is no more than 10 times, preferably no more than 5 times, and more preferably up to 3 times its breadth.

The length of a microwell is defined as the longest possible straight-line distance between any two opposite points on the circumference of the opening of the microwell. Thus, the length of the microwell is considered its diameter, which is preferably for instance 20-5000 µm, more preferably 100-1000 µm, and most preferably 100-500 µm, especially approximately 200 µm. The breadth of a microwell is defined as the longest straight-line distance between any two opposite points on the circumference of the opening of the microwell perpendicular to its length.

The various cross-sectional areas of a microwell, among which those perpendicular and parallel to the surface of the scaffold, may be of any shape, including irregular shapes, but preferably, possible cross-sectional areas of a microwell are independently square or approximately square, rectangular or approximately rectangular, triangular or approximately triangular, oval or approximately oval or round or approximately round. However, it is preferred if the microwell is cylindrical, and has an approximately round opening in the surface of the scaffold. Suitable microwells are for instance present on microwell plates, such as commonly used in the art.

In case a non-adherent scaffold comprises microwells, it is advantageous to have multiple microwells arranged on a single scaffold. Preferably, these microwells are arranged in a regular pattern. This allows for high-throughput preparation of large numbers of blastoids.

In one aspect, the culture vessel is a culture plate with an array of inverse pyramidal microwells of, or of about, 400 µm or 800 µm or between about 400 µm to 800 µm. An exemplary culture plate is an AggreWell™ plate, for example an AggreWell™ 400 or 800. Within each well of an AggreWell™ plate, there are a number of microwells (e.g., in each well a 24-well Aggrewell™, there are 1200 microwells).

Cells can be seeded or added to the microwells by adding a well-dispersed suspension of single cells of known density into the plate well and centrifuging the plate gently to force cells evenly into the microwells, The conditions that allows three-dimensional aggregation of cells include seeding cells at a density of at or about 0.5 to $2 \times 10^5$ cells per well, at or about 0.6 to $2 \times 10^5$ cells per well, at or about 0.8 to $2 \times 10^5$ cells per well, at or about 1 to $2 \times 10^5$ cells per well, at or about $0.6 \times 10^5$ cells per well, at or about $0.8 \times 10^5$ cells per well, at or about $1 \times 10^5$ cells per well, at or about $1.2 \times 10^5$ cells per well, at or about $1.4 \times 10^5$ cells per well, at or about $1.6 \times 10^5$ cells per well, at or about $1.8 \times 10^5$ cells per well, or at or about $2 \times 10^5$ cells per well (e.g., when seeding cells in an AggreWell™ plate as described herein; seeding can be between 1-1000 cells per microwell). Preferably the cells are a single cell suspension before seeding. Preferably, the cells are a cell population of reprogrammed somatic cells exhibiting epiblast (EPI), trophectoderm (TE), and primitive endoderm (PE) transcriptional signatures, or cells in steps c) and/or d) in a method described herein.

Culture Media and Conditions

The term "cell culture medium" (also referred to herein as a "culture medium" or "medium") as referred to herein is a medium for culturing cells containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art. Exemplary cell culture medium for use in methods of the invention are described herein, including those shown in Table 3.

The somatic cells for use in accordance with the methods of the present invention, do not need to have completed reprogramming to the pluripotent state prior to the step of being contacted with the culture medium in step c), as described herein. In other words, the cell is preferably at an intermediate state, transitioning from differentiated state to pluripotent state when it is contacted with the culture medium for enabling aggregation to obtain a blastocyst-like structure or multi-cellular structure. Therefore, the cells at the end of step b) and before culturing in step c), as described herein, may be referred to as reprogramming intermediates.

In certain embodiments, the period of time for culturing the cell to commence reprogramming towards a pluripotent state is at least 1 day following increasing the protein expression, or amount of the one or more factors or starting from when the cells are contacted with an agent to increase protein expression, or amount of the one or more factors. The period of time may be 2, 3, 4, 5, 6, 7, 8, 9, 10, 11, 12, 13, 14, 15, 16, 17, 18, 19, 20 or 21 or more days after increasing the protein expression, or amount of the one or more factors. In any embodiment, the period of time for culturing the cell to commence reprogramming towards a dedifferentiated pluripotent state may be any period of time provided that it enables the reduction of markers associated with the somatic cell.

Figures 11A, 11B, 11C:
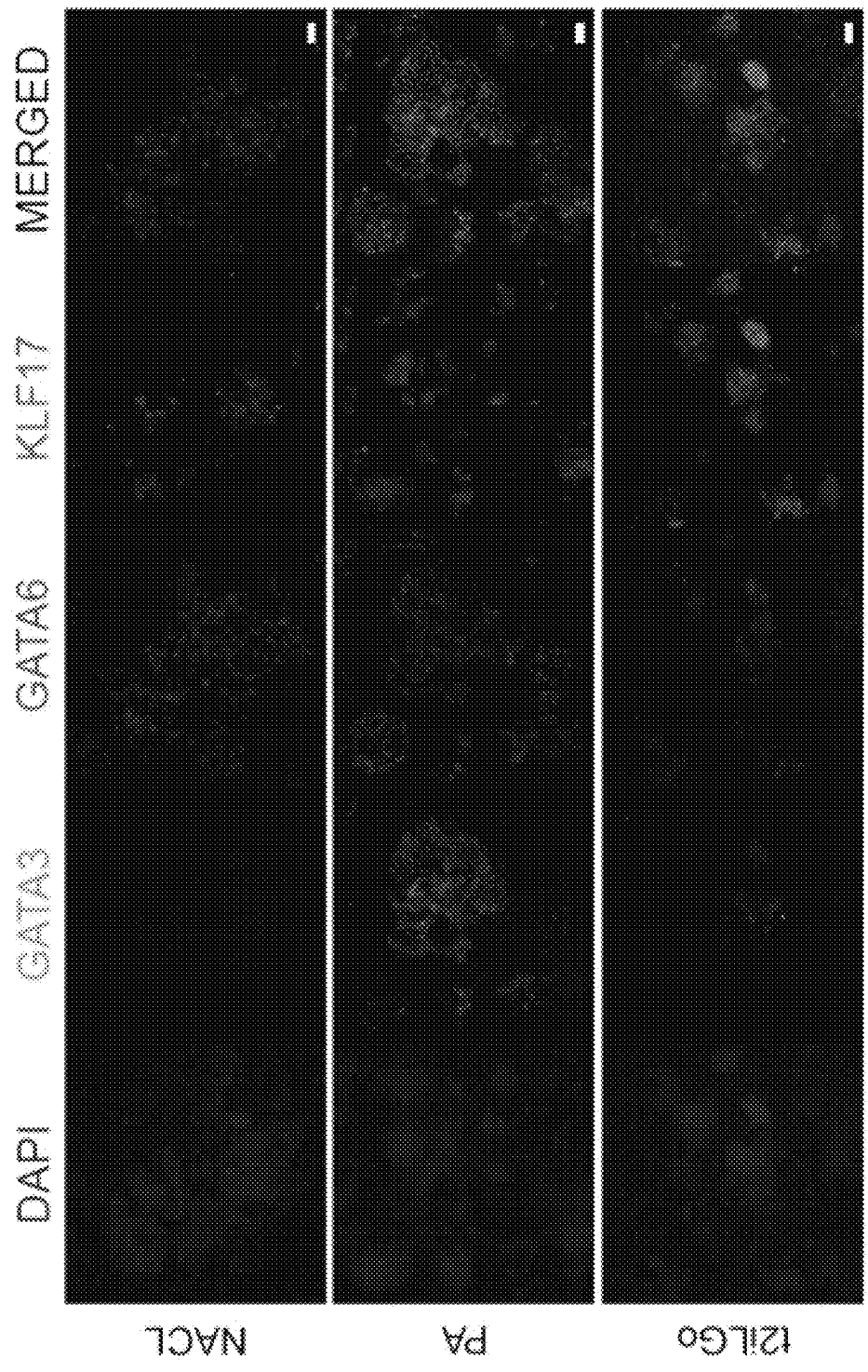
FIGS. 11A-C. Assessment of proportion of EPI, TE and PE-like cells when reprogramming in other culture conditions. D8 reprogramming intermediates were transitioned into NACL medium (FIG. 11A) and PA medium (FIG. 11B) and t2iLGo medium (FIG. 11C) and assessed for proportion of EPI, TE and PE-like cells day 21 of reprogramming. GATA3 was chosen as the marker for TE-like cells, GATA6 for PE-like cells and KLF17 for EPI-like cells. Scale bar, 100 μm.

In further embodiments of the invention, the methods above include culturing the cells towards a dedifferentiated or pluripotent state in a medium that induces upregulation of the EPI, TE and PE lineage transcriptional signatures. Preferably, the medium is one that is suitable for maintaining the somatic cell (or source cell for reprogramming) in culture, and is not a medium used for promoting pluripotency, or is not a medium used for promoting only pluripotency. Where the somatic cells being reprogrammed are fibroblasts, the medium is fibroblast medium, for example the fibroblast medium defined herein, including in Table 3a and/or 3b. It will be appreciated that other media may be suitable such as those in Table 3a, and as shown in FIG. 11 or when the source cell for reprogramming is not a fibroblast (eg, where the source cell is an epithelial cell, endothelial cell, keratinocytes etc); examples of such media are also listed in Table 3b.

As used herein, the culture medium in step c) may also be referred to as a blastocyst promoting medium or iBlastoid medium. Preferably, the blastocyst promoting medium or iBlastoid medium is any as defined herein. In any embodiment, the cells are cultured in the culture medium in step c) for a period of at least about 1, at least about 2, at least about 3, at least about 4, at least about 5, at least about 6, at least about 8, at least about 10, at least about 12, at least about 14, at least about 16, at least about 20, at least about 24 or more days.

In any embodiment, the period of time between increasing the protein expression or amount of the factors for reprogramming the somatic cells towards a pluripotent state, and contacting the cell with the culture medium in step c), may be any period of time provided that it enables the reduction of markers associated with the somatic cell. In further examples, the period of time between increasing the protein expression or amount of the factors and contacting the cell with the culture medium in step c) may be any period of time provided that it enables the cell to proceed through mesenchymal to epithelial transition states. In further or alternative embodiments, the period of time can be any period provided that it enables the expression of epiblast (EPI), trophectoderm (TE), and primitive endoderm (PE) transcriptional signatures.

In another aspect, the present invention provides a culture medium for promoting cells to exhibit at least one characteristic of a blastocyst-like structure, the culture medium comprising
    an agent for activating signalling of the WNT pathway (optionally a GSK-3 inhibitor);
    at least one, preferably 2, TGF-3 inhibitors,
    a HDAC inhibitor,
    a growth factor (preferably EGF), and
    a BMP (preferably BMP4).

In this aspect, the agent for activating WNT pathway signalling (optionally a GSK-3 inhibitor), TGF-3 inhibitor (s), HDAC inhibitor may be any one known in the art, including any one described herein.

Preferably, the culture medium further comprises:
    ITS-X;
    L-Glutamine;
    N-acetyl-L-cysteine;
    B-estradiol;
    Progesterone;
    2-mercaptethanol;
    L-ascorbic acid;
    Transferrin (e.g. human),
    Insulin (e.g. human),
    N2 supplement; and
    B27 supplement.

Preferably, the progesterone, transferrin and insulin are provided in a N2 supplement as described herein, further including putrescine and selenite.

Preferably, the B27 supplement comprises biotin, DL alpha tocopherol acetate, DL alpha tocopherol, Vitamin A (Acetate), BSA, catalase, Insulin (human), superoxide dismutase, corticosterone, D-galactose, Ethanolamine HCL, Glutathione, L-Carnitine HCL, Linoleic Acid, Linolenic Acid, Progesterone, Putrescine 2HCI, Sodium Selenite, T3 (triodo-l-thyronine).

In any embodiment, the culture medium further comprises an antibiotic, for example penicillin-streptomycin.

In one embodiment, the culture medium comprises:
    IVC1 medium, N2B27 basal medium and TSC basal medium as defined herein in a respective 2:1:1 ratio,
    an agent for activating signalling of the WNT pathway (optionally a GSK-3 inhibitor),
    at least one, preferably 2, TGF-3 inhibitors,
    a HDAC inhibitor,
    a growth factor (preferably EGF), and
    a BMP (preferably BMP4).

Preferably the TGF-β pathway inhibitor is selected from SB431542 and A83-01, the histone deacetylase (HDAC)1 inhibitor is VPA (Valproic Acid), the GSK-3 Inhibitor is CHIR99021.

Preferably, the GSK-3 Inhibitor is at a concentration of, or about, 2 μM, the TGF-β pathway inhibitor is at a concentration of, or about, 0.5 μM or 1 μM, histone deacetylase (HDAC)1 inhibitor is at a concentration of, or about, 0.8 mM, EGF is at a concentration of, or about, 50 ng/ml, and BMP4 is at a concentration of, or about, 10 ng/ml.

As used herein, a growth factor may be any growth factor, but is preferable one selected from Epidermal Growth Factor (EGF), insulin, transforming growth factor (TGF). The amount of growth factor may be any amount, for example 0.1 to 1000 ng/ml, preferably 10-100 ng/ml, preferably 50 ng/ml.

As used herein, a ROCK inhibitor refers to an inhibitor of Rho-binding kinase. Examples of such inhibitors include ((1R,4r)-4-((R)-1-aminoethyl)-N-(pyridin-4-yl)cyclohexane carboxamide, Abcam), also known as trans-N-(4-(1-aminoethyl)-cyclohexanecarboxamide, 1-(5-isoquinolunyl) (sulfonyl) homopiperazine (1-(5-isoquinolinylsulfonyl)homopiperazine. Typically the amount of ROCK inhibitor will be between about 0.1 to 50 µM, preferably about 1 to 10 µM.

Preferably, the ROCK inhibitor is Y-27632. Preferably, the ROCK inhibitor is at a concentration of, or about, 10 µM.

In another aspect, the culture medium comprises or consists of the Fibroblast medium, the N2B27 basal medium, the TSC basal medium, the IVC1 medium, the IVC2 medium or the Human iBlastoid medium as defined in Table 3a.

In any aspect, the culture medium defined in step c) of any method of the invention may be any culture medium of the invention, including but not limited to the Human iBlastoid medium as defined herein, including in Table 3a.

TABLE 3a

Cell culture media that can be used to culture different cell types and at various stages of the methods described herein.

| Media | Components | Company/Reference |
|---|---|---|
| Fibroblast medium | DMEM | ThermoFisher |
| | 10% Fetal Bovine Serum (FBS) | ThermoFisher |
| | 1% Nonessential amino acids | ThermoFisher |
| | 1 mM GlutaMAX | ThermoFisher |
| | 1% Penicillin-streptomycin | ThermoFisher |
| | 55 µM 2-mercaptoethanol and | ThermoFisher |
| | 1 mM sodium pyruvate | ThermoFisher |
| NACL medium | N2B27 basal medium supplemented with: | |
| | 3 µM CHIR99021 | Miltenyi Biotec |
| | 100 ng/ml Activin A | Peprotech |
| | 10 ng/ml human LIF | Made in house/Peprotech |
| PA medium | N2B27 basal medium supplemented with: | |
| | 1 µM PD0325901 | Miltenyi Biotec |
| | 1 µM A83-01 | Sigma |
| t2iLGo medium | N2B27 basal medium supplemented with: | |
| | 1 µM PD0325901 | Miltenyi Biotec |
| | 1 µM CHIR99021 | Miltenyi Biotec |
| | 2.5 µM Go6983 | Tocris |
| | 250 µM Ascorbic Acid | Sigma |
| | 10 ng/ml human LIF | Made in house/Peprotech |
| | 10 µM Y27632 | Selleckchem |
| N2B27 basal medium | 50:50 mixture of DMEM/F-12 and Neurobasal medium supplemented with: | All components from ThermoFisher |
| | 2 mM L-Glutamine | |
| | 0.1 mM 2-mercaptoethanol | |
| | 0.5% N2 supplement | |
| | 1% B27 supplement | |
| | 1% Penicillin-streptomycin | |
| TSC basal medium | DMEM/F-12, GlutaMAX supplemented with: | ThermoFisher |
| | 0.3% BSA | Sigma |
| | 0.2% FBS | ThermoFisher |
| | 1% ITS-X supplement | ThermoFisher |
| | 0.1 mM 2-mercaptoethanol | ThermoFisher |
| | 0.5% Penicillin-streptomycin | ThermoFisher |
| | 1.5 µg/ml L-ascorbic acid | Sigma |
| IVC1 medium | Advanced DMEM/F-12 | ThermoFisher |
| | 1% ITS-X supplement | ThermoFisher |
| | 2 mM L-Glutamine | ThermoFisher |
| | 0.5% Penicillin-streptomycin | ThermoFisher |
| | 20% Fetal Bovine Serum (FBS) | ThermoFisher |
| | 25 µM N-acetyl-L-cysteine | Sigma |
| | 8 nM β-estradiol | Sigma |
| | 200 ng/ml progesterone | Sigma |
| IVC2 medium | Advanced DMEM/F-12 | ThermoFisher |
| | 1% ITS-X supplement | ThermoFisher |
| | 2 mM L-Glutamine | ThermoFisher |
| | 0.5% Penicillin-streptomycin | ThermoFisher |
| | 30% Knockout Serum Replacement (KSR) | ThermoFisher |
| | 25 µM N-acetyl-L-cysteine | Sigma |
| | 8 nM β-estradiol | Sigma |
| | 200 ng/ml progesterone | Sigma |
| Human iBlastoid medium | IVC1 medium, N2B27 basal medium and TSC basal medium (as above) in a respective 2:1:1 ratio supplemented with: | |

TABLE 3a-continued

Cell culture media that can be used to culture different cell types and at various stages of the methods described herein.

| Media | Components | Company/Reference |
|---|---|---|
| | 2 µM CHIR99021 | Miltenyi Biotec |
| | 0.5 µM A83-01 | Sigma |
| | 1 µM SB431542 | |
| | 0.8 mM Valproic acid (VPA) | Sigma |
| | 50 ng/ml EGF | Peprotech |
| | 10 ng/ml BMP4 | Miltenyi Biotec |
| | Optionally with: | |
| | 10 µM Y-27632 | Selleckchem |

TABLE 3b

Cell culture media that can be used to culture various somatic cell types

| Cell | Media | Cat#: | Company |
|---|---|---|---|
| Astrocytes | Astrocyte Medium | A1261301 | Life Technologies |
| Dermal fibroblasts | Medium106 | M-106-500 | ThermoFisher |
| Endothelial cells | Medium 131 | M131500 | Life Technologies |
| Epidermal Keratinocytes | EpiLife | M-EPICF-500 | ThermoFisher |
| H9 ESC line | KSR | 10828-028 | ThermoFisher |
| | Essential 8 | A1517001 | Life Technologies |
| Monocytes | Macrophage-SFM | 12065-074 | ThermoFisher |
| Chondrocytes | Eagle's Minimum Essential Medium | 10-009-CV | Corning |
| Hair Follicles | Medium 199/Ham's F12 | 11150-059/ 11765-047 | ThermoFisher |
| CD4+ T-cell | CTS ™ OpTmizer ™ T Cell Expansion SFM | A10485-01 | ThermoFisher |
| CD8+ T-cell | CTS ™ OpTmizer ™ T Cell Expansion SFM | A10485-01 | ThermoFisher |
| NK-cell | alpha MEM | M 8042 | Sigma Aldrich |
| PSCs | Essential 8 Medium | A1517001 | Life Technologies |
| HSCs | StemPro ® CD34+ Cell Kit | A14059 | ThermoFisher |
| MSCs of adipose | StemPro ® Human Adipose-Derived Stem Cell Kit | R7788-110 | ThermoFisher |
| MSCs of bone marrow | StemPro ® BM Mesenchymal Stem Cells kit | A15652 | ThermoFisher |
| | Alpha-MEM with 15% FBS, glutamine, penicillin ands treptomycin | | Life Technologies |
| Oligodendrocytes precursors | Neurobasal medium | 21103-049 | ThermoFisher |
| Skeletal muscle cells | DMEM | 11965-092 | ThermoFisher |
| Smooth muscle cells | Medium 231 | M-231-500 | ThermoFisher |

Nucleic Acids and Vectors

A nucleic acid or vector comprising a nucleic acid as described herein may include one or more of the sequences referred to above in Table 2. The nucleic acid or vector may comprise a sequence encoding one or more of the factors for reprogramming the somatic cells towards a pluripotent state.

The term "expression" refers to the cellular processes involved in producing RNA and proteins and as appropriate, secreting proteins, including where applicable, but not limited to, for example, transcription, translation, folding, modification and processing.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated".

The term "vector" refers to a carrier DNA molecule into which a DNA sequence can be inserted for introduction into a host or somatic cell. Preferred vectors are those capable of autonomous replication and/or expression of nucleic acids to which they are linked. Vectors capable of directing the expression of genes to which they are operatively linked are referred to herein as "expression vectors". Thus, an "expression vector" is a specialized vector that contains the necessary regulatory regions needed for expression of a gene of interest in a host cell. In some embodiments the gene of interest is operably linked to another sequence in the vector. Vectors can be viral vectors or non-viral vectors. Should viral vectors be used, it is preferred the viral vectors are replication defective, which can be achieved for example by removing all viral nucleic acids that encode for replication. A replication defective viral vector will still retain its infective properties and enters the cells in a similar manner as a replicating adenoviral vector, however once admitted to the cell a replication defective viral vector does not reproduce or multiply. Vectors also encompass liposomes and nanoparticles and other means to deliver DNA molecule to a cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. The term "operatively linked" includes having an appropriate start signal (e.g. ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

The term "viral vectors" refers to the use of viruses, or virus-associated vectors as carriers of a nucleic acid construct into a cell. Constructs may be integrated and packaged into non-replicating, defective viral genomes like Adenovirus, Adeno-associated virus (AAV), or Herpes simplex virus (HSV) or others, including retroviral and lentiviral vectors, Sendai virus vector, for infection or transduction into cells. The vector may or may not be incorporated into the cell's genome. The constructs may include viral sequences for transfection, if desired. Alternatively, the construct may be incorporated into vectors capable of episomal replication, e.g EPV and EBV vectors.

As used herein, the term "adenovirus" refers to a virus of the family Adenovirida. Adenoviruses are medium-sized (90-100 nm), nonenveloped (naked) icosahedral viruses composed of a nucleocapsid and a double-stranded linear DNA genome.

As used herein, the term "non-integrating viral vector" refers to a viral vector that does not integrate into the host genome; the expression of the gene delivered by the viral vector is temporary. Since there is little to no integration into the host genome, non-integrating viral vectors have the advantage of not producing DNA mutations by inserting at a random point in the genome. For example, a non-integrating viral vector remains extra-chromosomal and does not insert its genes into the host genome, potentially disrupting the expression of endogenous genes. Non-integrating viral vectors can include, but are not limited to, the following: adenovirus, alphavirus, picornavirus, and vaccinia virus. These viral vectors are "non-integrating" viral vectors as the term is used herein, despite the possibility that any of them may, in some rare circumstances, integrate viral nucleic acid into a host cell's genome. What is critical is that the viral vectors used in the methods described herein do not, as a rule or as a primary part of their life cycle under the conditions employed, integrate their nucleic acid into a host cell's genome.

The vectors described herein can be constructed and engineered using methods generally known in the scientific literature to increase their safety for use in therapy, to include selection and enrichment markers, if desired, and to optimize expression of nucleotide sequences contained thereon. The vectors should include structural components that permit the vector to self-replicate in the somatic cell type. For example, the known Epstein Barr oriP/Nuclear Antigen-1 (EBNA-1) combination (see, e.g., Lindner, S. E. and B. Sugden, The plasmid replicon of Epstein-Barr virus: mechanistic insights into efficient, licensed, extrachromosomal replication in human cells, Plasmid 58:1 (2007), incorporated by reference as if set forth herein in its entirety) is sufficient to support vector self-replication and other combinations known to function in mammalian, particularly primate, cells can also be employed. Standard techniques for the construction of expression vectors suitable for use in the present invention are well-known to one of ordinary skill in the art and can be found in publications such as Sambrook J, et al., "Molecular cloning: a laboratory manual," (3rd ed. Cold Spring harbor Press, Cold Spring Harbor, N. Y. 2001), incorporated herein by reference as if set forth in its entirety.

In the methods of the invention, genetic material encoding the relevant transcription factors required for a conversion is delivered into the somatic cells via one or more reprogramming vectors. Each transcription factor can be introduced into the somatic cells as a polynucleotide transgene that encodes the transcription factor operably linked to a heterologous promoter that can drive expression of the polynucleotide in the somatic cell.

Suitable reprogramming vectors are any described herein, including episomal vectors, such as plasmids, that do not encode all or part of a viral genome sufficient to give rise to an infectious or replication-competent virus, although the vectors can contain structural elements obtained from one or more virus. One or a plurality of reprogramming vectors can be introduced into a single somatic cell. One or more transgenes can be provided on a single reprogramming vector. One strong, constitutive transcriptional promoter can provide transcriptional control for a plurality of transgenes, which can be provided as an expression cassette. Separate expression cassettes on a vector can be under the transcriptional control of separate strong, constitutive promoters, which can be copies of the same promoter or can be distinct promoters. Various heterologous promoters are known in the art and can be used depending on factors such as the desired expression level of the transcription factor. It can be advantageous, as exemplified below, to control transcription of separate expression cassettes using distinct promoters having distinct strengths in the cells. Another consideration in selection of the transcriptional promoters is the rate at which the promoter(s) is silenced. The skilled artisan will appreciate that it can be advantageous to reduce expression of one or more transgenes or transgene expression cassettes after the product of the gene(s) has completed or substantially completed its role in the reprogramming method. Exemplary promoters are the human EF1α elongation factor promoter, CMV cytomegalovirus immediate early promoter and CAG chicken albumin promoter, and corresponding homologous promoters from other species. In human somatic cells, both EF1α and CMV are strong promoters, but the CMV promoter is silenced more efficiently than the EF1α promoter such that expression of transgenes under control of the former is turned off sooner than that of transgenes under control of the latter. The transcription factors can be expressed in the somatic cells in a relative ratio that can be varied to modulate reprogramming efficiency. Preferably, where a plurality of transgenes is encoded on a single transcript, an internal ribosome entry site is provided upstream of transgene(s) distal from the transcriptional promoter. Although the relative ratio of factors can vary depending upon the factors delivered, one of ordinary skill in possession of this disclosure can determine an optimal ratio of factors.

The skilled artisan will appreciate that the advantageous efficiency of introducing all factors via a single vector rather than via a plurality of vectors, but that as total vector size increases, it becomes increasingly difficult to introduce the vector. The skilled artisan will also appreciate that the position of a transcription factor on a vector can affect its temporal expression, and the resulting reprogramming efficiency. As such, the methods of the invention can be performed using various combinations of factors on combinations of vectors. Several such combinations are known to support reprogramming.

After introduction of the reprogramming vector(s) and while the somatic cells are being reprogrammed, the vectors can persist in target cells while the introduced transgenes are transcribed and translated. Transgene expression can be advantageously downregulated or turned off in cells that have been reprogrammed to a target cell type. The reprogramming vector(s) can remain extra-chromosomal. At extremely low efficiency, the vector(s) can integrate into the cells' genome. The examples that follow are intended to illustrate but in no way limit the present invention.

Suitable methods for nucleic acid delivery for transformation of a cell, a tissue or an organism for use with the current invention are believed to include virtually any method by which a nucleic acid (e.g., DNA) can be introduced into a cell, a tissue or an organism, as described herein or as would be known to one of ordinary skill in the art (e.g., Stadtfeld and Hochedlinger, Nature Methods 6(5):329-330 (2009); Yusa et al., Nat. Methods 6:363-369 (2009); Woltjen, et al., Nature 458, 766-770 (9 Apr. 2009)). Such methods include, but are not limited to, direct delivery of DNA such as by ex vivo transfection (Wilson et al., Science, 244:1344-1346, 1989, Nabel and Baltimore, Nature 326: 711-713, 1987), optionally with a lipid-based transfection reagent such as Fugene®6 (Roche) or Lipofectamine™ (Invitrogen), by injection (U.S. Pat. Nos. 5,994,624, 5,981, 274, 5,945,100, 5,780,448, 5,736,524, 5,702,932, 5,656,610, 5,589,466 and 5,580,859, each incorporated herein by reference), including microinjection (Harland and Weintraub, J. Cell Biol., 101:1094-1099, 1985; U.S. Pat. No. 5,789,215, incorporated herein by reference); by electroporation (U.S. Pat. No. 5,384,253, incorporated herein by reference; Tur-Kaspa et al., Mol. Cell Biol., 6:716-718, 1986; Potter et al., Proc. Nat'l Acad. Sci. USA, 81:7161-7165, 1984); by calcium phosphate precipitation (Graham and Van Der Eb, Virology, 52:456-467, 1973; Chen and Okayama, Mol. Cell Biol., 7(8):2745-2752, 1987; Rippe et al., Mol. Cell Biol., 10:689-695, 1990); by using DEAE-dextran followed by polyethylene glycol (Gopal, Mol. Cell Biol., 5:1188-1190, 1985); by direct sonic loading (Fechheimer et al., Proc. Nat'l Acad. Sci. USA, 84:8463-8467, 1987); by liposome mediated transfection (Nicolau and Sene, Biochim. Biophys. Acta, 721:185-190, 1982; Fraley et al., Proc. Nat'l Acad. Sci. USA, 76:3348-3352, 1979; Nicolau et al., Methods Enzymol., 149:157-176, 1987; Wong et al., Gene, 10:87-94, 1980; Kaneda et al., Science, 243:375-378, 1989; Kato et al., J Biol. Chem., 266:3361-3364, 1991) and receptor-mediated transfection (Wu and Wu, Biochemistry, 27:887-892, 1988; Wu and Wu, J. Biol. Chem., 262:4429-4432, 1987); and any combination of such methods, each of which is incorporated herein by reference.

A number of polypeptides capable of mediating introduction of associated molecules into a cell have been described previously and can be adapted to the present invention. See, e.g., Langel (2002) Cell Penetrating Peptides: Processes and Applications, CRC Press, Pharmacology and Toxicology Series. Examples of polypeptide sequences that enhance transport across membranes include, but are not limited to, the Drosophila homeoprotein antennapedia transcription protein (AntHD) (Joliot et al., New Biol. 3: 1121-34, 1991; Joliot et al., Proc. Natl. Acad. Sci. USA, 88: 1864-8, 1991; Le Roux et al., Proc. Natl. Acad. Sci. USA, 90: 9120-4, 1993), the herpes simplex virus structural protein VP22 (Elliott and O'Hare, Cell 88: 223-33, 1997); the HIV-1 transcriptional activator TAT protein (Green and Loewenstein, Cell 55: 1179-1188, 1988; Frankel and Pabo, Cell 55:1 289-1193, 1988); Kaposi FGF signal sequence (kFGF); protein transduction domain-4 (PTD4); Penetratin, M918, Transportan-10; a nuclear localization sequence, a PEP-1 peptide; an amphipathic peptide (e.g., an MPG peptide); delivery enhancing transporters such as described in U.S. Pat. No. 6,730,293 (including but not limited to an peptide sequence comprising at least 5-25 or more contiguous arginines or 5-25 or more arginines in a contiguous set of 30, 40, or 50 amino acids; including but not limited to an peptide having sufficient, e.g., at least 5, guanidino or amidino moieties); and commercially available Penetratin™ 1 peptide, and the Diatos Peptide Vectors ("DPVs") of the Vectocell® platform available from Daitos S. A. of Paris, France. See also, WO/2005/084158 and WO/2007/123667 and additional transporters described therein. Not only can these proteins pass through the plasma membrane but the attachment of other proteins, such as the transcription factors described herein, is sufficient to stimulate the cellular uptake of these complexes.

Use and Applications

A multi-layered cellular structure or blastocyst-like structure, as made according to the invention, may also be used to prepare model systems for disorders associated with development and/or activity of blastocysts or cells therein. The systems find utility in screening for genes expressed in or essential for blastocyst differentiation and/or activity, to screen for agents and conditions (such as culture conditions and manipulation) that affect development, to produce specific growth factors and hormones, or as a cell therapy for disorders associated with development.

Thus, according to an aspect of the present invention, there is provided a method of identifying an agent capable of modulating blastocyst development and/or activity, the method comprising:

(i) contacting a multi-layered cellular structure or blastocyst-like structure, preferably made according to the methods of present invention, with a candidate agent; and (ii) comparing development and/or activity of the multi-layered cellular structure or blastocyst-like structure following said contacting with said agent to development and/or activity of a the multi-layered cellular structure or blastocyst-like structure without the agent, wherein an effect of said agent on said development and/or activity of the multi-layered cellular structure or blastocyst-like structure above a predetermined level relative to said development and/or activity of the multi-layered cellular structure or blastocyst-like structure without the agent is indicative that said drug modulates blastocyst development and/or activity.

As used herein, the term "modulating" refers to altering blastocyst development and/or activity either by inhibiting or by promoting.

According to specific embodiments, modulating is inhibiting development and/or activity.

According to specific embodiments, modulating is promoting development and/or activity.

For the same culture conditions the effect of the candidate agent on the multi-layered cellular structure or blastocyst-like structure development and/or activity is generally expressed in comparison to the development and/or activity in a multi-layered cellular structure or blastocyst-like structure of the same species but not contacted with the candidate agent or contacted with a vehicle control, also referred to as control.

As used herein the phrase "an effect above a predetermined level" refers to a change in multi-layered cellular structure or blastocyst-like structure development and/or activity following contacting with the agent which is higher than a predetermined level such as a about 10%, e.g., higher than about 20%, e.g., higher than about 30%, e.g., higher than about 40%, e.g., higher than about 50%, e.g., higher than about 60%, higher than about 70%, higher than about 80%, higher than about 90%, higher than about 2 times, higher than about three times, higher than about four time, higher than about five times, higher than about six times, higher than about seven times, higher than about eight times, higher than about nine times, higher than about 20 times, higher than about 50 times, higher than about 100 times, higher than about 200 times, higher than about 350, higher than about 500 times, higher than about 1000 times, or more relative to the presence or level of any marker described herein prior to contacting with the candidate agent.

According to specific embodiments, the candidate agent may be any compound including, but not limited to a chemical, a small molecule, a polypeptide and a polynucleotide.

According to specific embodiments the selected agents may be further used to treat various conditions requiring regulation of blastocyst development or activity such as the conditions described herein.

As blastocysts produce several secreted growth factors and hormones, and particles, such as exosomes according to another aspect of the present invention, there is provided a method of obtaining a compound or particle produced by a multi-layered cellular structure or blastocyst-like structure, the method comprising culturing a the multi-layered cellular structure or blastocyst-like structure of the present invention and isolating from the culture medium a compound or particle secreted by the cells, thereby obtaining the compound or particle produced by the multi-layered cellular structure or blastocyst-like structure.

As outlined herein, the present invention provides somatic cells directly reprogrammed into human blastoids and provides an approach that does not involve the use of natural occurring human blastocysts. For completeness, the methods of the invention:
- do not involve the destruction of an embryo;
- does not involve fertilisation;
- does not involve activation of an oocyte;
- cannot develop into a human being; and
- is not a step on the path of generating a human being; and
- does not involve a primary natural vehicle harvested from a pregnant woman.

Further, the multi-layered cellular structure or blastocyst-like structures may be cultured for the minimal time necessary, for example a maximum of 5 additional days (equivalent to ~E11), preferably 4.5 days, and terminating the experiments before morphological evidence of primitive streak.

EXAMPLES

Example 1—Ethics Statement

This research was performed with the approval of the Institutional Monash University Human Research Ethics Committee (MUHREC 2020-22909-39935 and MUHREC 2020-27147-51995). MUHREC 2020-22909-39935 covered the work involving functional and molecular characterization of human fibroblasts undergoing reprogramming and characterising these cells using 3D-organoid based culture systems (blastoids). MUHREC 2020-27147-51995 covered the generation, molecular and functional characterization of iBlastoids.

Furthermore, since there is currently no precedent to working with human blastoid models, beside seeking approval the inventors' institutional Human Research Ethics Committee, the inventors performed all experiments in concordance with published recommendations (Hyun et al. Stem Cell Reports 14, 169-174 (2020)), as well as adhering to the international consensus for culturing human embryos up to 14 days post-fertilization and/or formation of primitive streak (PS), whichever is first (Warnock, Ir. Nurs. News 5, 7-8 (1985)).

Given that the applicability of the "14-day rule" is unclear for iBlastoids (since the starting material is not from embryonic origin), HDFs were derived from adult tissues, the inventors focused on culturing the iBlastoids for the minimal time necessary, in this case a maximum of 5 additional days (equivalent to ~E11), and terminating the experiments before morphological evidence of PS so as to remain well within international guidelines (Hyun and Warnock, Supra).

Figure 8:
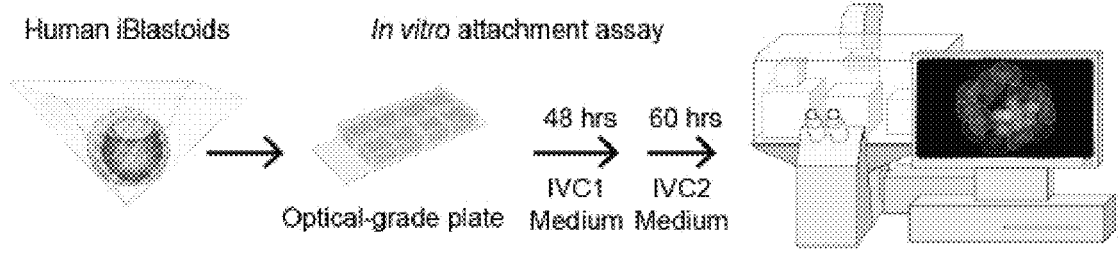
FIG. 8. Assessment of epiblast development in attached iBlastoids. *a*, Schematic of the experimental design for iBlastoid in vitro attachment assay. *b*, Time-course qRT-PCR analysis of primitive streak markers (TBXT, EOMES, and MIXL1) in iBlastoids for up to day 5 in the attachment assay. Positive control for TBXT, EOMES, and MIXL1 was generated using a previously published mesoderm differentiation protocol (Lam et al., 2014, J. Am. Soc. Nephrol.) (n=6) *c*, Attached iBlastoids stained for CDX2 and NANOG (n=5). *d*, Attached iBlastoids stained for GATA2, OCT4, and SOX2 (n=3). *e*, Zoom-in view of attached iBlastoids stained for NANOG, and SOX17 (n=2). *f*, Zoom-in view of attached iBlastoids stained for OCT4, and GATA6 (n=2). Scale bar for *c-f*, 100 μm. *g*, Z-section series of attached iBlastoids stained with F-actin, OCT4 and aPKC with the zoom-in view of pro-amniotic cavity, n=2. Scale bar, 20 μm. *h*, Immunostaining of iBlastoids, day 1 attached iBlastoids and day 3 attached iBlastoids for F-actin, OCT4 and aPKC, n=2. Scale bar, 20 μm. The appearance of the pro-amniotic-like cavity is marked by the arrows. *i*, Immunostaining of iBlastoids and attached iBlastoids for KRT7 and NANOG, n=4. *j*, Attached iBlastoids stained for F-actin and NANOG, n=2, *k*, Immunostaining of iBlastoids and attached iBlastoids for MMP2 and hCG, n=2.
Figure 8:
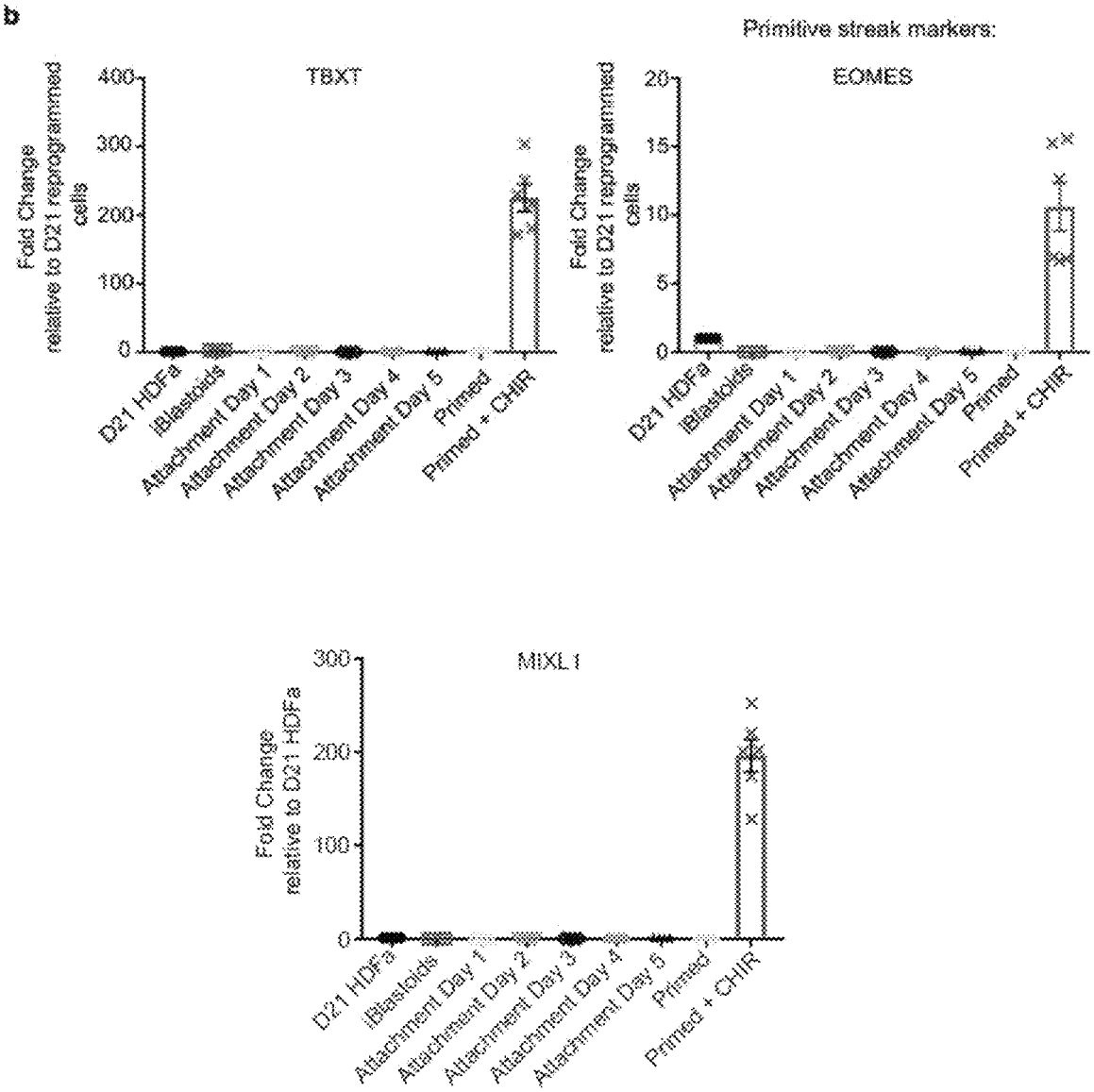
Figure 8:
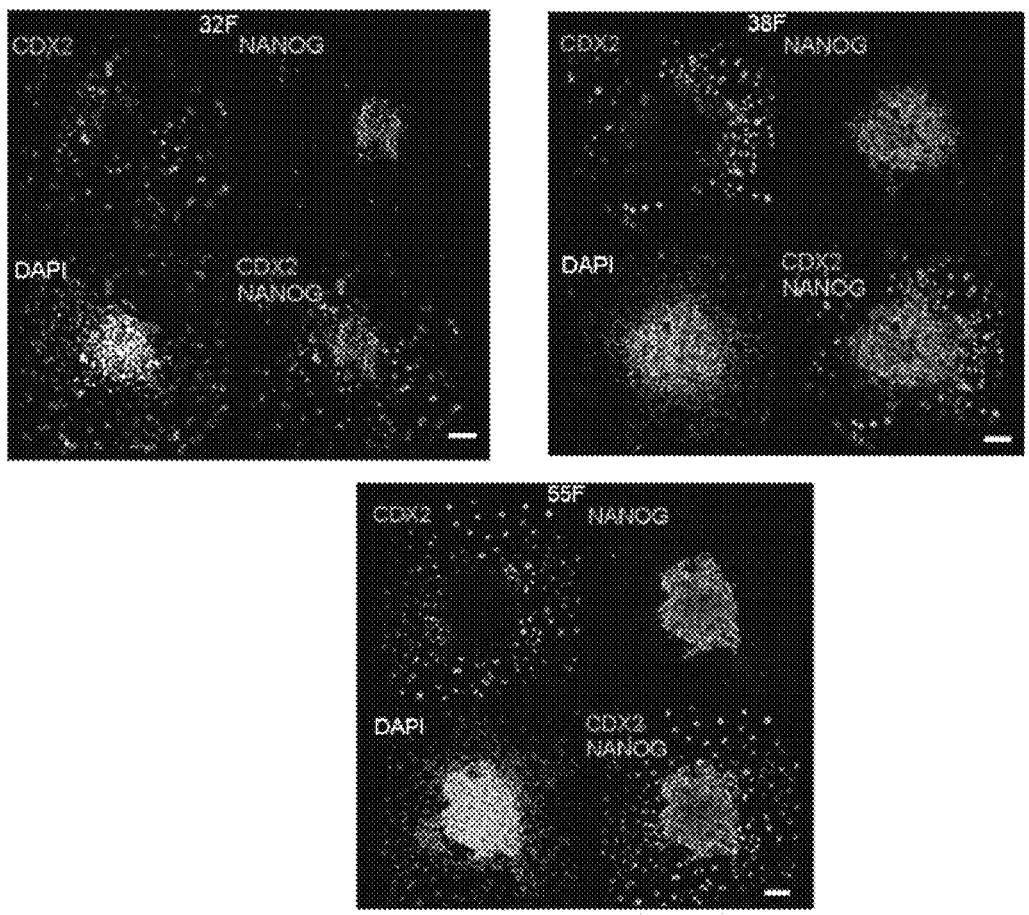
Figure 8:
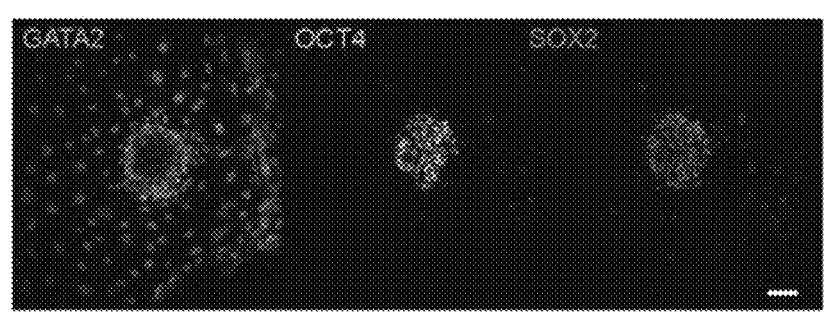
Figure 8:
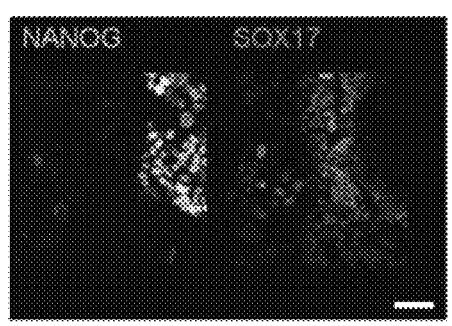
Figure 8:
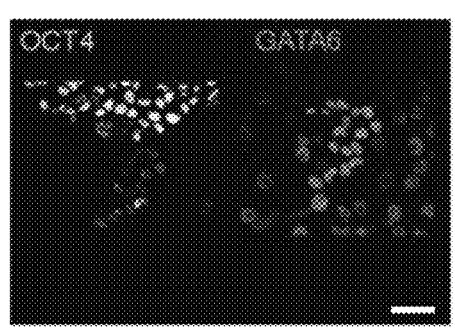
Figure 8:
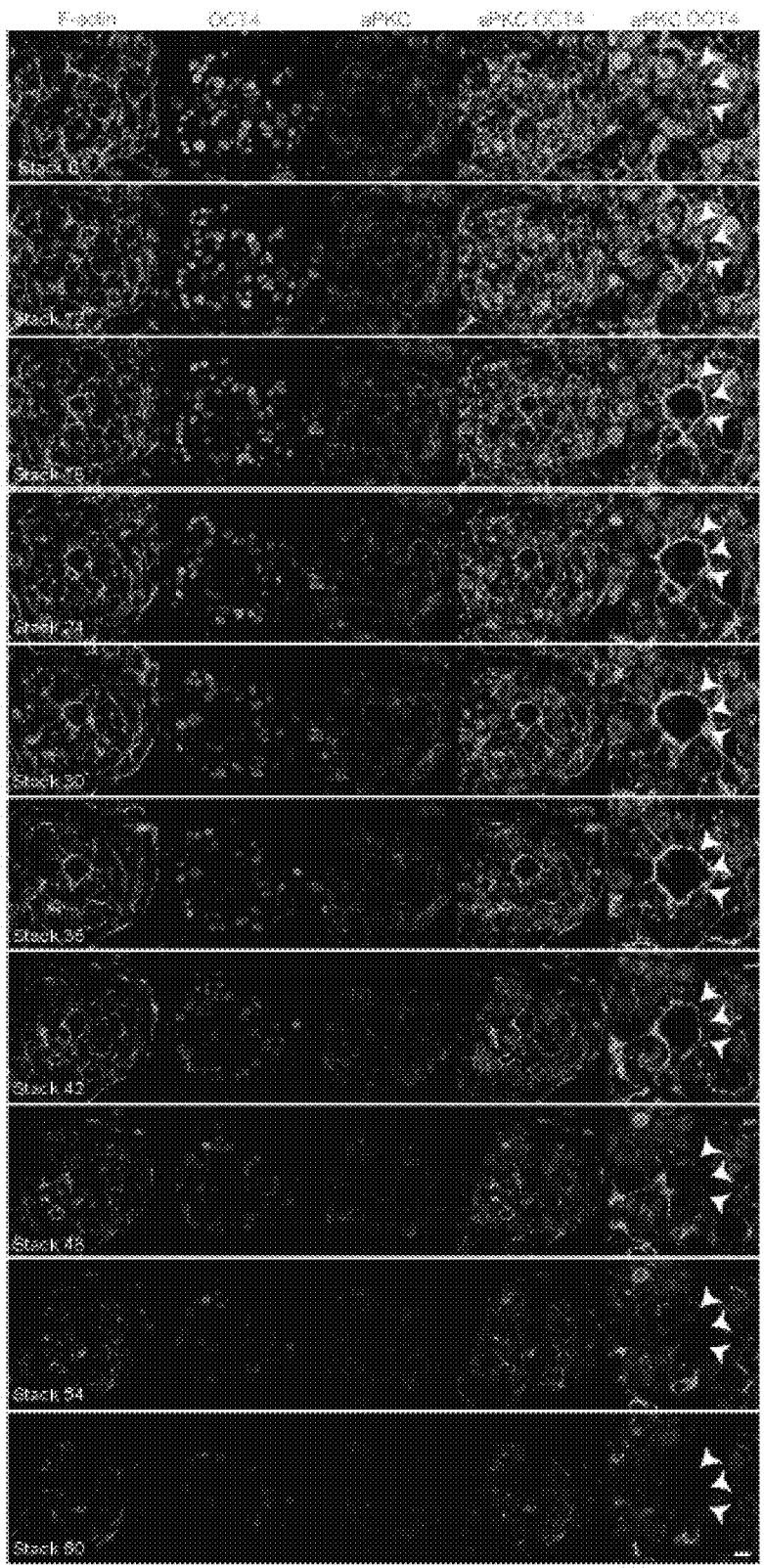
Figure 8:
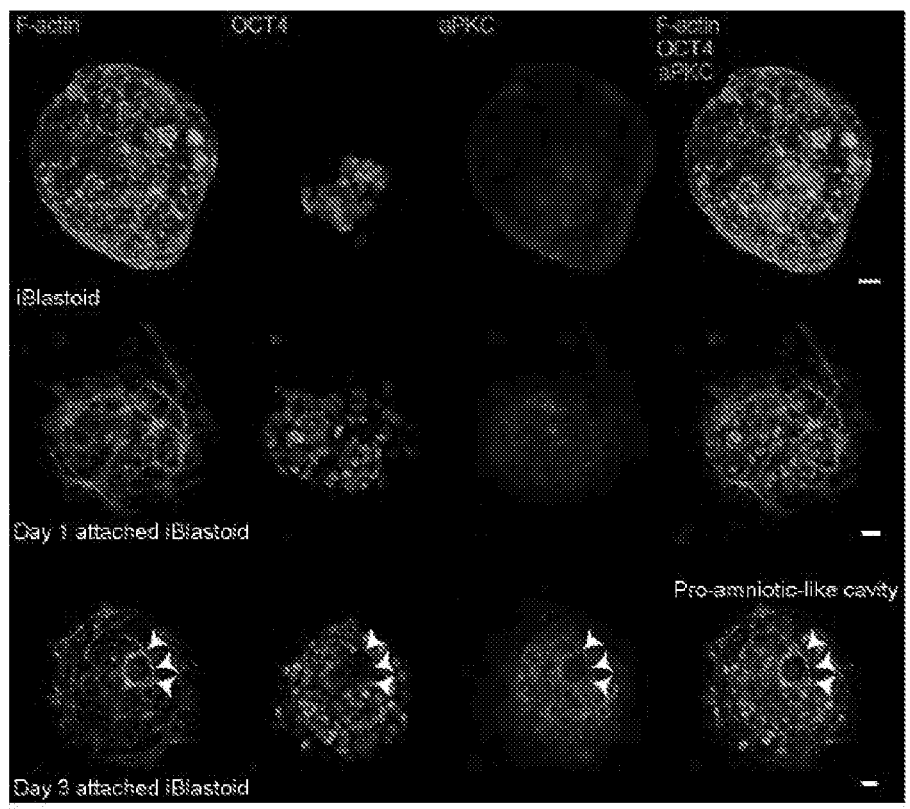
Figure 8:
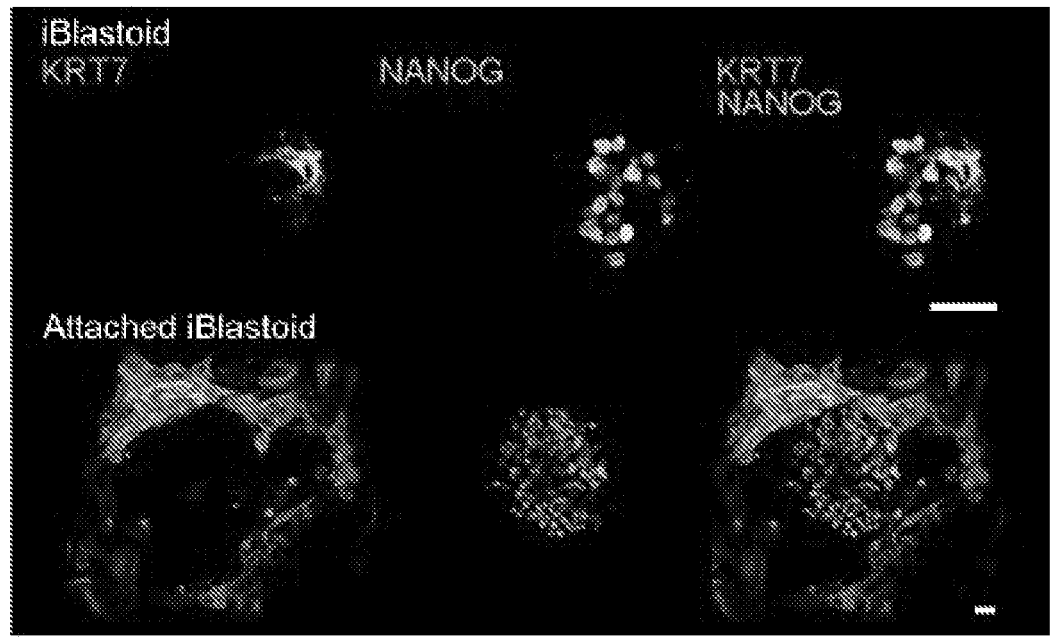
Figure 8:
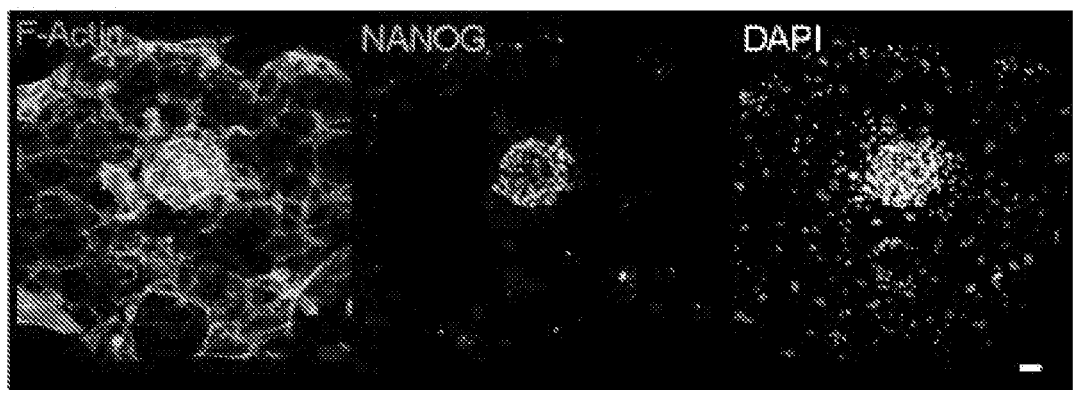
Figure 8:
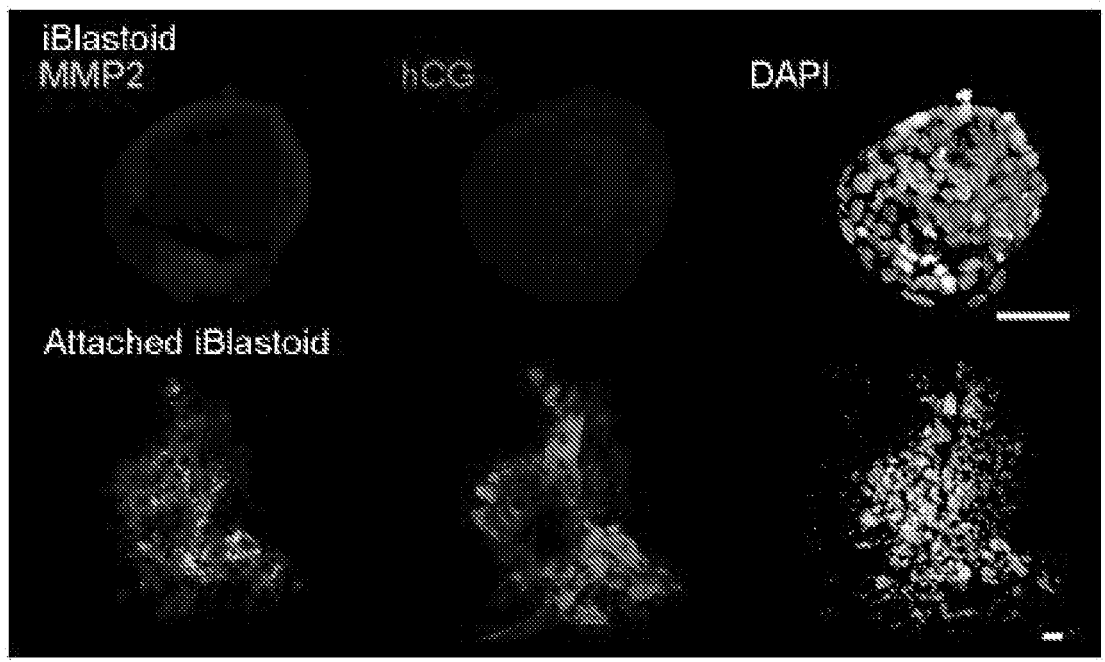

To rule-out molecular evidence of PS formation, the inventors performed a qRT-PCR 24 hr-time course of several key primitive streak markers (Xiang, L. et al. Nature 577, 537-542 (2020); Takahashi, K. et al. Nat. Commun. 5, 3678 (2014); Tyser, et al. bioRxiv (2020)) during the 5-day embryo attachment culture and did not observe up-regulation of TBXT, EOMES or MIXL1 or any morphological changes indicative of gastrulation (Tyser, Supra; O'Rahilly, R. & Muller, F. Developmental stages in human embryos: revised and new measurements. Cells Tissues Organs 192, 73-84 (2010); Yamaguchi, Y. & Yamada, S. Cells Tissues Organs 205, 314-319 (2018)) (FIG. 8b, FIG. 8a). Therefore, with 5-days of iBlastoid attachment culture, the EPI compartment did not progress to formation of a PS. Nevertheless, by stringently adhering to the above parameters, all subsequent human iBlastoid attachment culture experiments were performed for a total of 4.5 days after iBlastoid formation (FIG. 8a).

Example 2—Cell Culture Medium

Fibroblast medium: DMEM (ThermoFisher), 10% Fetal Bovine Serum (FBS, ThermoFisher), 1% Nonessential amino acids (ThermoFisher), 1 mM GlutaMAX™ (ThermoFisher), 1% Penicillin-streptomycin (ThermoFisher), 55 µM 2-mercaptoethanol (ThermoFisher) and 1 mM sodium pyruvate (ThermoFisher).

N2B27 basal medium: 50:50 mixture of DMEM/F-12 (ThermoFisher) and Neurobasal™ medium (ThermoFisher), supplemented with 2 mM L-Glutamine (ThermoFisher), 0.1 mM 2-mercaptoethanol (ThermoFisher), 0.5% N2 supplement (ThermoFisher), 1% B27 supplement (ThermoFisher), 1% Penicillin-streptomycin (ThermoFisher).

TSC basal medium: DMEM/F-12, GlutaMAX™ (ThermoFisher) supplemented with 0.3% BSA (Sigma), 0.2%

FBS (ThermoFisher), 1% ITS-X supplement (ThermoFisher), 0.1 mM 2-mercaptoethanol (ThermoFisher), 0.5% Penicillin-streptomycin (ThermoFisher), 1.5 pg/ml L-ascorbic acid (Sigma).

IVC1 medium: Advanced DMEM/F-12 (ThermoFisher), 1% ITS-X supplement (ThermoFisher), 2 mM L-Glutamine (ThermoFisher), 0.5% Penicillin-streptomycin (ThermoFisher), 20% Fetal Bovine Serum (FBS, ThermoFisher), 25 µM N-acetyl-L-cysteine (Sigma), 8 nM β-estradiol (Sigma) and 200 ng/ml progesterone (Sigma). IVC2 medium: Advanced DMEM/F-12 (ThermoFisher), 1% ITS-X supplement (ThermoFisher), 2 mM L-Glutamine (ThermoFisher), 0.5% Penicillin-streptomycin (ThermoFisher), 30% Knockout™ Serum Replacement (KSR, ThermoFisher), 25 µM N-acetyl-L-cysteine (Sigma), 8 nM P-estradiol (Sigma) and 200 ng/ml progesterone (Sigma).

Human iBlastoid medium: IVC1 medium, N2B27 basal medium and TSC basal medium in a respective 2:1:1 ratio supplemented with 2 µM CHIR99021 (Miltenyi Biotec), 0.5 µM A83-01 (Sigma), 1 µM SB431542, 0.8 mM Valproic acid (VPA, Sigma), 50 ng/ml EGF (Peprotech) and 1 Ong/ml BMP4 (Miltenyi Biotec).

| Media | Components | Company/Reference |
| --- | --- | --- |
| Fibroblast medium | DMEM | ThermoFisher |
| | 10% Fetal Bovine Serum (FBS) | ThermoFisher |
| | 1% Nonessential amino acids | ThermoFisher |
| | 1 mM GlutaMAX | ThermoFisher |
| | 1% Penicillin-streptomycin | ThermoFisher |
| | 55 µM 2-mercaptoethanol and | ThermoFisher |
| | 1 mM sodium pyruvate | ThermoFisher |
| MSC medium | MEM-alpha | ThermoFisher |
| | 16.67% Fetal Bovine Serum (FBS) | ThermoFisher |
| | 2 mM L-Glutamine | ThermoFisher |
| | 1% Penicillin-streptomycin | ThermoFisher |
| PBMC medium | StemPro-34 medium | ThermoFisher |
| | 2 mM L-Glutamine | ThermoFisher |
| | 1% Penicillin-streptomycin | ThermoFisher |
| | 100 ng/ml SCF | Miltenyi Biotec |
| | 100 ng/ml FLT-3L | Miltenyi Biotec |
| | 20 ng/ml IL-3 | Miltenyi Biotec |
| | 20 ng/ml IL-6 | Miltenyi Biotec |

Example 3—iBlastoids Generation by Reprogramming

All cell lines used in this study were authenticated, mycoplasma tested as described in the Reporting Summary. Primary human adult dermal fibroblasts (HDFa) from three different female donors were obtained from ThermoFisher (Catalogue number C-013-5C and lot #1029000 for 38F, lot #1528526 for 55F and lot #1569390 for 32F), cells were recovered and plated in medium 106 (ThermoFisher) supplemented with low serum growth supplement (LSGS) (ThermoFisher) for expansion.

Human somatic cell reprogramming was performed as previously described (Liu, X. et al. Nat. Methods 14, 1055-1062 (2017)) to obtain the d21 reprogramming intermediates. Briefly, reprogramming of human fibroblasts was conducted using CytoTune-iPS 2.0 Sendai reprogramming kit according to the manufacturer's instructions (ThermoFisher, lot #2170052). Primary HDFa were seeded at a density of ~5–10×10$^4$ cells in fibroblast medium. As shown in FIG. 1a, cells were transduced with Sendai viruses in FM at the multiplicity of infection (MOI) as follows, KOS (KLF4-OCT4-SOX2) MOI=5, c-MYC MOI=5, KLF4 MOI=6. Media replacement was done every other day starting from day 1 following transduction and every day from day 8 onwards. On day 21 of reprogramming, cells were dissociated and seeded at a density of 1.2×10$^5$ cells per well onto a 24-well Aggrewell™ plate (Stem Cell Technologies) in human iBlastoid medium supplemented with 10 µM Y-27632 (ROCK inhibitor, Selleckchem) according to the manufacturer's instructions. The cells were cultured in the incubators at 37° C., 5% 02 and 5% CO2. After 24 hours, the cells were replenished with fresh human iBlastoid medium without ROCK inhibitors. On day 6 of iBlastoid formation in the Aggrewell™, the iBlastoids were collected for subsequent analysis or in vitro attachment assay. Details of the culture medium used in the generation of iBlastoids are summarised in Example 2 above.

The inventors performed somatic cell reprogramming as previously described (Liu, X. et al. Nat. Methods 14, 1055-1062 (2017)), using integration-free Sendai viruses to deliver the OCT4/POU5F1, KLF4, SOX2, and c-MYC (OKSM) transcription factors (TFs) to obtain day 21 reprogramming intermediates. Alternatively, the inventors performed somatic cell reprogramming via mRNA transfection of transcription factors, as further described herein in Example 11. The inventors also demonstrated that alternative somatic cells can be reprogrammed using similar approaches, as described in Examples 12 and 13, thus establishing that reprogramming intermediates can be obtained from various somatic cells, and for use in the methods of the present invention.

When the intermediates were transferred to the AggreWell™ system in a medium containing WNT activators, TGF-3 inhibitors, HDAC inhibitors, EGF, and BMP4 (see Methods) (FIG. 1a), the intermediates started to form aggregates, and from day 3 cavitated and gradually enlarged (FIG. 2b). Blastocyst-like structures became evident by day 5 to 6 (FIG. 1b) and immunofluorescence staining of the structures for NANOG revealed an inner cell mass (ICM)-like cellular compartment with NANOG-positive cells, with a blastocoel-like cavity surrounded by an outer layer of NANOG-negative cells (FIG. 1c). Since these structures were directly derived via reprogramming of somatic cells, they were termed "human induced blastoids" (iBlastoids). Moreover, measurements of x- and y-axis diameter, x:y aspect ratio as well as projection area of the iBlastoids revealed that they had a comparable size to previously published measurements of human blastocysts at embryonic day 5-7 (E5-7) post-fertilization (FIG. 1d-h). In addition, the cell number in the iBlastoids ranged from 100 to 400, with a median of approximately 280 cells. Although the median cell number is slightly greater than the reported (approximated average of 240 cells) for human blastocysts at E5-7, it is still within the range previously reported for E5-7 blastocysts (FIG. 1i). In order to quantify the efficiency of iBlastoid formation, 100 random structures were counted and 14% were found to exhibit the typical blastocyst-like morphology including a blastocoel cavity (FIG. 2c). During iBlastoid formation in the AggreWell™ system, adhering cell clusters, that were not part of the iBlastoids, were consistently observed along the edge of microwells. It was hypothesized that these were refractory fibroblasts from the reprogramming culture (FIG. 2d). To validate this, those cell clusters were isolated and cultured in fibroblast medium, resulting in the propagation of cells with a classic fibroblast morphology (FIG. 2d). This suggested that these reprogramming-refractory fibroblasts did not contribute to the iBlastoid formation. Scoring of the iBlastoids using the IVF blastocyst quality criteria (Good=1, Fair=2 or Poor=3) (in accordance with the approach described in The Istanbul consensus workshop on embryo assessment: proceedings of an expert meeting. *Hum. Reprod.* 26, 1270-1283 (2011), indicated iBlastoids were graded as good or fair with an average score of 1.75 for ICM and 1.67 for TE (FIG. 2i-k).

In summary, these data demonstrate that reprogramming intermediates can be used to directly generate human blastocyst-like structures, named 'iBlastoids' that are structurally similar to blastocysts.

Example 4—iBlastoid Characterisation Materials and Methods

Immunofluorescence Staining iBlastoids/cells were fixed in 4% Paraformaldehyde (PFA, Sigma), permeabilized with 0.5% Triton® X-100 (Sigma) in DPBS (ThermoFisher) and blocked with blocking buffer (3% bovine serum albumin (BSA) (Sigma)+0.1% Tween-20 (Sigma) in DPBS (ThermoFisher)). All antibodies used in this study are listed in the below table:

| Antibody name | Supplier | Catalog # |
| --- | --- | --- |
| Mouse anti-GATA2 IgG21 + A4 + A2:A24 | Sigma-Aldrich | Cat#WH0002624M1 |
| Rabbit anti-CK7 (KRT7) IgG | abcam | Cat#ab181598 |
| Mouse anti-CDX2 IgG1 | abcam | Cat#ab157524 |
| Rabbit anti-CDX2 IgG | Cell Signaling Technology | Cat#12306 |
| Rabbit anti-NANOG polyclonal | abcam | Cat#ab21624 |
| Mouse anti-NANOG IgG1 | Invitrogen | Cat#14-5768-82 |
| Mouse anti-OCT3/4 IgG2b | Santa Cruz Biotechnology | Cat#sc-5279 |
| Mouse anti-SOX17 IgG1 | abcam | Cat#ab84490 |
| Rat anti-SOX2 IgG2a | Invitrogen | Cat#14-9811-82 |
| Goat anti-GATA6 polyclonal | R&D Systems | Cat#AF1700 |
| Rabbit anti-MMP2 IgG | Cell Signaling Technology | Cat#40994 |
| Mouse anti-hCG IgG1 | abcam | Cat#ab9582 |
| Alexa Fluor™ 488 Phalloidin | ThermoFisher | Cat# A-12379 |
| Goat anti-rat IgG AF555 secondary | ThermoFisher | Cat#A-21434 |
| Goat anti-rabbit IgG AF555 secondary | ThermoFisher | Cat#A-21428 |
| Goat anti-mouse IgG2b AF647 secondary | ThermoFisher | Cat#A-221242 |
| Goat anti-mouse IgG- AF488 secondary | ThermoFisher | Cat#A-11029 |
| Goat anti-mouse IgG1- AF488 secondary | ThermoFisher | Cat#A-21121 |
| Goat anti-mouse IgG2a- AF488 secondary | ThermoFisher | Cat#A-21131 |
| Goat anti-mouse IgG2a- AF647 secondary | ThermoFisher | Cat#A-21241 |
| Donkey anti-mouse IgG-488 secondary | ThermoFisher | Cat#A-21202 |
| Donkey anti-goat IgG-555 secondary | ThermoFisher | Cat#A-21432 |
| Donkey anti-rabbit IgG-647 secondary | ThermoFisher | CatA-31573 |

For example, primary antibodies used: rabbit anti-NANOG polyclonal (1:100, Abcam), mouse anti-CDX2 IgG1 (1:50, Abcam) prepared in blocking buffer. Primary antibody incubation was conducted overnight at 4° C. on shakers followed by rtp incubation with secondary antibodies (1:500 in blocking buffer) for 3 hours. Secondary antibodies used in this study were goat anti-rabbit IgG AF555 (1:500, ThermoFisher) or goat anti-rabbit IgG AF647 (1:500, Invitrogen) for NANOG, goat anti-mouse IgG AF488 (1:400, ThermoFisher) or goat anti-mouse IgG AF488 (1:500, ThermoFisher) for CDX2. After labeling, iBlastoids/cells were stained with 4',6-Diamidino-2-Phenylindole, Dihydrochloride (DAPI, ThermoFisher) at a concentration of 5 pg/ml in a blocking buffer for 1 hour. Images were taken using a SP8 inverted confocal microscope (Leica) or LSM780 multiphoton confocal microscope (Zeiss).

Confocal Imaging and Analysis

Immunostained iBlastoids were imaged using a SP8 inverted confocal microscope (Leica) or a laser scanning confocal (LSM 780 microscope, Zeiss) with a water UV-VIS-IR Apochromat 40×1.2 NA objective and highly sensitive avalanche photodiode light detectors of the Confocor 3 module (Zeiss). 3D visualizations of iBlastoids were performed using Imaris 9.5 software (Bitplane AG). The manual surface rendering module was used for cell and iBlastoid segmentation. Final images were processed and assembled using Adobe Photoshop or ImageJ.

Fluorescence-Activated Cell Sorting (FACS)

iBlastoids were dissociated with TrypLE™ Express (ThermoFisher), and DPBS (ThermoFisher) supplemented with 2% FBS (ThermoFisher) and 10 µM Y-27632 (Selleckchem) was used for final resuspension of the samples. Dissociated cells were pelleted at 400×g for 5 mins and then resuspended in a final volume of 500 µl with propidium iodide (PI) (Sigma) added to a concentration of 2 pg/ml. Cell sorting was carried out with a 100 µm nozzle on an Influx instrument (BD Biosciences).

Quantitative RT-PCR

RNA was extracted from cells using RNeasy® micro kit (Qiagen) or RNeasy® mini kit (Qiagen) and QIAcube® (Qiagen) according to the manufacturer's instructions. Reverse transcription was then performed using SuperScript™ µl cDNA Synthesis Kit (ThermoFisher) or QuantiTect® reverse transcription kit (Qiagen, Cat no. 205311), real-time PCR reactions were set up in triplicates using QuantiFast® SYBR Green PCR Kit (Qiagen) and then carried out on the 7500 Real-Time PCR system (ThermoFisher). In The qRT-PCR primers used in this study are shown in the below table:

| Gene name | Primer name | Sequence |
| --- | --- | --- |
| hGAPDH | Forward | CTGGGCTACACTGAGCACC |
| | Reverse | AAGTGGTCGTTGAGGGCAATG |
| CSH1 | Forward | CATGACTCCCAGACCTCCTTCT |
| | Reverse | ATTTCTGTTGCGTTTCCTCCAT |
| ITGA1 | Forward | GCTCCTCACTGTTGTTCTACG |
| | Reverse | CGGGCCGCTGAAAGTCATT |
| TBXT | Forward | TATGAGCCTCGAATCCACATAGT |
| | Reverse | CCTCGTTCTGATAAGCAGTCAC |
| EOMES | Forward | GTGCCCACGTCTACCTGTG |
| | Reverse | CCTGCCCTGTTTCGTAATGAT |
| MIXL1 | Forward | GGCGTCAGAGTGGGAAATCC |
| | Reverse | GGCAGGCAGTTCACATCTACC |

Mesoderm Differentiation

Positive control for qRT-PCR of primitive streak markers was obtained by modifying a previously published mesoderm differentiation protocol (Lam, A. Q. et al. J. Am. Soc.

Nephrol. 25, 1211-1225 (2014)). Briefly, human iPSCs grown in E8 Medium (ThermoFisher) at 50% confluency was replaced with a culture medium consisted of RPMI, GlutaMAX™ (ThermoFisher), 1% B27 supplement (ThermoFisher), 1% Penicillin-streptomycin (ThermoFisher) and 5 µM CHIR99021 (Miltenyi Biotec). After 48 hours, the differentiated cells were collected for qRT-PCR analysis, which highly expressed the primitive streak markers TBXT, EOMES and MIXL1 (FIG. 8b).

hCG ELISA

Generation of iBlastoids and in vitro attachment assay were performed as described in the 'in vitro attachment assay' Example, below. The medium was collected for both iBlastoids (day 6) and attached iBlastoids (day 6+4.5) and stored at −80° C. The hCG level within the media was measured using hCG ELISA kit (Abnova, ABNOKA4005) according to the manufacturer's instructions.

Single Cell RNA-Sequencinq (scRNA-Seq) of iBlastoids

For scRNA-seq experiments, iBlastoids were dissociated to obtain single cell suspension for FACS as described in the above section. Cells subjected to FACS were sorted for PI-negative, non-debris live single cells for scRNA-seq. The collected cells were isolated, encapsulated and constructed using Chromium controller (10×Genomics) as per the manufacturer's instructions "Chromium Next GEM Single Cell 3' Reagent Kit V3.3 User Guide". Sequencing was done on an Illumina NovaSeq 6000 using a paired-end (R1 28 bp and R2 87 bp) sequencing strategy and aiming for 20,000 read-pairs per cell. Chromium barcodes were used for demultiplexing and FASTQ files were generated from the mkfastq pipeline using the Cellranger program (v3.1.0, http://software.10xgenomics.com/single-cell/overview/welcome). Alignment and UMI counting were performed using Cellranger, which utilises the STAR aligner (Dobin, A. et al. Bioinformatics 29, 15-21 (2013)) to map sequencing reads to a custom version of the Ensembl GRCh37.87 reference genome, which we expanded by sequences of the custom SENDAI KLF4, MYC, and SEV (KOS) vectors. This step results in 9060 unique cell barcodes.

iBlastoid scRNA-Seq Cell Donor Identification

To determine the individual donor identity of every cell, the Bayesian demultiplexing tool Vireo (v 0.3.2) was employed (Huang, Genome Biol. 20, 273 (2019)). Briefly, the inventors compiled expressed alleles in the single-cell data using cellSNP (v 0.3.0) to generate a list of single nucleotide polymorphisms (SNPs) with a minimum allele frequency (using the argument minMAF) of 0.1 and minimum unique molecular identifiers (using the argument minCOUNT) of 20. Furthermore, cellSNP requires a reference list of human variants to call the SNPs and the inventors used a pre-compiled list of SNPs from the 1000 genome project provided by the authors of Vireo (downloaded from https://sourceforge.net/projects/cellsnp/files/SNPlist/). In particular, the list of variants based on the hg19 genome with minor allele frequency>0.05, containing 7.4 million SNPs was used. Subsequently, Vireo was performed to demultiplex the single-cell library by separating the cells into two donor populations. Note that Vireo is only able to distinguish the cells with respect to the two donors, but is unable to assign the exact donor identity (32F or 38F) to each cell.

iBlastoid scRNA-Seq Cell Calling, Quality Control

Quality control was first performed at the cell level. Cells with (i) evidence for both or neither cell line donor, (ii) low number of expressed genes [nGene], or (iii) high percentage mitochondrial genes [pctMT] were discarded. Cutoffs nGene<1,300 pctMT>15 were applied to discard cells. Next, quality control was performed at the gene level. Genes were filtered if not presenting in at least 50 cells with at least 1 read each. All cutoffs were determined after investigating the distributions of each variable. After quality control, 6858 cells and 14224 genes remain for the scRNA-seq.

iBlastoid scRNA-Seq Analysis

Analyses in the remainder of the section were conducted using R (v3.6)55 with Seurat (v3.1.5)(Butler, et al. Nat. Biotechnol. 36, 411-420 (2018); Stuart, T. et al. Cell 177, 1888-1902.e21 (2019)). Bioinformatics plots were generated using ggplot2 (v3.3.1)58, and heatmaps with pheatmap (v1.0.12) (Kolde, R. & Vilo, J. F1000Research vol. 4 574 (2015)). The SCTransform function (Hafemeister, C. & Satija, R. Genome Biol. 20, 296 (2019)) in Seurat was used to scale and normalise the data. Following Principle component analysis (PCA), a uniform manifold approximation (UMAP) was generated using 20 dimensions. Unsupervised clustering was performed using the FindClusters function with a resolution of 0.2, resulting in 7 individual clusters. Differentially expressed genes between clusters (cluster markers) were identified with the FindAllMarkers function, employing a Wilcoxon rank sum test and a minimum up-regulation of 0.25 log-fold. Average over-expression of cell type signatures (EPI, TE, PE, non-reprogramming (NR) were calculated with the AddModuleScore function and gene signatures published by Petropoulos, S. et al. Cell 165, 1012-1026 (2016) and Liu et al (Nature 2020 Sep. 16.doi: 10.1038/s41586-020-2734-6), respectively. Cell types were assigned to clusters manually using canonical markers, Petropoulos and Liu signatures as evidence. Remaining cell populations were labelled "intermediate" (IM) and enumerated (Rossant, J. & Tam, P. P. L. Cell Stem Cell vol. 20 18-28 (2017); Harrison, et al. Science 356, (2017); Sozen, B. et al. Nat. Cell Biol. 20, 979-989 (2018)). Finally, cell cycle scores were calculated using the cyclone function (Scialdone, A. et al. Methods 85, 54-61 (2015)) from the scran package, and cell phase assigned according to the highest probability.

Integrated scRNA-Seq Analysis

Previously published single cell data sets from Petropoulos, S. et al. Cell 165, 1012-1026 (2016) (Petropoulos) and Blakeley, P. et al. Development 142, 3613 (2015) (Blakeley) were integrated with the iBlastoids data published here. First, cells from the NR cluster are removed as irrelevant to this integration from the iBlastoid data. Petropoulos' 1529 cells total were filtered for blastocyst cells, removing the pre-blastocyst stages leaving 1096 E5-E7 EPI, TE, and PE cells. Petropoulos' data and Blakeley's 30 cells were processed using SCTransform. Both datasets were integrated into the iBlastoids data after identifying integration genes (FindIntegrationAnchors and IntegrateData) using 4000 anchor genes derived from the SCT assays. The integrated dataset has 7861 cells, 23308 genes, and 4000 integrated genes. PCA and UMAP (20 dimensions) are used for dimensionality reduction and FindClusters to identify clusters (resolution 0.2). Cluster identities for 5 individual clusters were assigned manually using co-localisation of cell identities from all three datasets as evidence, as well as marker and signature expression. Transcriptome correlation was calculated using the integrated gene expression values and Pearson correlation on mean values of gene expression across all cells of a) the same original cell identity (cluster id for iBlastoids, EPI, TE, PE for Blakeley, E5-7 EPI, TE, PE for Petropoulos), or b) the same cell type (aggregates of all EPI, TE, PE cells and, additionally, IM for iBlastoids).

In Vitro Attachment Assay

Generation of iBlastoids was performed as described in Example 3 above. The in vitro attachment assay (which is often used as a model of embryo implantation) was performed by adapting to a previously published protocol (Shahbazi, et al. Nat. Cell Biol. 18, 700-708 (2016); Deglincerti, A. et al. Nature 533, 251-254 (2016)). Briefly, iBlastoids derived were transferred onto optical-grade tissue culture plates (Eppendorf) and cultured in IVC1 media at 37° C., 5% $O_2$ and 5% CO2 incubators. On day 2 of attachment assay, the culture media was switched to IVC2 media. iBlastoids were cultured up to day 4.5 in the attachment assay and collected for analysis. Details of the culture medium used in the in vitro attachment assay are summarised in Example 2.

Statistics and Reproducibility

The day 21 fibroblast reprogramming intermediates scRNA-seq data obtained from a previous study (Liu et al (Nature 2020 Sep. 16.doi: 10.1038/s41586-020-2734-6) was reanalyzed for FIG. 2a, with 4,761 cells. For the iBlastoid scRNA-seq data, a total of 6858 cells obtained from n=2 biological replicates were included in all the analysis used in this study. For the scRNA-seq dataset of human blastocysts used in this study, a total of 1096 cells were adapted from Petropoulos dataset and a total of 30 cells were adapted from Blakeley dataset for analysis. For the iBlastoids and human blastocyst integrated dataset, a total of 7861 cells were used for analysis. For FIG. 1b, iBlastoids were generated from 3 different donor fibroblasts of 2 independent reprogramming experiments (n=5 biological replicates) and representative images were shown in the figure. For FIG. 1c, immunostaining was performed on iBlastoids from 3 different donors of 2 independent reprogramming experiments (n=5 biological replicates) with similar results obtained and representative images were shown in the figure. For FIG. 1e-h, data of human blastocysts was referenced from 8 publications (n=8) while the quantification of various parameters on iBlastoids was each done on 18 independent iBlastoids obtained from 3 different donors (n=18 biological replicates). For FIG. 1i, cell number quantification was performed on 14 independent iBlastoids obtained from 3 different donors (n=14 biological replicates). For FIG. 1j-1, immunostaining was performed on iBlastoids from 3 different donors of 2 independent reprogramming experiments (n=5 biological replicates) with similar results obtained and representative images were shown in the figure. For FIG. 1m, immunostaining was performed on iBlastoids from 3 different donors (n=3 biological replicates) with similar results obtained and representative images were shown in the figure. For FIG. 1n-r, immunostaining was performed on iBlastoids from 2 different donors (n=2 biological replicates) with similar results obtained and representative images were shown in the figure. A dense Keratin 8 (KRT8) filament network with the outer TE-like cells was also observed in the iBlastoids, consistent with what is typically observed in blastocysts (FIG. 1s).

For FIG. 7a, an in vitro attachment assay was performed using iBlastoids derived from 3 different donor fibroblasts of 2 independent reprogramming experiments (n=5 biological replicates) and representative images were shown in the figure. For FIG. 7b-c, immunostaining was performed on iBlastoids from 2 different donors (n=2 biological replicates) with similar results obtained and representative images were shown in the figure. For FIG. 7e, immunostaining was performed on iBlastoids from 2 different donors of 2 independent reprogramming experiments (n=4 biological replicates) with similar results obtained and representative images were shown in the figure. For FIG. 7f-g, immunostaining was performed on iBlastoids from 2 different donors (n=2 biological replicates) with similar results obtained and representative images were shown in the figure. For FIG. 7h, fold change expression of CSH1 and ITGA1 were measured in n=5 independent experiments with technical replicates. Data are represented as mean±s.e.m. For FIG. 7i, hCG ELISA was done in n=4 independent experiments with technical replicates. Data are represented as mean±s.e.m. For FIG. 2b, iBlastoids were generated from three different donor fibroblasts of 2 independent reprogramming experiments (n=5 biological replicates) and representative images were shown in the figure. For FIG. 2c, quantification of the iBlastoid efficiency was done by counting 100 independent 3D structures obtained (n=100 biological replicates). For FIG. 2d, the experiment was performed with n=3 biological replicates from 3 different donors with similar results obtained and representative images were shown in the figure. For FIG. 2e, immunostaining was performed on iBlastoids from 3 different donors of 2 independent reprogramming experiments (n=5 biological replicates) with similar results obtained and representative images were shown in the figure. For FIG. 2f-g, immunostaining was performed on iBlastoids from 2 different donors (n=2 biological replicates) with similar results obtained and representative images were shown in the figure. For FIG. 8b, fold change expression of TBXT, EOMES, MIXL1 were measured in n=6 independent experiments from 2 donors with technical replicates. Data are represented as mean±s.e.m. For FIG. 8c, immunostaining was performed on iBlastoids from 3 different donors of 2 independent reprogramming experiments (n=5 biological replicates) with similar results obtained and representative images were shown in the figure. For FIG. 8d, immunostaining was performed on iBlastoids from 3 different donors (n=3 biological replicates) with similar results obtained and representative images were shown in the figure. For FIG. 8e-f, immunostaining was performed on iBlastoids from 2 different donors (n=2 biological replicates) with similar results obtained and representative images were shown in the figure.

Example 5—iBlastoid Characterisation Results

To further confirm the identity and spatial localization of the cells within the iBlastoids, the inventors performed co-immunostaining of the EPI marker NANOG and the TE marker CDX2. They then applied confocal imaging and analysis to obtain a 3-dimensional (3D) representation of iBlastoids. The results indicate that NANOG positive cells are located exclusively in the ICM-like compartments, whereas CDX2 positive cells are found in the outer layer resembling the TE (FIG. 1j).

The 3D reconstruction and overlay of Differential Interference Contrast (DIC) and fluorescence images confirmed the spatial localization of NANOG positive and CDX2 positive cells, as well as confirming the existence of a blastocoel-like cavity formed in the iBlastoid structures similar to blastocysts (Shahbazi, M. N. et al. Nat. Cell Biol. 18, 700-708 (2016), Deglincerti, A. et al. Nature 533, 251-254 (2016); Xiang, L. et al. Nature 577, 537-542 (2020) (FIG. 1k, l). Consistent with the origins of the iBlastoids structures (ie, being derived from reprogrammed fibroblasts), no zona pellucida was observed. Importantly, the inventors were able to confirm these results from iBlastoids generated from two additional fibroblast donors in multiple rounds of iBlastoid generations (FIG. 2e).

To further characterize the EPI and TE-like cells of the iBlastoids, the inventors tested a combination of two additional EPI markers (OCT4, also called POU5F1, and SOX2) and a TE marker (GATA2) in the iBlastoids. As described for human blastocysts (Fogarty, N. M. E. et al. Nature 550, 67-73 (2017); Boroviak, T. et al. Development 145, (2018)), the outer TE-like cells were GATA2 positive whereas significant colocalization of OCT4 and SOX2 was found in the ICM-like compartments (FIG. 1m). To evaluate the presence of PE-like cells in the iBlastoids, the inventors first performed immunostaining of SOX17, a PE marker, alongside GATA2 (TE marker) and NANOG (EPI marker). Within the ICM-like compartment, the inventors identified SOX17 positive cells at the periphery of the NANOG positive cells (FIG. 1n, FIG. 2f), similar to what has previously been reported for E6-7 blastocysts (Xiang supra; Wamaitha, S. E. et al. Nat. Commun. 11, 764 (2020)).

Figure 10:
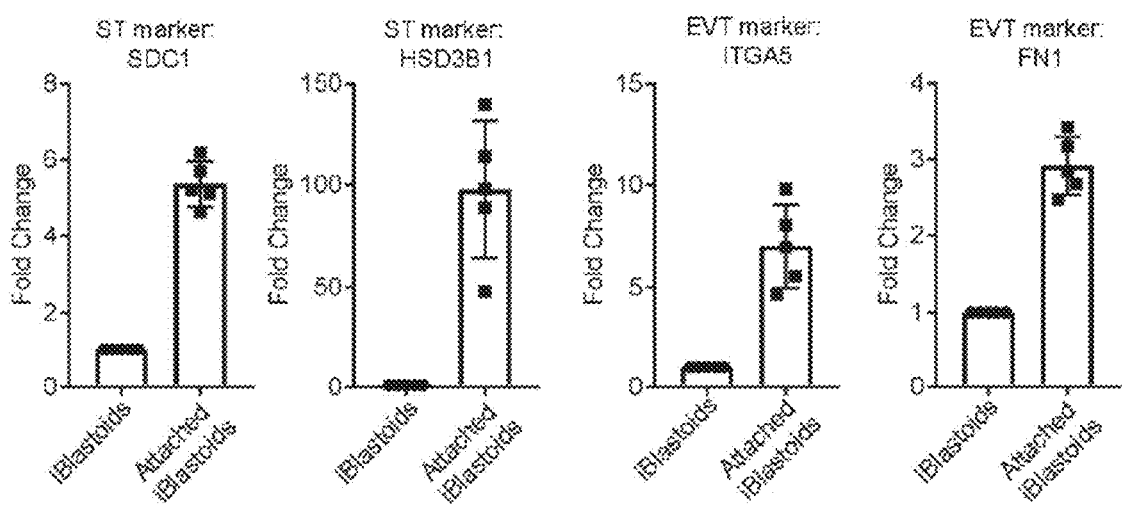
FIG. 10. Characterisation of attached iBlastoids. qRT-PCR analysis of ST markers (SDC1, HSD3B1) and EVT markers (ITGA5, FN1) in attached iBlastoids, mean±s.e.m., n=5.

For further validation, the inventors performed additional immunostaining using another PE marker, GATA6, in combination with CDX2 (TE marker) and OCT4 (EPI marker). They noticed a "salt and pepper" pattern in the TE-like compartment as indicated by the co-localization of GATA6 with CDX2 staining (FIG. 10, FIG. 2g). Although initially puzzling, this pattern has previously been reported, where GATA6 has also been ubiquitously detected in E6-7 human blastocysts (Deglincerti, Supra; Roode, M. et al. Human hypoblast formation is not dependent on FGF signalling. Dev. Biol. 361, 358-363 (2012); Kuijk, E. W. et al. The roles of FGF and MAP kinase signaling in the segregation of the epiblast and hypoblast cell lineages in bovine and human embryos. Development 139, 871-882 (2012)). Importantly, upon closer examination, the inventors observed GATA6 positive cells (with low or weak CDX2 staining) neighbouring OCT4 positive cells in the ICM-like compartment, suggesting the possible presence of GATA6 positive PE-like cells in the iBlastoids (FIG. 10).

In human blastocysts, cells of the TE and EPI lineages have a clear difference in cellular morphology, where TE cells show a "classic" elongated epithelial morphology whereas EPI cells are smaller and compacted due to the constraints of the ICM (Kovacic, B., Vlaisavljevic, V., Reljic, M. & Cizek-Sajko, M. Reprod. Biomed. Online 8, 687-694 (2004)). To examine whether there were any differences in the cellular morphology of EPI-like and TE-like cells in the iBlastoids, the inventors utilized the cell membrane marker F-Actin (also called Phalloidin) on the iBlastoids to visualize cellular architecture (FIG. 1p-r). The results indicate that the compact NANOG positive EPI-like cells had a more rounded columnar appearance, whereas the TE-like cells surrounding the blastocoel cavity were flattened, highlighting that this model is able to recapitulate differences in the cellular architecture of EPI and TE cells (FIG. 1q). Altogether, these results demonstrate that iBlastoids display the main morphological features of human blastocysts at E6-7, and can also model the key molecular and spatial aspects of EPI, TE and PE cells.

Example 6—Single-Cell Transcriptomic Profiling of iBlastoids

Figure 3:
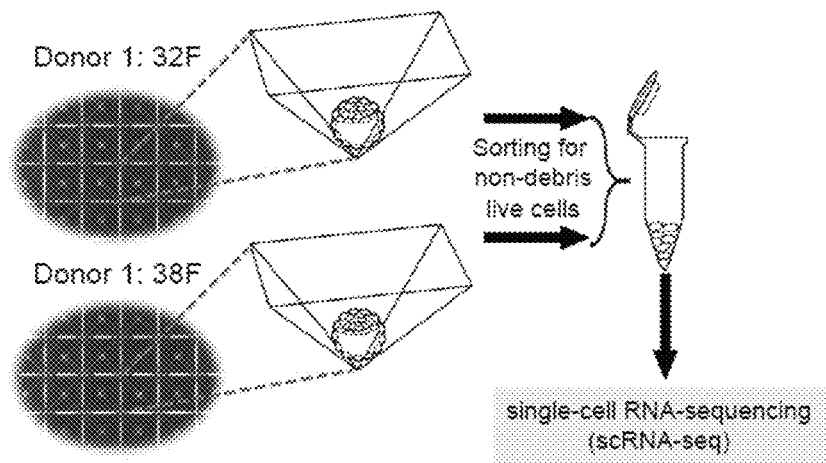
FIG. 3. Single-cell transcriptomic profiling of iBlastoids. *a*, Experimental design for scRNA-seq experiment using iBlastoids. *b*, Expression of EPI markers (POU5F1 and NANOG), TE markers (CDX2 and GATA2), and PE markers (SOX17 and GATA6) for 6858 cells from iBlastoid scRNA-seq library. *c*, Per cell expression score for EPI, TE, and EPI signatures on UMAP of iBlastoid scRNA-seq dataset. *d*, Unsupervised clustering of iBlastoid dataset with assigned cluster names. *e*, UMAP projection of integrated datasets showing iBlastoid EPI, TE, and PE cells together with EPI, TE, and PE cells from blastocysts (Blakeley and Petropoulos). *f*, Per cell expression score of EPI, TE, and PE signatures of integrated dataset. *g*, Unsupervised clustering of the integrated dataset with assigned cluster names. *h*, Proportion of cells for iBlastoids and human blastocyst datasets (Blakeley and Petropoulos) within each integrated cluster with respective original cell ID prior to integration analysis. *i*, Pearson correlation analysis of iBlastoid EPI, TE, and PE clusters with annotated EPI, TE, and PE clusters from blastocysts (Blakeley and Petropoulos). *j, k*, Per cell expression score of defined mural and polar TE signatures on iBlastoid scRNA-seq TE cluster. *l*, Binned subtype score for mural and polar TE signatures along UMAP component 1. *m*, Immunostaining of iBlastoids for CCR7, n=4. Scale bar, 20 μm. *n*, CCR7 fluorescence intensity of polar and mural TE on iBlastoids, n=4. The line within each box represents the median and the whiskers represent the maxima and minima respectively.
Figure 3:
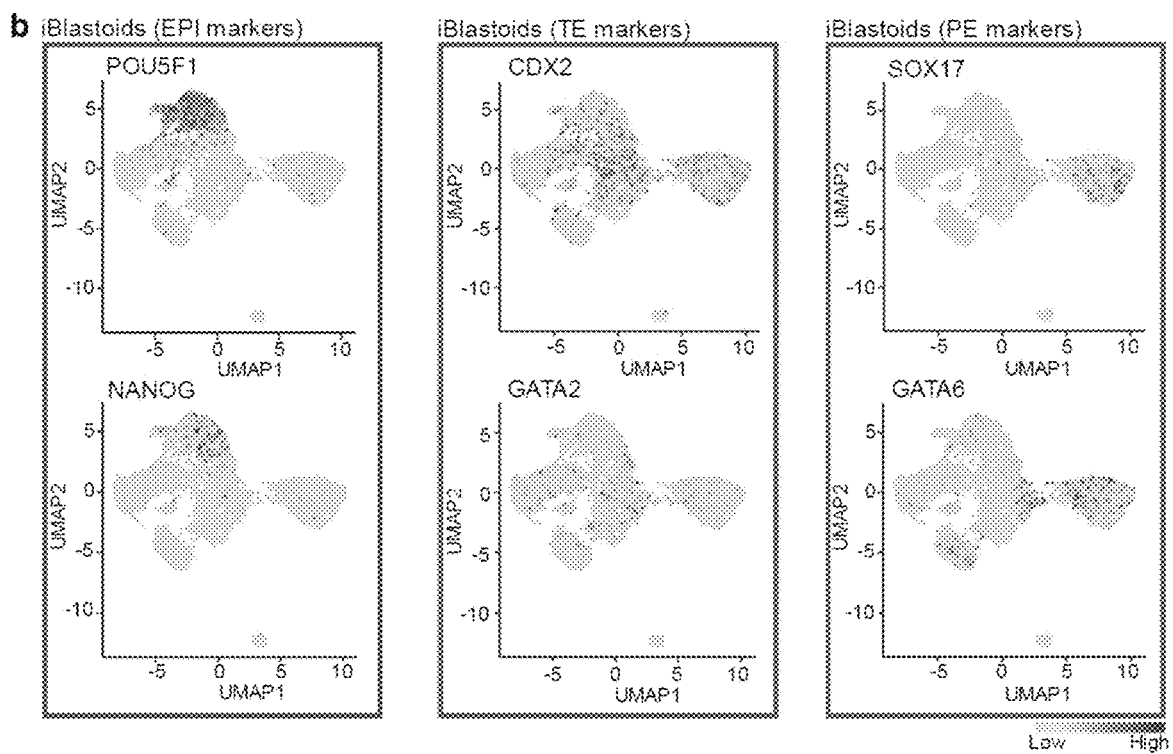
Figure 3:
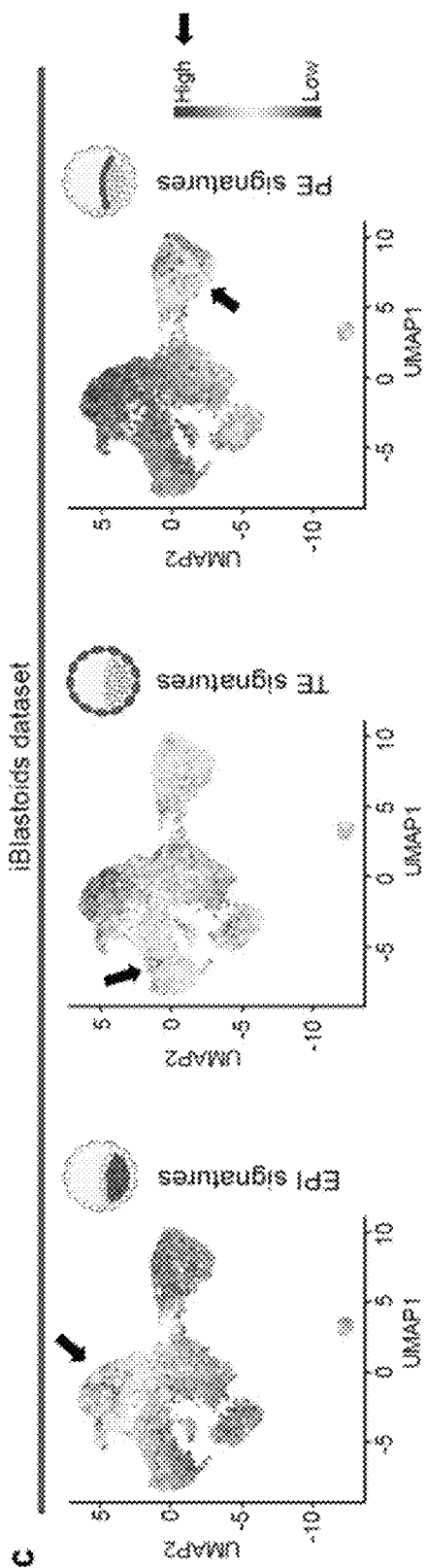
Figure 3:
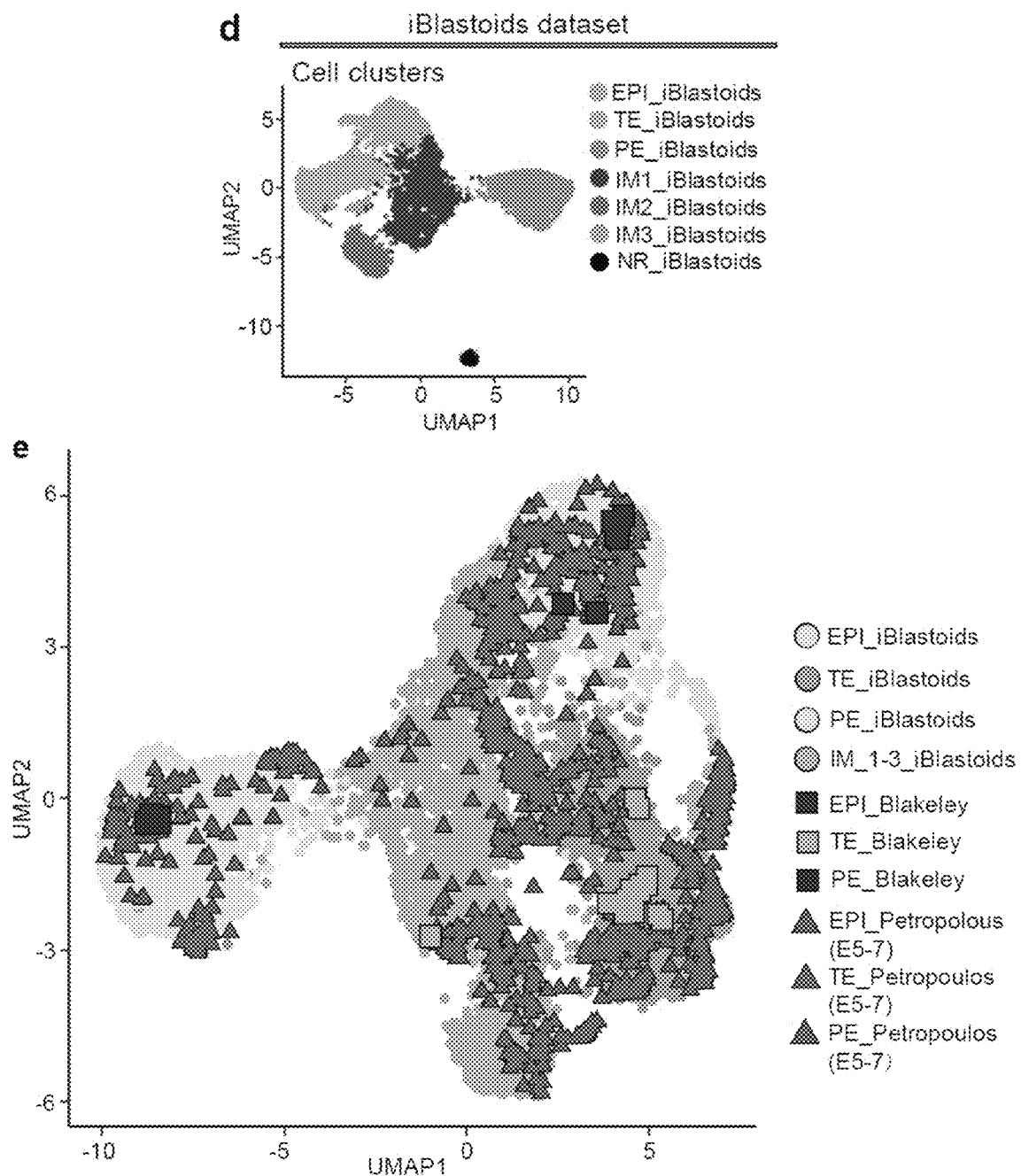
Figure 3:
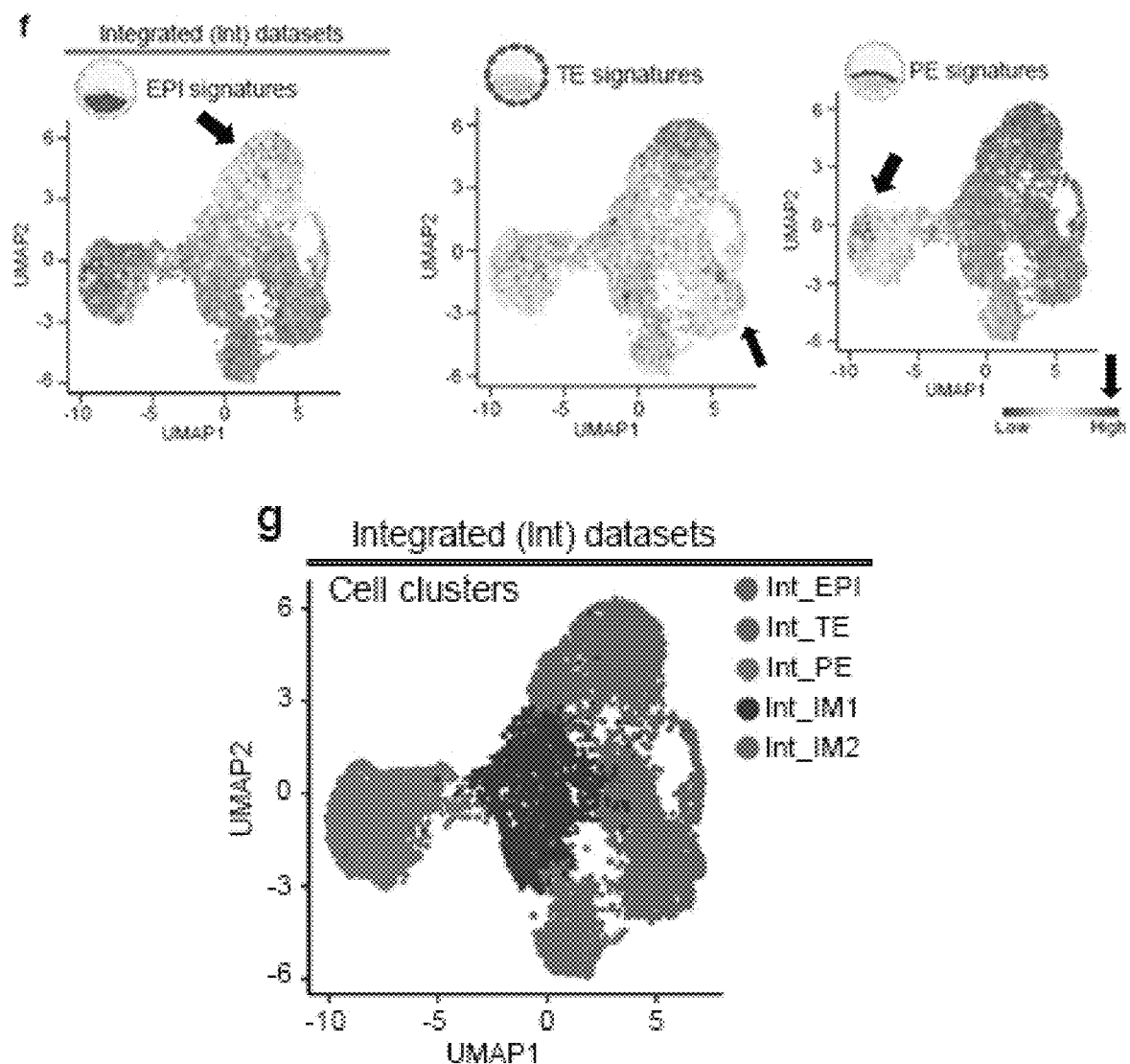
Figure 3:
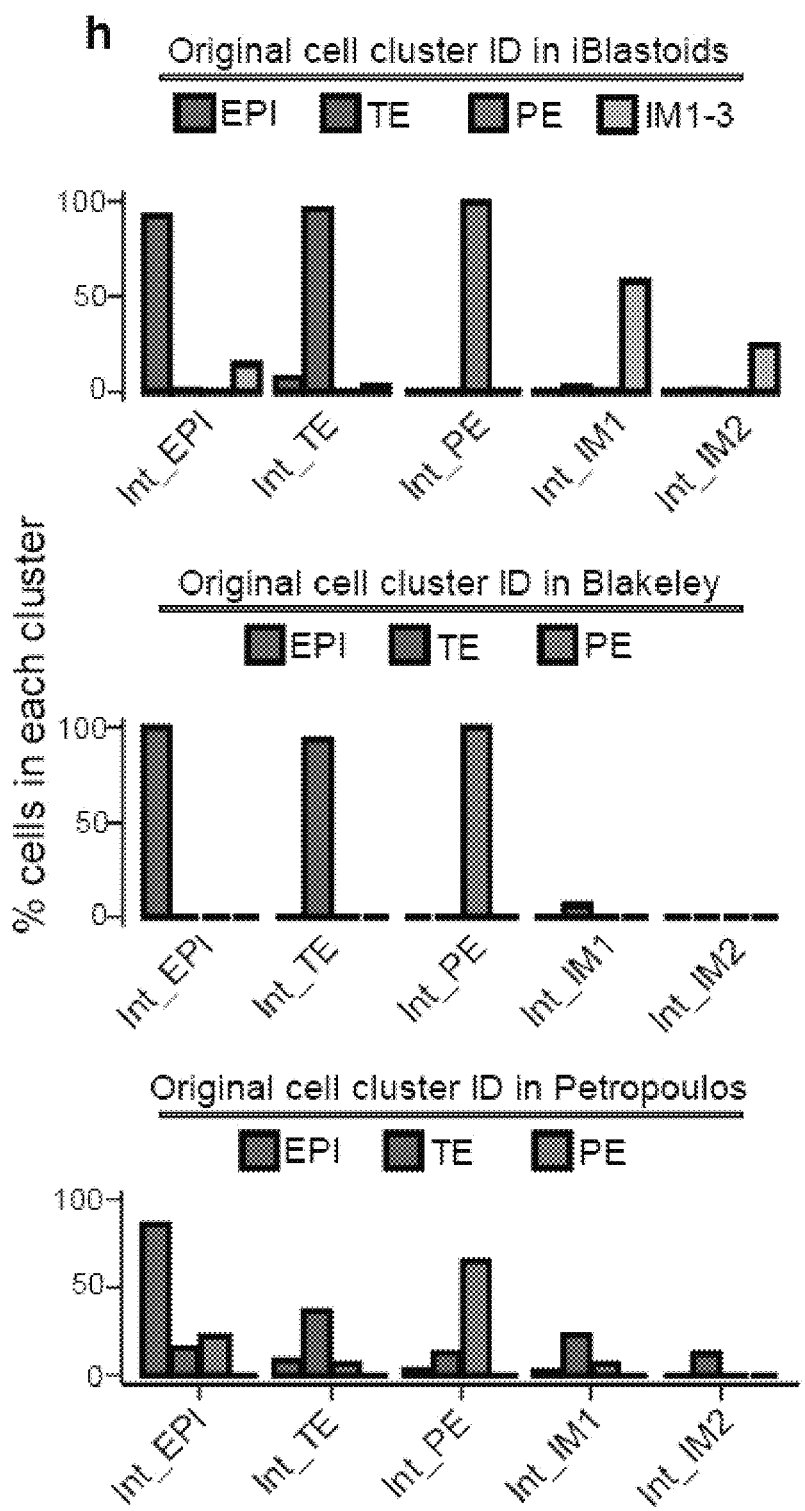
Figure 3:
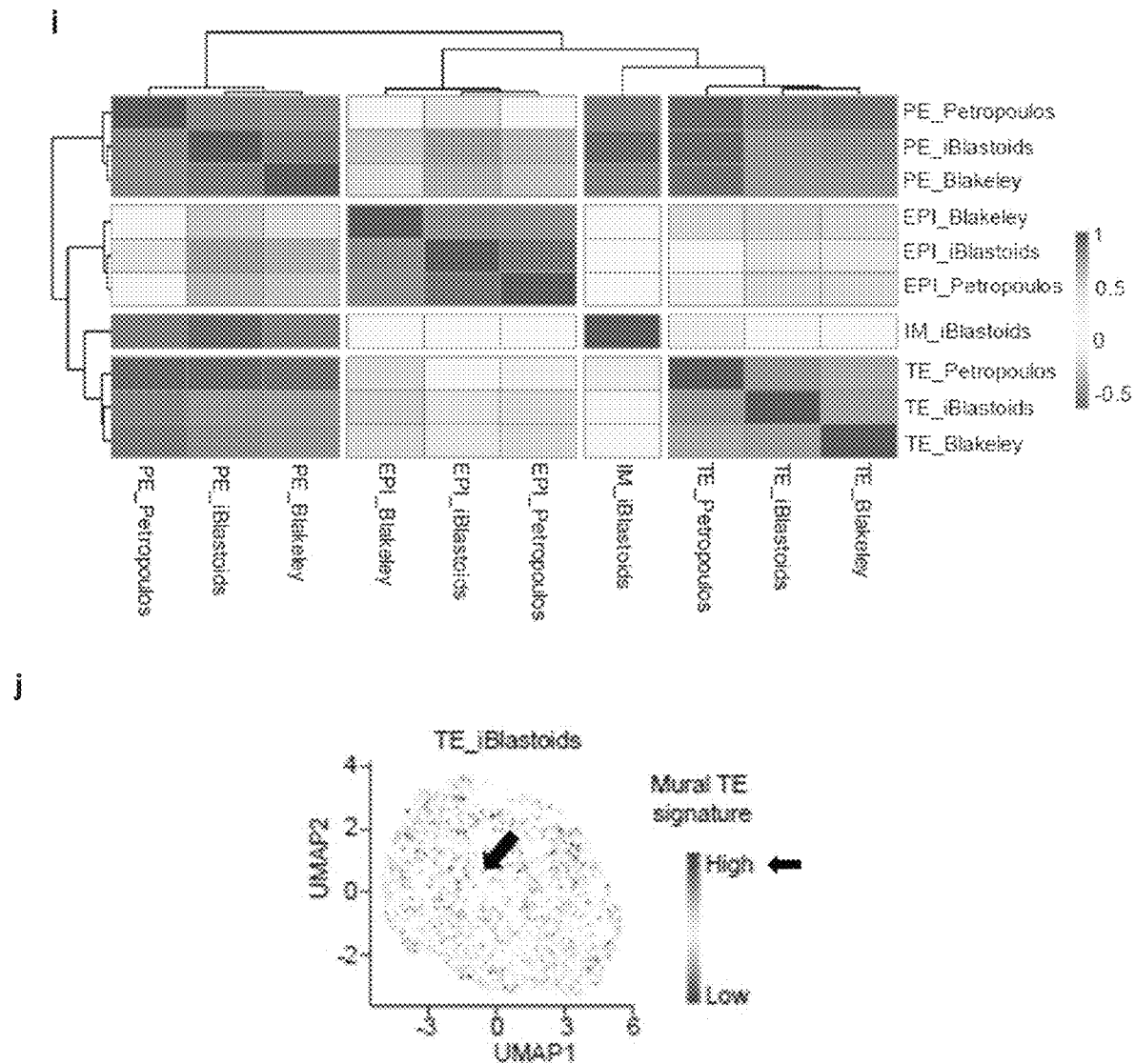
Figure 3:
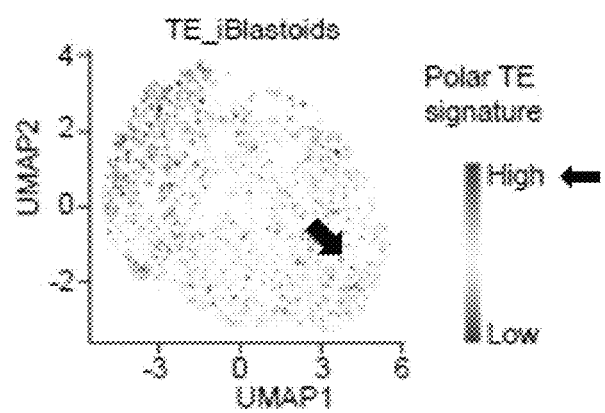
Figure 3:
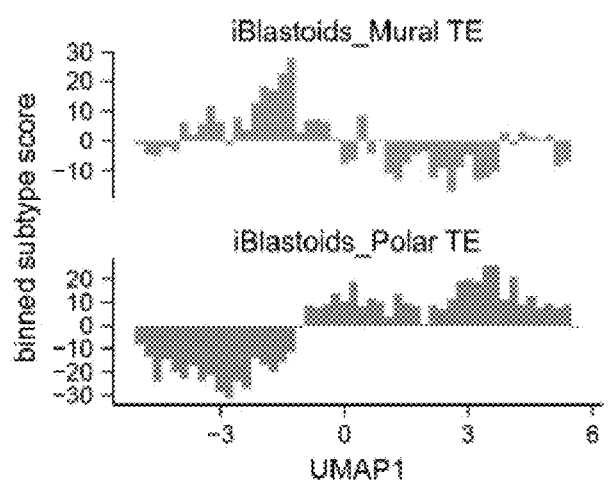
Figure 3:
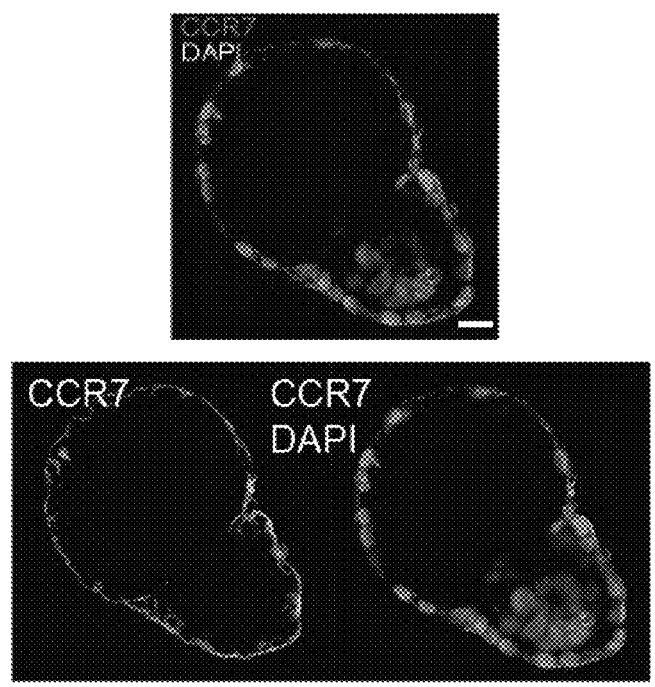
Figure 3:
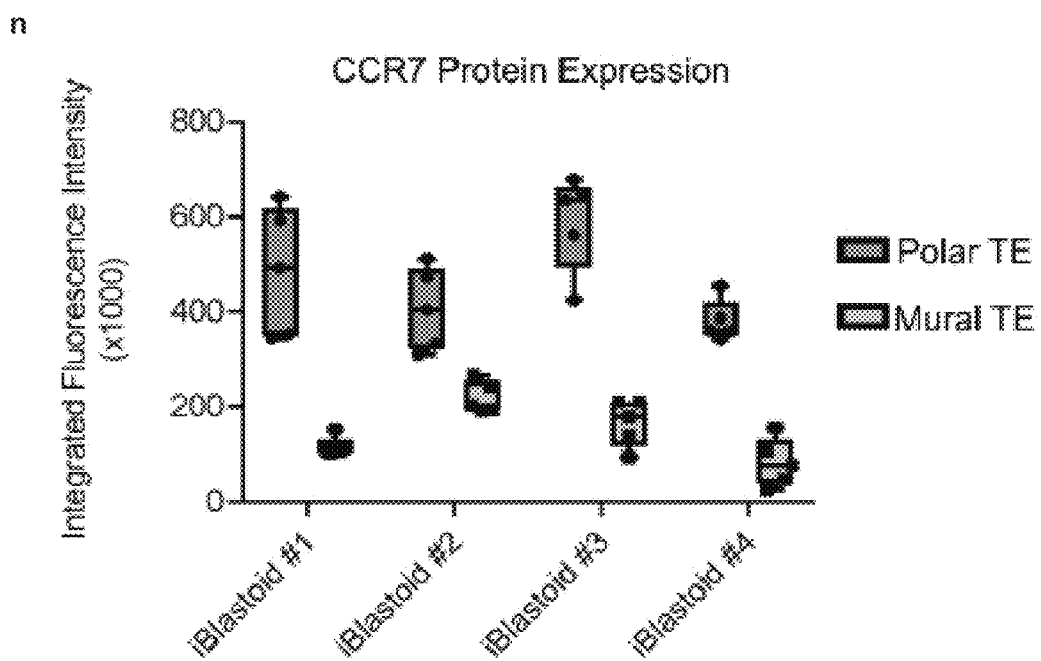
Figure 4A:
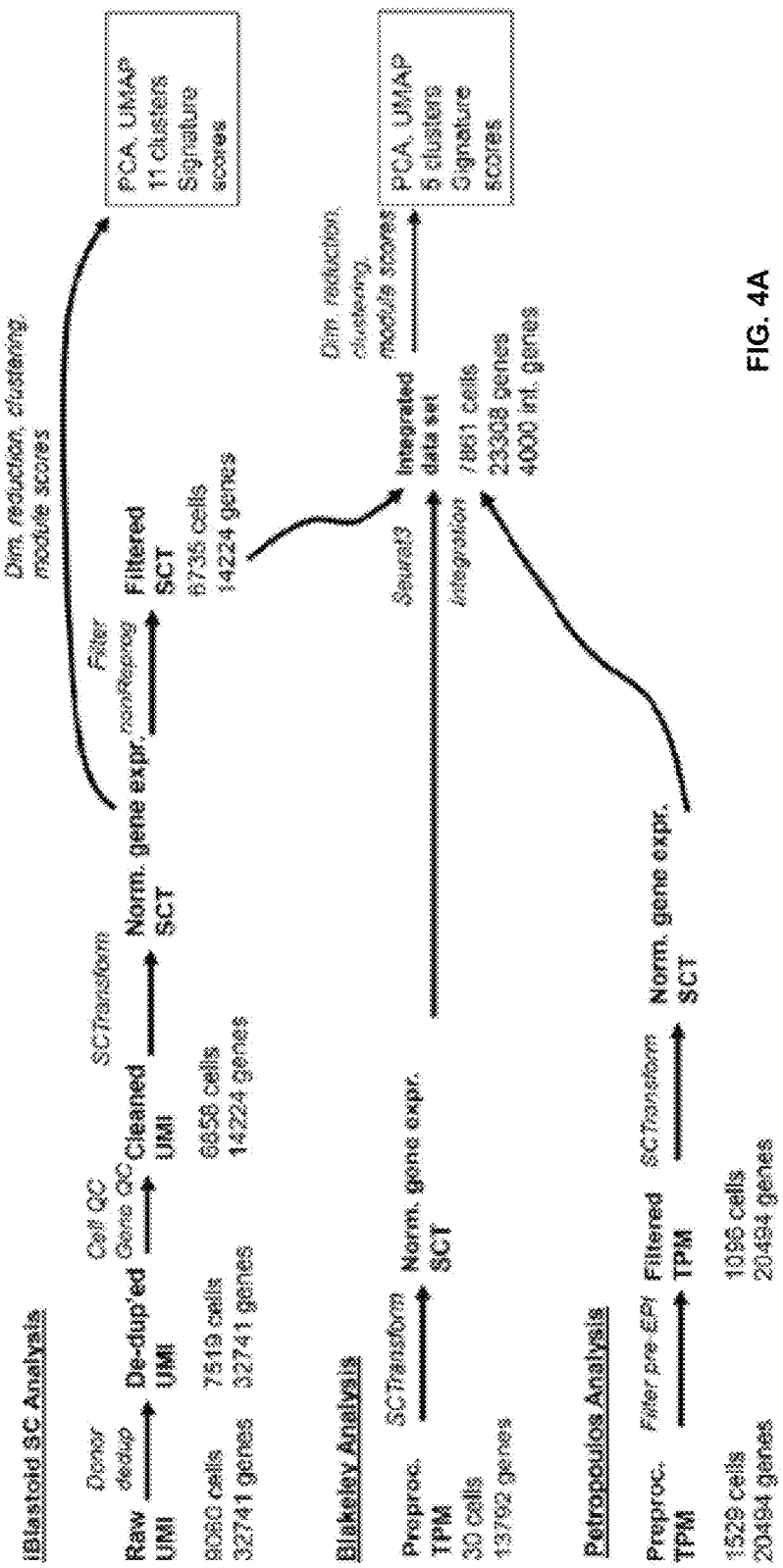

To further characterize the transcriptional makeup of the cells in the iBlastoids, the inventors performed single-cell RNA sequencing (scRNA-seq) using iBlastoids generated from two donors (FIG. 3a). After quality control and stringent filtering, 6858 cells were retained (3249 cells from Donor 1 and 3609 from Donor 2) and a total of 14224 genes were detected for downstream analyses (FIG. 4a). The Uniform Manifold Approximation and Projection (UMAP) analysis of the scRNA-seq data indicated that the cells distributed evenly without clustering based on donor or cell cycle differences (FIG. 4b, c). Although Sendai-KLF4 transcripts could be detected, there was minimal Sendai-KOS and Sendai-MYC expression in the scRNA-seq data (FIG. 4d), indicating that exogenous OCT4 and SOX2 were not expressed, or expressed at very low levels.

Figure 4E:
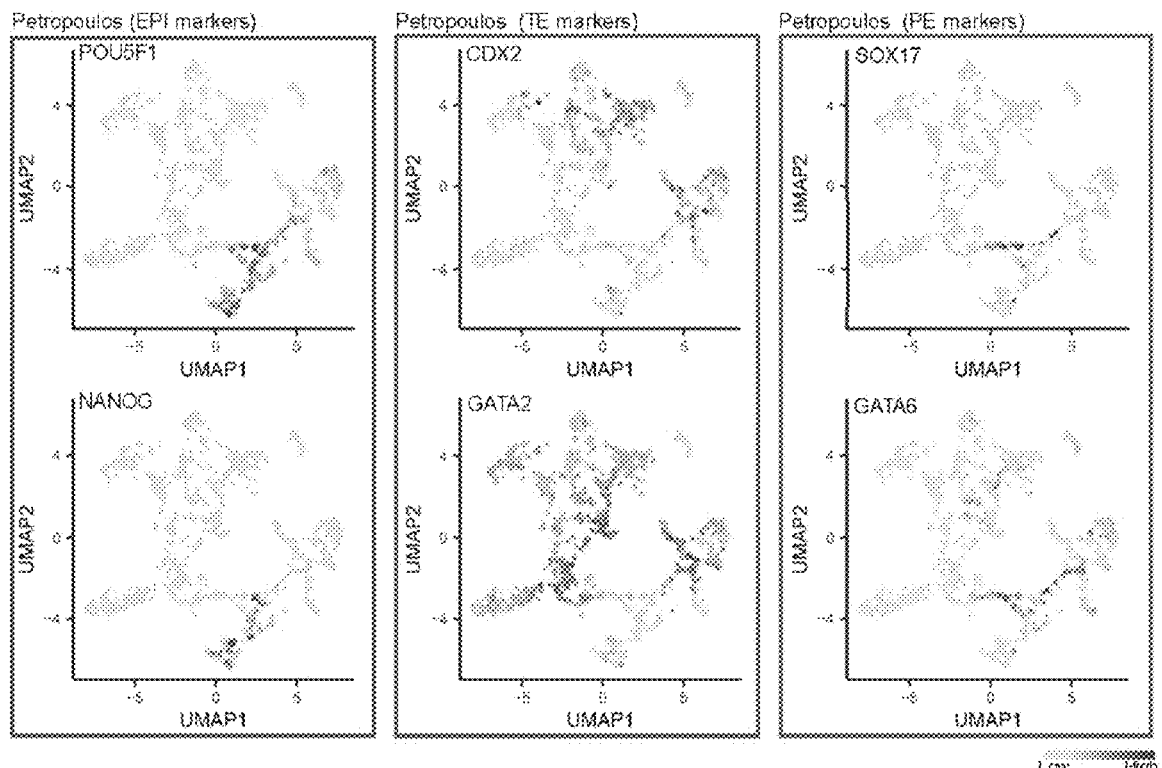

To identify the putative EPI, TE, and PE cell clusters on the UMAP, the inventors examined the expression of EPI markers (NANOG and OCT4/POU5F1), TE markers (CDX2 and GATA2), and PE markers (SOX17 and GATA6) in our scRNA-seq iBlastoids dataset. As shown in FIG. 3b, OCT4 and NANOG-expressing cells occupy a distinct region in the UMAP space. On this note, more cells express endogenous OCT4 than NANOG (see Methods), a feature that is observed in human blastocysts (FIG. 4e). SOX17 and GATA6-expressing cells were also found in a defined region on the UMAP while the inventors found a more heterogeneous expression of CDX2 and GATA2, which is similarly observed in the scRNA-seq dataset generated from E5-7 human blastocysts (FIG. 3b, FIG. 4e).

Figure 5:
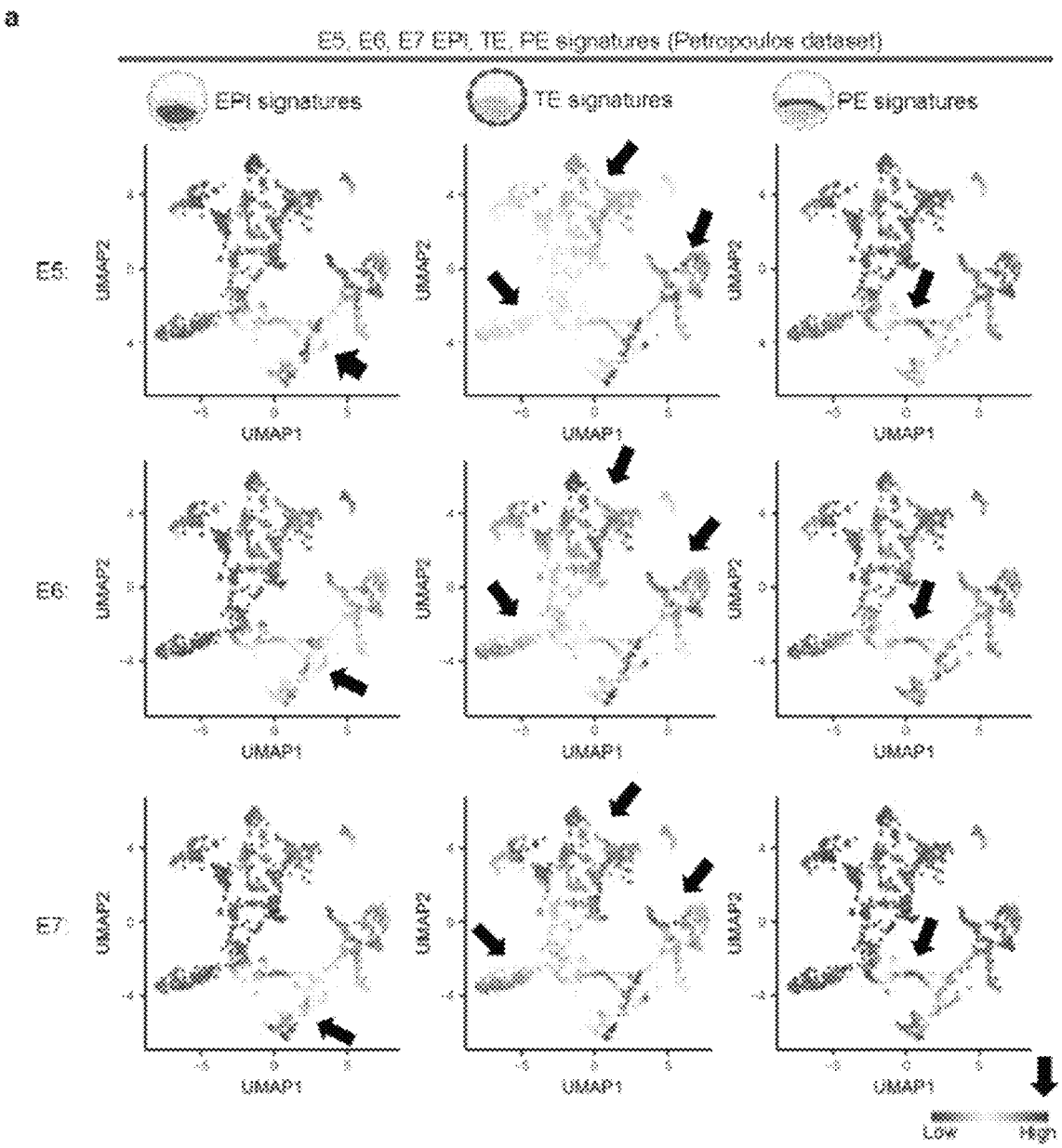
FIG. 5. Scoring of the defined E5-7 EPI, TE, and PE signatures on blastocysts and iBlastoids. *a*, Defined EPI, TE, and PE signatures for E5, E6, and E7 developmental day on Petropoulos scRNA-seq dataset (Petropoulos). *b*, Defined EPI, TE, and PE signatures for E5, E6, and E7 developmental day on iBlastoid scRNA-seq dataset.
Figure 5:
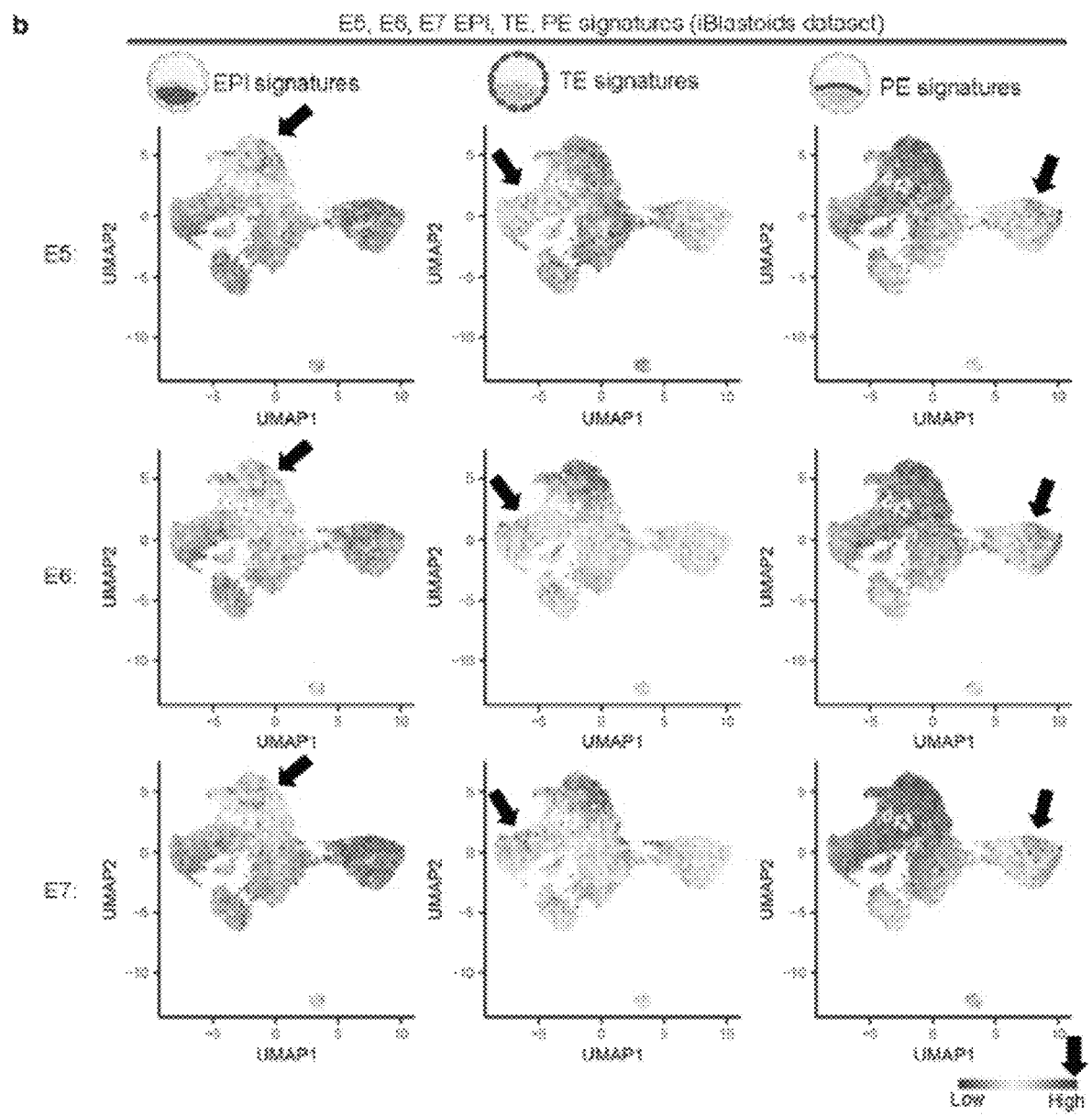

To further confirm cellular identity and the presence of EPI, TE, and PE lineages in the iBlastoids, the inventors applied a scoring system based on a set of EPI, TE, and PE specific gene signatures defined in Petropoulos Supra, using their scRNA-seq of E5-7 human blastocysts (FIG. 3c). Using these defined signatures, the inventors resolved distinct EPI, TE, and PE cell populations on the UMAP of the iBlastoid dataset. Further examination of the defined EPI, TE, and PE signatures separated by E5, E6, and E7 on the iBlastoids and blastocysts scRNA-seq datasets show negligible differences (FIG. 5a-b). Altogether, the results confirm the presence of EPI, TE, and PE-like cells in the iBlastoids.

Example 7—iBlastoids are Transcriptionally Similar to Blastocysts

Figure 4F:
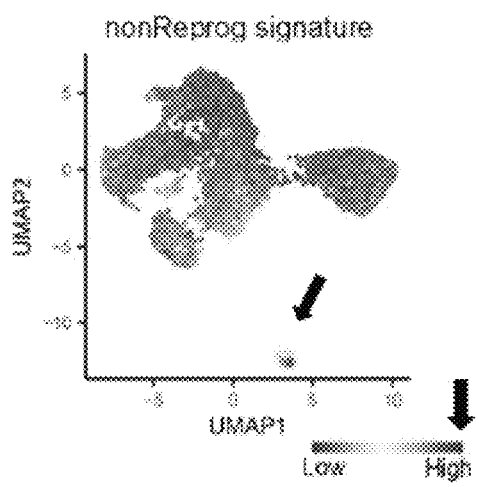
Figure 4G:
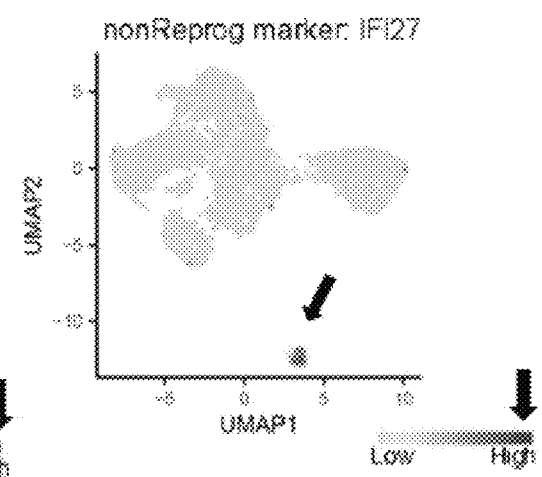
Figure 6:
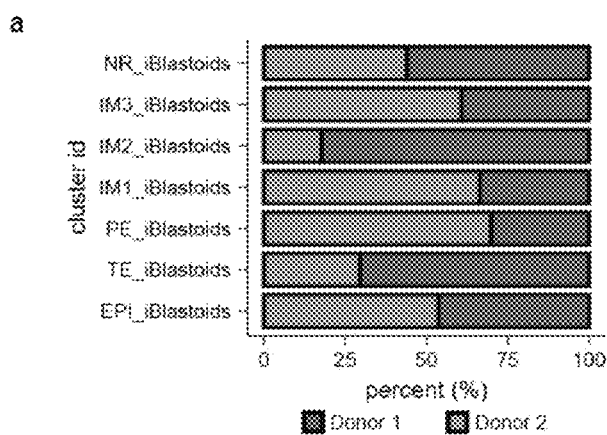
FIG. 6. scRNA-seq analysis of iBlastoids and blastocysts datasets. *a*, Proportion of cells from each donor across all assigned clusters. *b*, Heatmap showing gene expression profiles of each assigned cluster (top 10 genes each) in the iBlastoid scRNA-seq dataset. *c*, UMAP projection showing cell distribution of iBlastoid and blastocysts (Blakeley and Petropoulos) in the integrated dataset. *d*, Expression of EPI markers (POU5F1 and NANOG), TE markers (CDX2 and GATA2), and PE markers (SOX17 and GATA6) for the integrated dataset of iBlastoids and E5-7 blastocysts (Blakeley and Petropoulos). *e*, Pearson correlation analysis of iBlastoid EPI, TE, and PE clusters with annotated EPI, TE, and PE clusters from blastocysts (Blakeley and Petropoulos).
Figure 6:
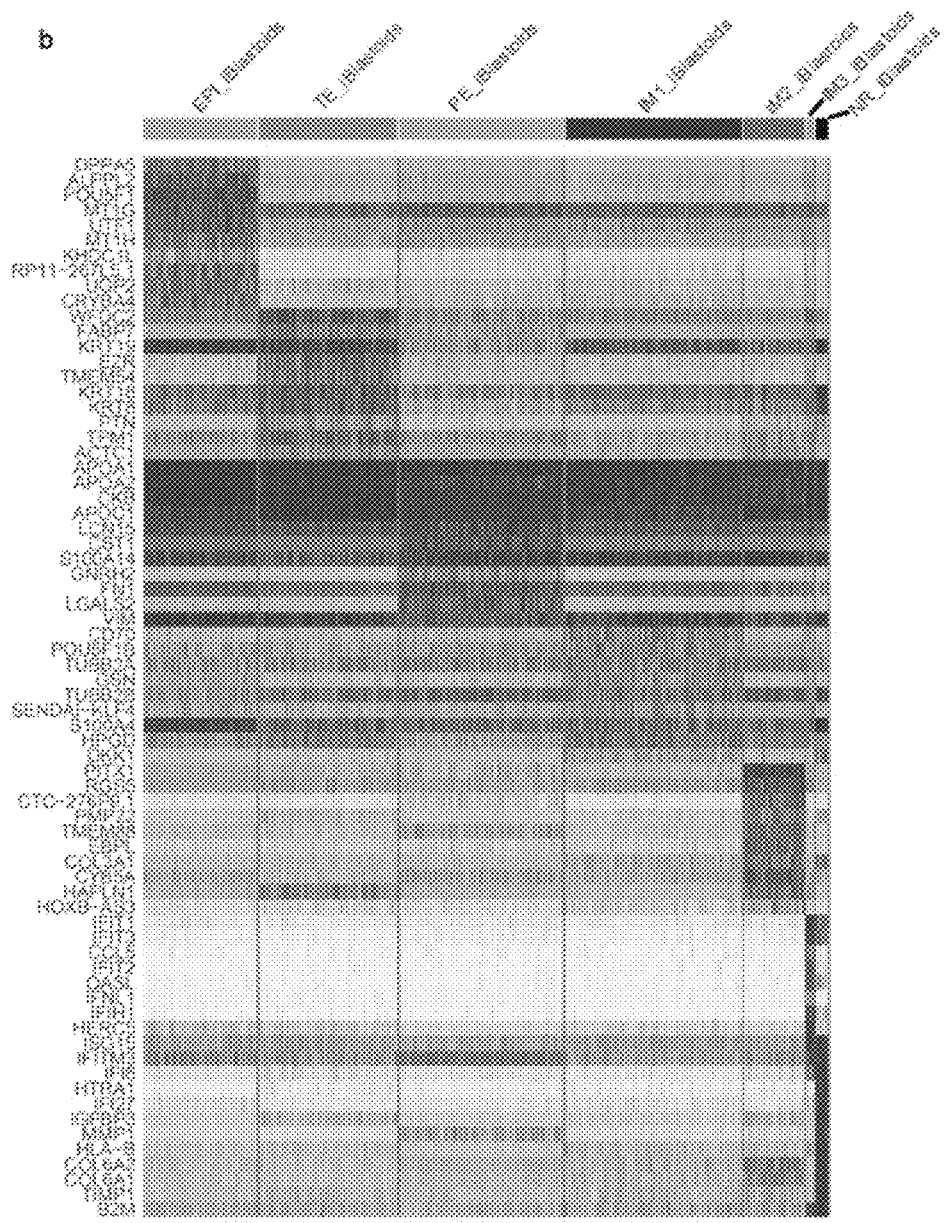
Figure 6:
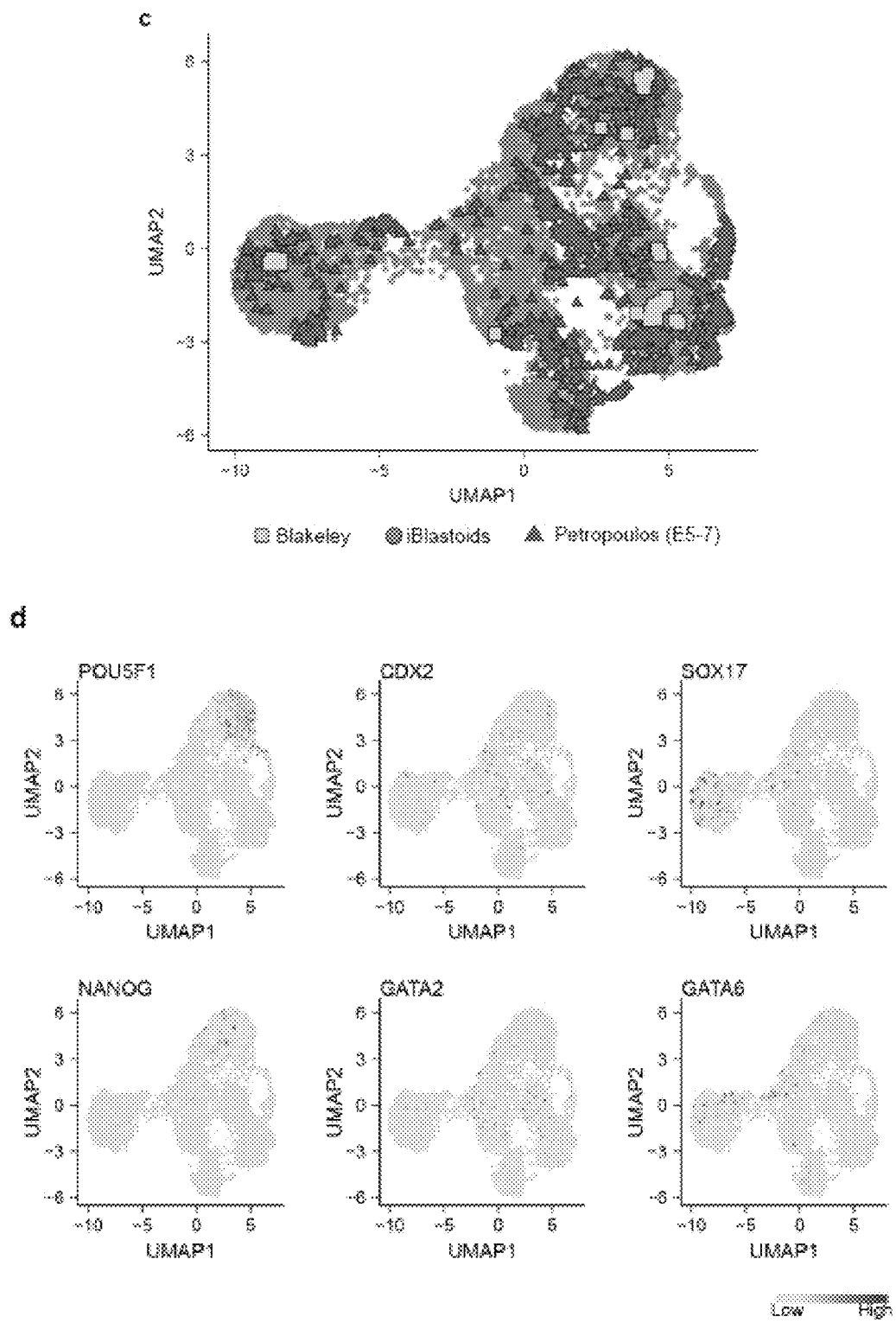
Figure 6:
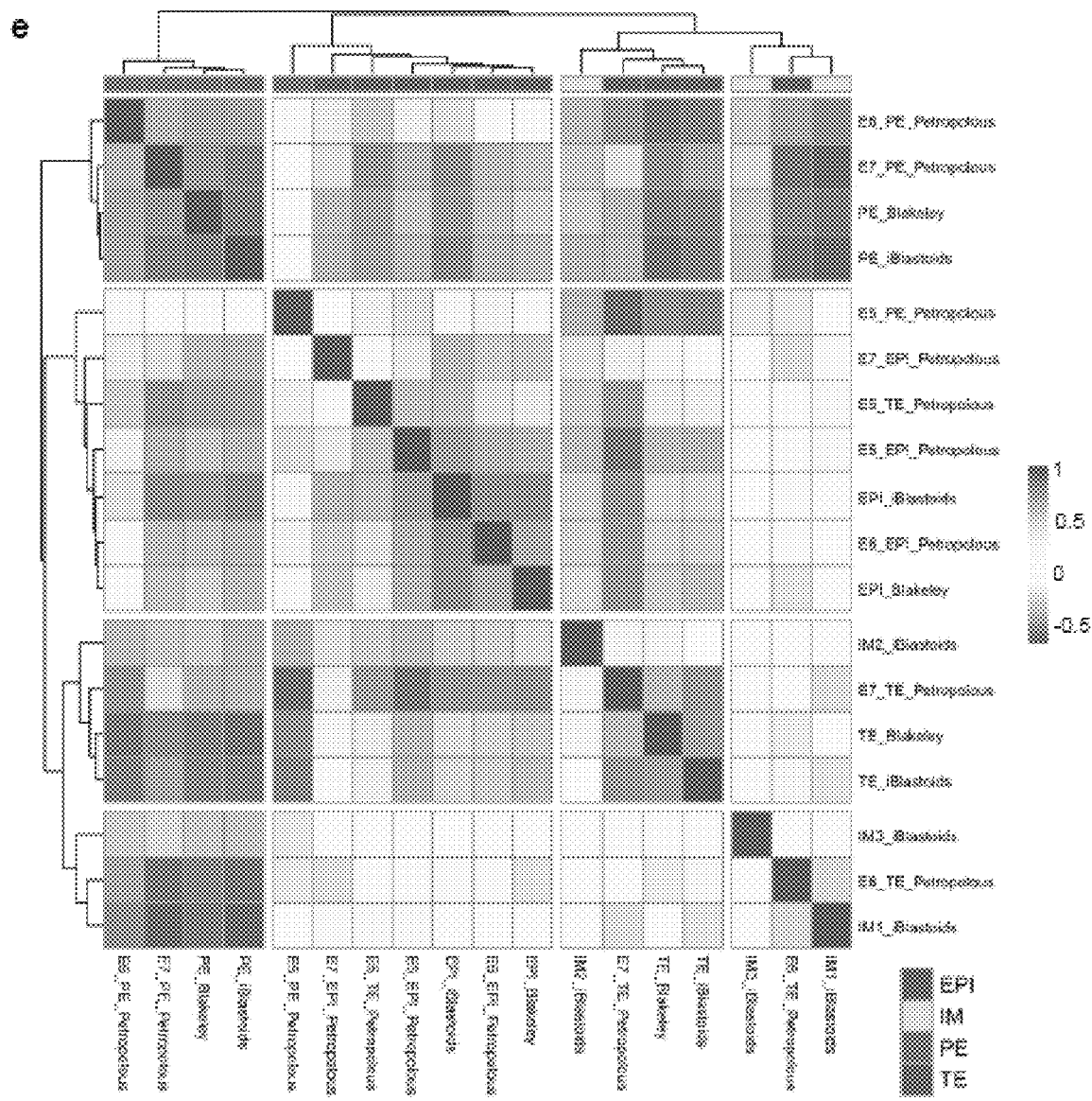

To further resolve the identity of the cells within the iBlastoids, the inventors performed unsupervised clustering analysis, identifying 7 cell clusters (FIG. 3d). Based on the EPI, TE, and PE gene signatures the clusters were assigned as: EPI cluster, TE cluster, or PE cluster. Three remaining clusters did not have a clear identity apriori and seem to have an intermediate signature (Clusters IM1-3) (FIG. 6a-b, FIG. 3d). These remaining clusters are examples of cells with mixed transcriptional signatures. Interestingly, cluster IM1 expresses a high level of CDX2 as well as exogenous KLF4 (FIG. 3b, FIG. 4d), which may suggest that those cells are en route to become TE-like cells. Similarly, mouse blastoids generated from EPSCs have cell clusters with an intermediate or undefined signature as revealed by scRNA-seq transcriptome profiling. The inventors also observed a cluster of cells representing non-reprogrammed refractory fibroblasts cells (FIG. 4f, g). On this note, this small fibroblast cluster was excluded from downstream analysis.

TE cells of human blastocysts specify into polar and mural TE during embryogenesis. Examination of the polar and mural TE signatures, defined by Petropoulos et al, in the iBlastoids showed that iBlastoids have two distinct populations of TE cells, one expressing a higher polar TE-related signature and another expressing a mural TE signature (FIG. 3 j,k,l). Immunostaining analysis of the polar marker, CCR713 also suggested a higher expression at the polar side of the iBlastoids (FIG. 3m,n).

To determine how similar cells of the iBlastoids are to the cells of blastocysts generated following IVF, the inventors integrated the iBlastoids scRNA-seq with two additional scRNA-seq datasets obtained of human blastocysts reported previously by the groups of Lanner and Niakan. The dataset from the group of Lanner was generated using Smart-seq2 on triturated cells, with a subset of samples at E5-7 enriched for ICM cells via immunosurgery. For the dataset from the Niakan group, micromanipulation via laser biopsy was used to separate ICM and polar TE from blastocysts, and cDNA from isolated single cells was generated and sequenced. UMAP analyses revealed a high concordance between cells of the blastocysts and iBlastoids (FIG. 3e, f, FIG. 6c, d). Importantly, cells from the EPI-iBlastoids cluster, TE-iBlastoids cluster, and PE-iBlastoids cluster overlap with their EPI, PE, and TE counterparts from blastocysts (FIG. 3e). To further characterize these cell populations, unsupervised clustering was performed (FIG. 3g, h), confirming that PE, EPI, and TE-like cells from the iBlastoids share the same clusters as PE, EPI, and TE cells from blastocysts. On this note, the inventors also observed that some blastocyst TE cells clustered together with cells of the IM1-iBlastoids cluster (FIG. 3e). Furthermore, correlation analysis of the iBlastoids EPI, TE, and PE clusters with the annotated EPI, TE, and PE cells from E5-7 blastocysts revealed a high correlation (~0.9) between the iBlastoid clusters and their blastocyst counterparts (FIG. 3i). The inventors correlated the iBlastoid cell clusters with the EPI, TE, and PE cells from blastocysts at different developmental days (E5, E6, and E7) in the Petropoulos dataset, observing correlation of the iBlastoids clusters with the respective EPI/TE/PE lineages of E5-7 blastocyst stages (FIG. 6e). Hierarchical clustering analysis suggests a better correlation of the iBlastoid EPI cluster with the early blastocyst EPI (E5 and E6). Altogether, this data demonstrates that the cells of the iBlastoids faithfully recapitulate the transcriptional makeup of the three cell lineages present in human blastocysts at E5-6.

Example 8—iBlastoids can Model In Vitro Implantation

To evaluate whether iBlastoids could be used to model the morphological and molecular changes occurring during the peri-implantation and early post-implantation window of human embryonic development in the absence of a uterus, the inventors performed an in vitro attachment assay by modifying the human embryo attachment culture previously published using human blastocysts. Although there is currently no precedent to working with human blastoid models, all experiments were approved by the Institutional Human Research Ethics Committee, in concordance with published recommendations, as well as adhering to the International Consensus for culturing human embryos up to 14 days post-fertilization and/or formation of primitive streak (PS), whichever is first. Given that the "14-day rule" is not applicable to iBlastoids given the starting fibroblasts were derived from adult donors, the inventors focused on culturing the iBlastoids for the minimal time possible, in this case a maximum of 5 additional days (equivalent to ~E11), and terminating the experiments before morphological evidence of PS so as to remain well within international guidelines. To rule out molecular evidence of PS formation, the inventors performed a qRT-PCR 24 hr-time course of several key primitive streak markers during the 5-day embryo attachment culture and did not observe up-regulation of TBXT, EOMES, or MIXL1 or any morphological changes indicative of gastrulation (FIG. 8b). Therefore, with 5-days of iBlastoid attachment culture, the EPI compartment did not progress to the formation of a PS. Nevertheless, by stringently adhering to the above parameters, the inventors performed all subsequent human iBlastoid attachment culture experiments for a total of 4.5 days after iBlastoid formation.

Using the attachment culture model, most of the iBlastoids (>90%) attached within 24 hrs, increased in size, flattened and progressed to form an outgrowth, similar to what has been reported in human blastocysts (FIG. 7a). Following attachment, the number of NANOG and OCT4/SOX2 positive cells increased, indicating expansion of the iBlastoid EPI (FIG. 8c,d), similar to what has been observed when using human blastocysts. Moreover, CDX2 and GATA2 positive cells also spread upon attachment (FIG. 8c,d), which indicated TE outgrowth of the attached iBlastoids. Similar results were also obtained using iBlastoids generated from two additional donors (not shown). Next, the inventors examined the distribution of PE-like cells after attachment. Although many of them still co-stained with TE markers (GATA2 or CDX2), the inventors noticed some SOX17 and GATA6 positive cells localizing to the perimeter of the NANOG or OCT4 positive EPI (FIG. 7b,c, FIG. 8e,f).

It has previously been reported that upon in vitro attachment, EPI cells of human blastocysts polarized and formed a lumen known as the pro-amniotic cavity. F-actin, OCT4, and aPKC immunostaining, indicated a central lumen (marked by F-actin and aPKC) within the EPI compartment of ~20-30% attached iBlastoids surrounded by radially organized OCT4-positive cells (FIG. 7d). The inventors observed the polarization of EPI-like cells and the emergence of a pro-amniotic-like cavity at day 3 of attachment.

The inventors then investigated the possible cell fate transitions of the TE-lineage upon attachment. Remarkably, they found high intensity and filamentous keratin KRT7 (a pan-trophoblast marker) staining of the TE cells in the attached iBlastoids, in contrast to the dull and limited KRT7 staining in the iBlastoids before attachment culture (FIG. 7e). The results suggest a TE cellular state transition to the trophoblast lineage which was also reported when culturing human blastocysts. Importantly, the inventors observed that cells surrounding the EPI-like compartment in the attached iBlastoids had a greater nuclear volume compared to cells of EPI, which is indicative of trophoblast cells (FIG. 7f). Notably, the inventors found some cells that morphologically resembled syncytiotrophoblast (ST) and extravillous cytotrophoblasts (EVT), as demonstrated by the respective multi-nucleated phenotype and spindle-like morphology in the periphery of the attached iBlastoids (FIG. 7f).

To further validate the presence of ST and EVT-like cells, the inventors performed immunostaining using hCG as a ST marker, and MMP2 as an EVT marker (FIG. 7g). The inventors detected a strong and extensive staining for hCG, reflecting the early development of ST; whereas MMP2 was detected in a lower number of cells in agreement with the EVT developing later during the implantation stage (FIG. 7g). In addition, qRT-PCR analysis also revealed the upregulation of the ST marker CSH1 and EVT marker ITGA117 with attachment, indicating the iBlastoid TE cells can differentiate into ST and EVT-like states (FIG. 7h, FIG. 10).

Finally, the inventors performed hCG ELISA on the conditioned media collected from the attached iBlastoids, and detected a 10-fold increase in the amount of hCG 4.5 days after attachment (FIG. 7i). Altogether, the results show that iBlastoids can be used to model in vitro implantation similar to blastocysts, highlighting the fact that it is a valuable model system that enables the analysis of the peri-implantation and early post-implantation stages of embryonic development in humans.

Figure 7:
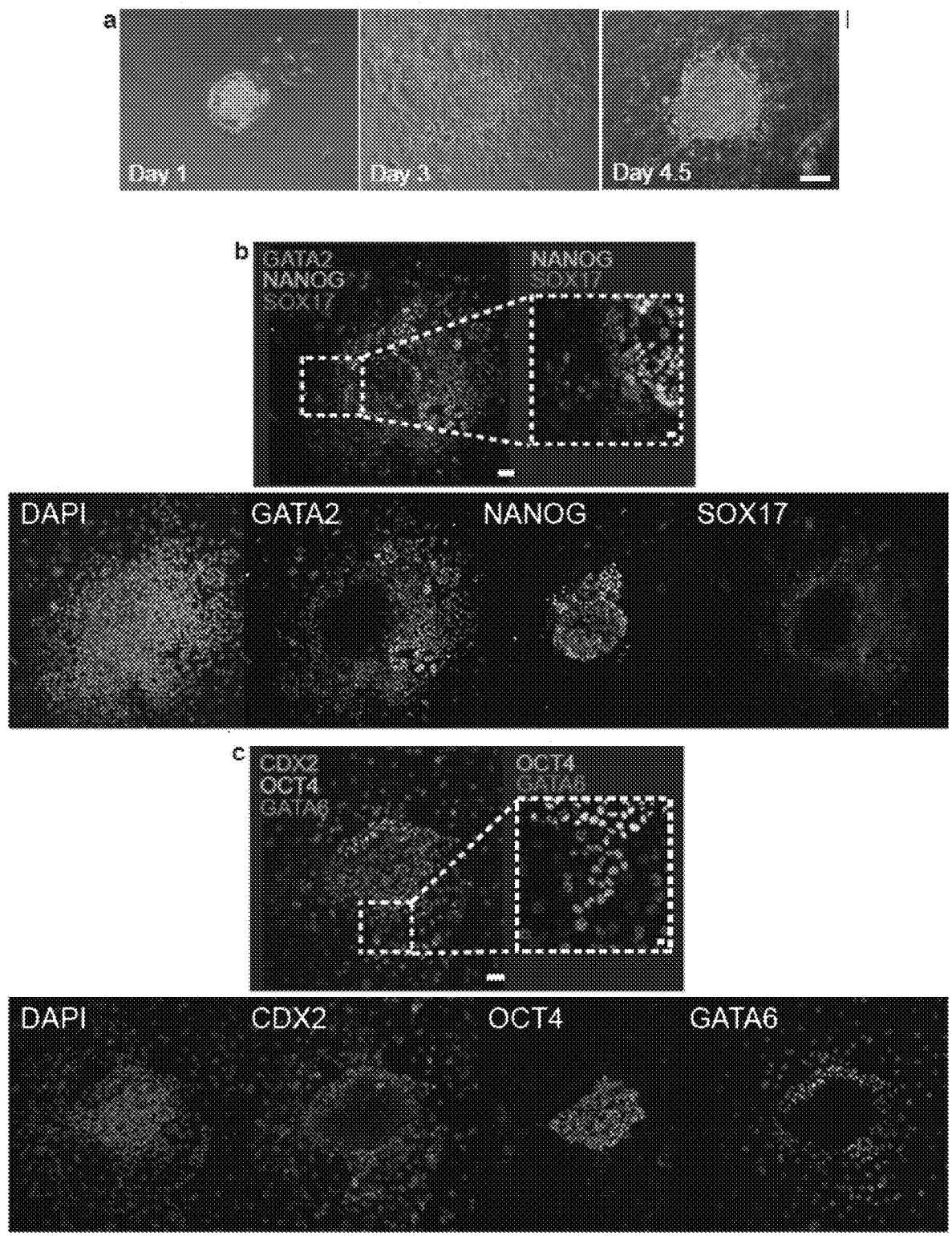
FIG. 7. Modeling human in vitro implantation using iBlastoids. *a*, Representative phase-contrast images of iBlastoid at day 1, 3, and 4.5 of attachment (n=5). Scale bar, 100 μm. *b*, GATA2, NANOG, and SOX17 co-staining, n=2. c, CDX2, OCT4, and GATA6 co-staining, n=2. *d*, F-actin, OCT4 and aPKC co-staining, with the pro-amniotic-like cavity indicated by arrowheads, n=2. *e*, KRT7 and NANOG co-staining, n=4. *f*, F-actin and NANOG co-staining, epiblast-like cells and putative STs, and EVTs are indicated, n=2. g, MMP2 and hCG co-staining, n=2. Scale bars, 50 μm; 10 μm for zoom-in. *h*, qRT-PCR analysis of ST and EVT marker in attached iBlastoids, mean±s.e.m, n=5. *i*, hCG protein level detected by hCG ELISA using conditioned media collected from attached iBlastoids, mean±s.e.m, n=4.
Figure 7:
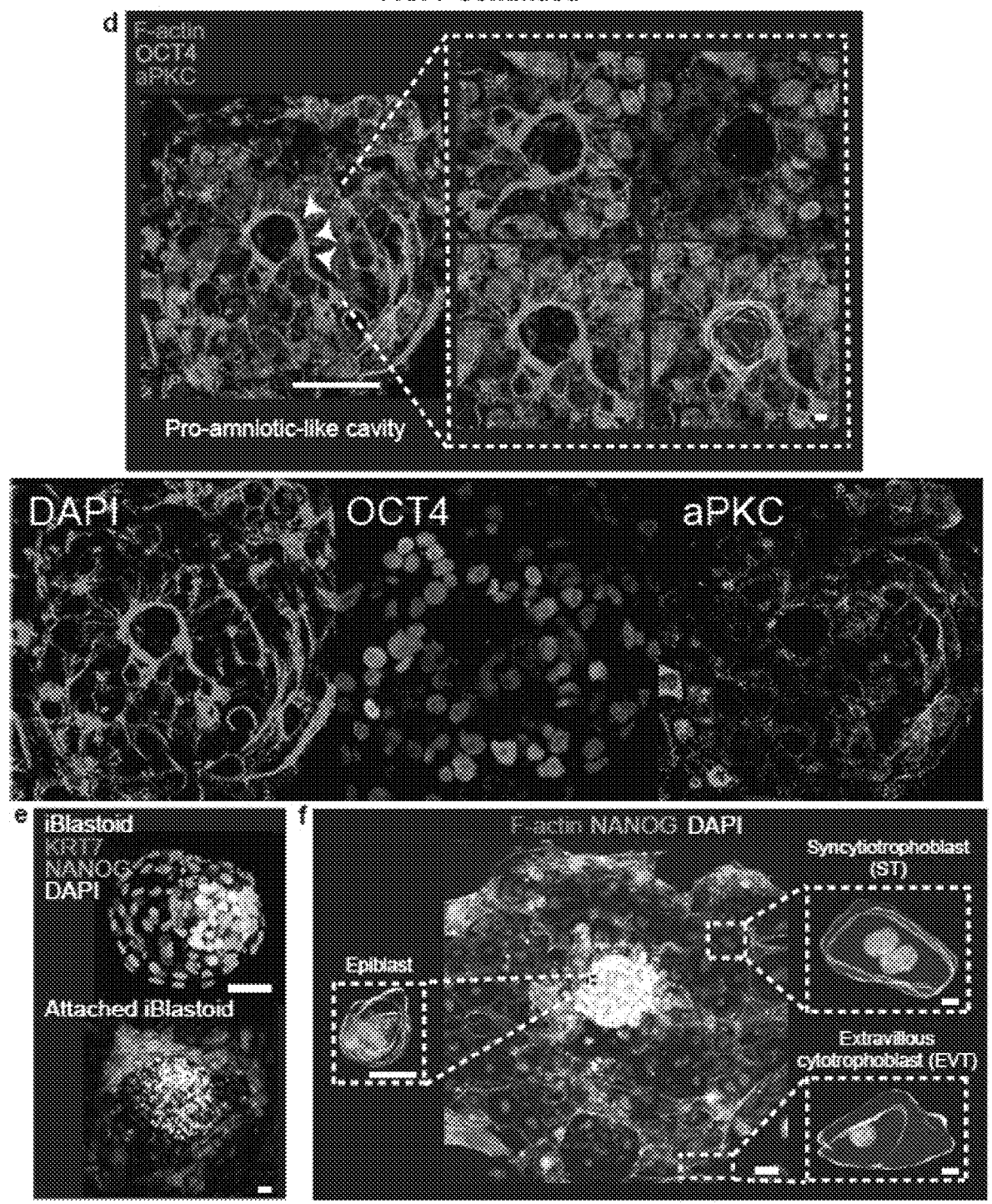
Figure 7:
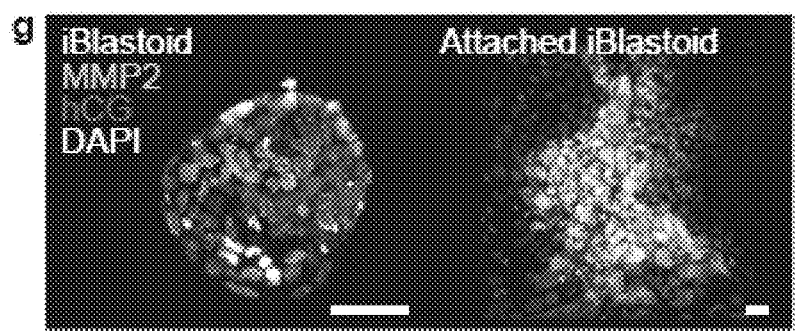
Figure 7:
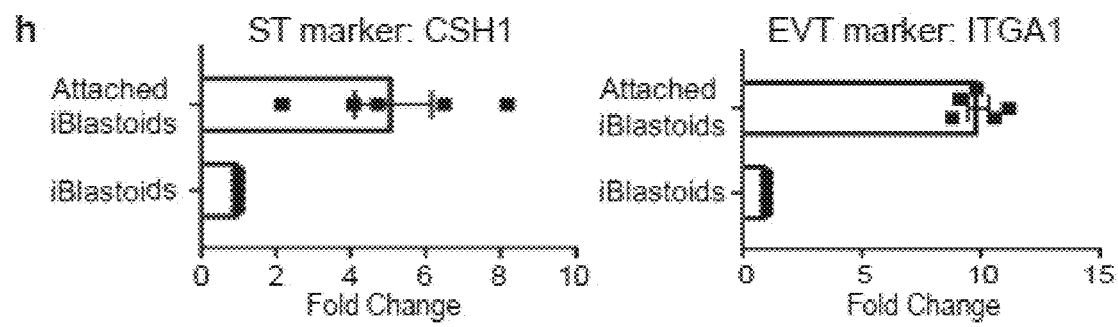
Figure 7:
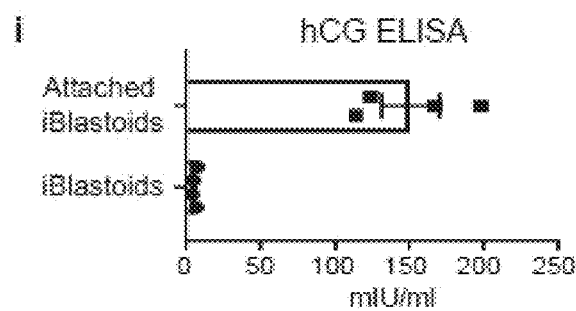

Here, the inventors present an in vitro model system for the human blastocyst. Unlike the approaches used to generate mouse blastoids, the inventors developed a strategy to generate human iBlastoids based on the reprogramming of fibroblasts directly into iBlastoids. Thus, this approach does not require the derivation and expansion of the three stem cell types present in human blastocysts prior to assembly. Since iBlastoids are generated from somatic cells, and not from stem cells from embryonic sources, the inventors anticipate that this will facilitate the wider acceptance of iBlastoids as a model, as iPSCs have done in the past. As shown herein, iBlastoids can faithfully recapitulate an integrated model of human blastocyst development including a TE and EPI-like layer, with cavitation, as well as recapitulating the spatial positioning of cell types within a human blastocyst (FIG. 1). Furthermore, iBlastoid cells are transcriptionally similar to cells of human blastocysts (FIGS. 3-6), and they can also be used to model in vitro some of the key functional characteristics of human blastocysts during the process of implantation (FIG. 7).

Based on the transcriptional analyses, EPI-like cells in the iBlastoids correspond to E5/E6 EPI cells from blastocysts, whereas the PE and TE-like cells correlate better with E7 stage. This could reflect some cellular heterogeneity across iBlastoids, or raises the possibility that the three lineages are not in complete synchrony in the iBlastoid model. Although the TE, EPI, and PE-like cells from the iBlastoids did not express the reprogramming factors, the inventors found clusters of cells in the iBlastoids (IM-1,2 clusters) still expressing the exogenous KLF4 gene. These cells also expressed CDX2 and GATA6 but did not present with strong overall TE or PE signatures, perhaps due to the co-expression of exogenous KLF4. However, the IM-1 cluster showed good correlation (~0.6) with E6-TE and therefore, unsurprisingly, several TE cells from the blastocyst occupy the same UMAP space. The data shows that iBlastoids represent an important accessible, scalable, and tractable model system with many applications in basic research and translational studies. For example, iBlastoids provide an in vitro platform to mimic the early cell fate transitions during embryogenesis. Furthermore, by re-establishing in vitro the critical embryonic-extraembryonic interface that regulates so many important events in normal early embryonic development, the inventors expect that iBlastoids could challenge the field to reinterpret and refine the existing knowledge and understanding of human pluripotency, as the coordinated interactions with the TE and PE has been mostly ignored to date. Given the fact that iBlastoids with specific genetic load can be generated, this will allow the studies of early developmental diseases such as Aneuploidy, Hydatidiform mole, Cornelia de Lange syndrome, and screening for treatments. iBlastoids could also serve as an excellent platform to develop genetic manipulation and gene editing techniques. In summary, iBlastoids represent a novel opportunity to model, in vitro, the pre-implantation blastocyst stage and the peri-implantation of human embryogenesis, and as such have tremendous potential for understanding infertility and early pregnancy loss.

Example 9—Co-Culture of iPSCs and iTSCs in a 3D Culture System

Figure 9:
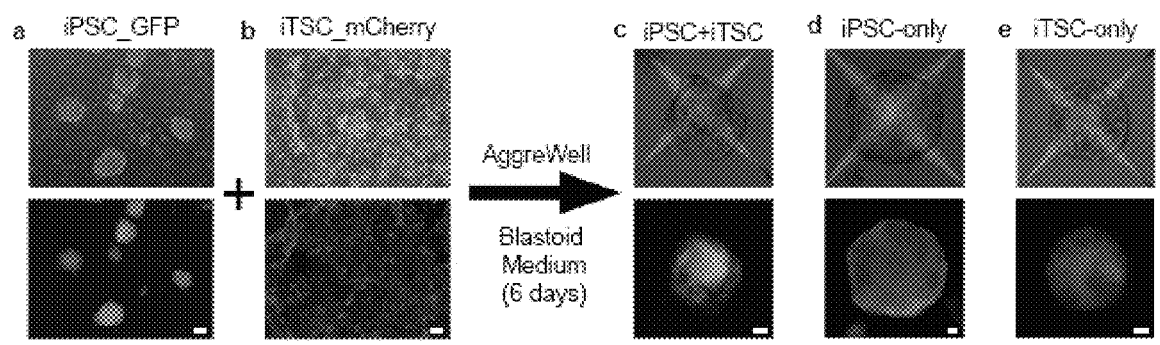
FIG. 9. (*a*) Naïve iPSCs with GFP reporter. Scale bar: 100 μm. (*b*): iTSCs with mCherry reporter. Scale bar: 100 μm. (*c*): Assembly of Naïve iPSCs and iTSCs. Scale bar: 20 μm. (*d*): Assembly of naïve iPSCs only. Scale bar: 20 μm. (*e*): Assembly of iTSCs only. Scale bar: 20 μm. (*f*): Immunostaining of Naïve iPSCs and iTSCs, naïve iPSCs only and iTSCs only assembled structures using pluripotency marker OCT4 and TSC marker KRT7. Scale bar: 20 μm. (*g*): Immunostaining of Naïve iPSCs only assembled structures using pluripotency marker NANOG and a TSC marker CDX2. Scale bar: 20 μm.
Figure 9:
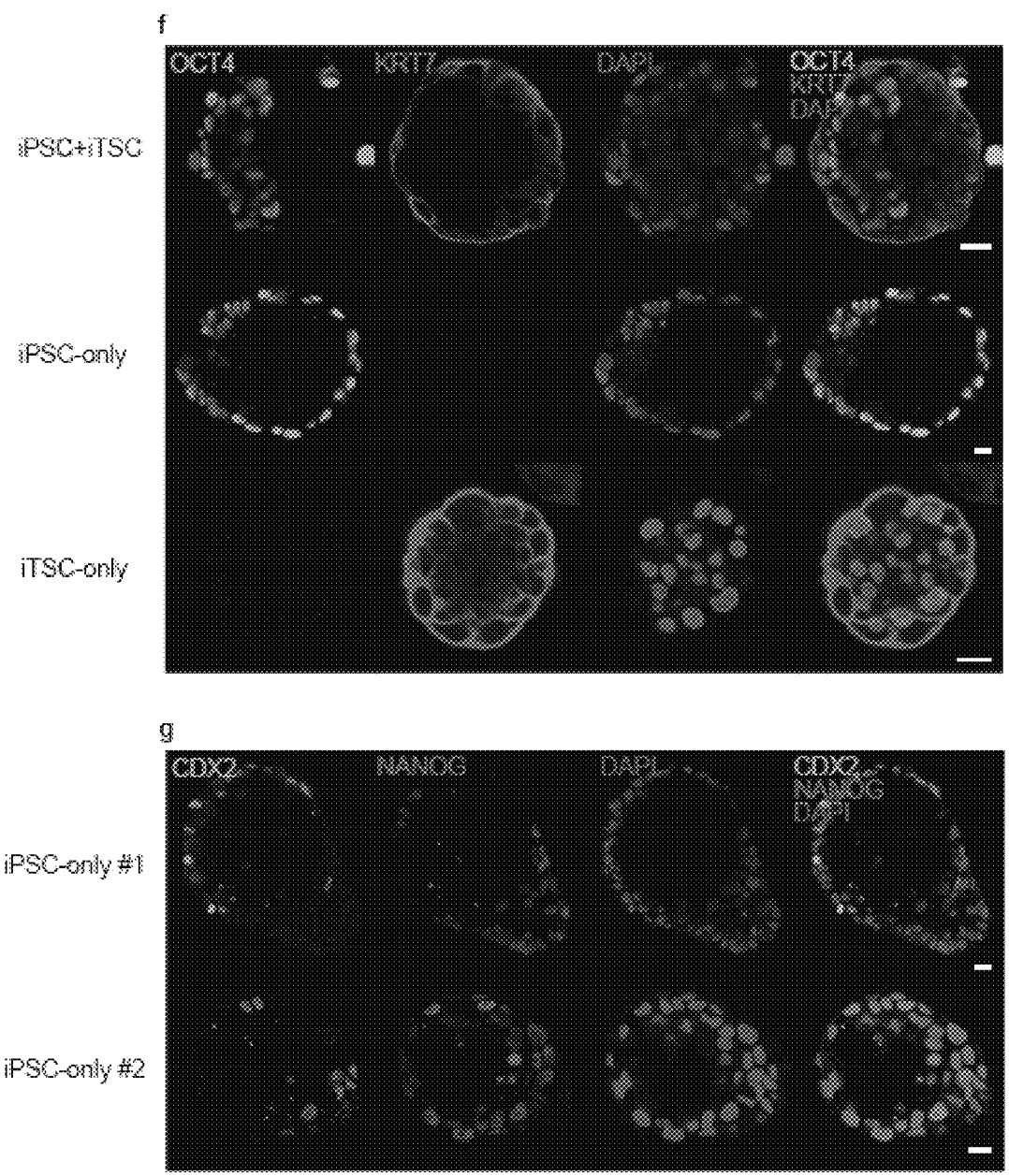

To facilitate the observation of assembly between iPSC and iTSC, iPSC line with GFP-reporter (iPSC-GFP) and iTSC line with mCherry-reporter (iTSC-mCherry) were first generated via lentiviral transduction of GFP and mCherry empty vector construct respectively (FIG. 9a,b). For the co-culture experiment, the dissociated cells were onto a 24-well AggreWell™400 plate in iBlastoid medium at different conditions: (1) iPSC and iTSC at respective 1:2.5 ratio with a total number of $1.2 \times 10^5$ cells per well (FIG. 9c); (2) iPSC-only with a total number of $1.2 \times 10^5$ cells per well (FIG. 9d); (3) iTSC-only with a total number of $1.2 \times 10^5$ cells per well (FIG. 9e). ROCKi were supplemented at the first day of co-culture to enhance cell survival and the cells were cultured for 6 days in the AggreWell™ system. 3D structures obtained at day 6 of formation were collected for downstream analysis (FIG. 9c-e).

Example 10—Use of Different Media to Generate Reprogramming Intermediates

To explore improvement of the proportion of EPI, TE and PE-like cells at day 21 of reprogramming, different signalling pathways/culture conditions that have been known to regulate the early embryonic and extraembryonic lineages cell fate were assessed. The inventors explored reprogramming in various culture media, such as those listed in Table 3a herein. Specifically, NACL medium was reported to promote PE-like cell fate; PA medium to promote TE-like cell fate; and t2iLGo medium to promote pre-implantation EPI-like cell fate. Based on the immunofluorescence analysis of day 21 reprogrammed cells (FIG. 11), NACL medium promotes expression of GATA6 (PE) and KLF17 (EPI); PA medium promotes upregulation of GATA3 (TE), GATA6 (PE) and KLF17 (EPI) while t2iLGo medium promotes upregulation of KLF17 (EPI). Among the conditions tested, PA medium gave rise to highest amount of TE, PE and EPI-like cells on day 21 reprogramming based on the 3 markers assessed.

Example 11—Reprogramming of Human Fibroblasts Via OKSMNL-mRNA Transfection

Reprogramming of human fibroblasts in this approach is mediated by OCT4, SOX2, KLF4, c-MYC, NANOG and LIN28, collectively known as OKSMNL. For somatic cell reprogramming via the mRNA approach, the experiments were performed according to the manufacturer's instructions of the StemRNA 3rd Gen Reprogramming Kit (StemGent, Cat #00-0076) with modifications. To perform the reprogramming, $1-2 \times 10^4$ human fibroblasts per well of a 12-well plate were seeded in fibroblast medium. After 24 hours (Day 0), cells were transfected with NM-RNA reprogramming transfection complex containing OSKMNL NM-RNA, EKB NM-RNA and NM-microRNAs generated with Opti-MEM (Gibco) and RNAiMAX (Invitrogen) according to manufacturer's instructions. 18 hours later media were renewed with fresh fibroblast medium and the next transfection is performed 6 hours later. The transfection process was repeated for another 3 days (for a 4× transfection regime) or 5 days (for a 6× transfection regime). The cells were cultured in fibroblast medium up to day 21 of reprogramming and were collected for further analysis. Further details of the media used in these experiments is provided in Example 2.

Figure 12:
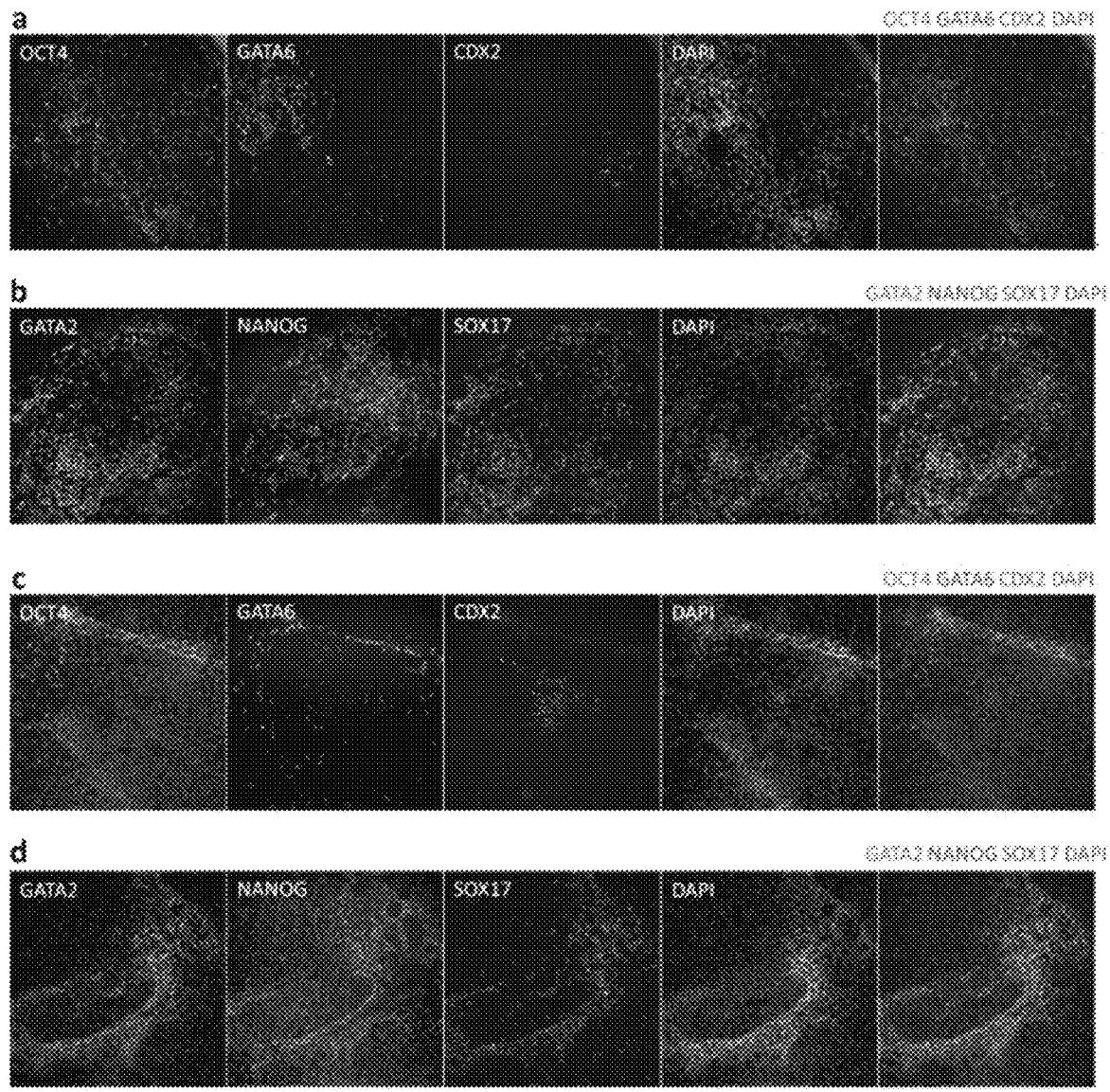
FIG. 12. Day 21 reprogrammed cells generated from human fibroblast via mRNA-mediated reprogramming. *a*, Immunostaining analysis of OCT4, GATA6 and CDX2 on day 21 reprogrammed cells generated from 4× OKSMNL mRNA transfection of human fibroblasts. *b*, Immunostaining analysis of GATA2, NANOG and SOX17 on day 21 reprogrammed cells generated from 4× OKSMNL mRNA transfection of human fibroblasts. c, Immunostaining analysis of OCT4, GATA6 and CDX2 on day 21 reprogrammed cells generated from 6× OKSMNL mRNA transfection of human fibroblasts. d, Immunostaining analysis of GATA2, NANOG and SOX17 on day 21 reprogrammed cells generated from 6× OKSMNL mRNA transfection of human fibroblasts.

On day 21, cells were immunostained to determine expression of OCT4, GATA6 and CDX2 (FIGS. 12a and c), GATA2, NANOG and SOX17 (FIGS. 12b and d), generated from 4× OKSMNL and 6× OKSMNL mRNA transfection.

The results demonstrate that reprogramming intermediates can be obtained from human fibroblasts when using alternative reprogramming methodologies, and have similar gene expression profiles of markers OCT4, GATA6, CDX2, GATA2, NANOG and SOX17 to those obtained as described in Example 3. These results indicate that reprogramming intermediates generated using alternative methodologies also exhibit epiblast (EPI), trophectoderm (TE) and/or primitive endoderm (PE) transcriptional signatures. These results indicate that iBlastoids could likely be derived from reprogramming intermediates obtained via different reprogramming methods, specifically different methods to drive expression of reprogramming transcription factors.

Example 12—Reprogramming of Human Mesenchymal Stem Cells (hMSCs) Via Sendai Virus-Mediated Reprogramming Reprogramming of hMSCs was conducted using Cyto-Tune-iPS 2.0 Sendai reprogramming kit according to the manufacturer's instructions (ThermoFisher, lot #2170052). The hMSCs were seeded at a density of $\sim 5-10 \times 10^4$ cells in MSC medium. After ~36 hours, the cells were transduced with Sendai viruses in FM at the multiplicity of infection (MOI) as follows, KOS MOI=5, c-MYC MOI=5, KLF4 MOI=6. Media replacement was done every other day starting from day 1 following transduction and every day from day 8 onwards. The reprogrammed cells were collected at day 21 of reprogramming for further analysis. Further details of the media used in these experiments is provided in Example 2.

Figure 13:
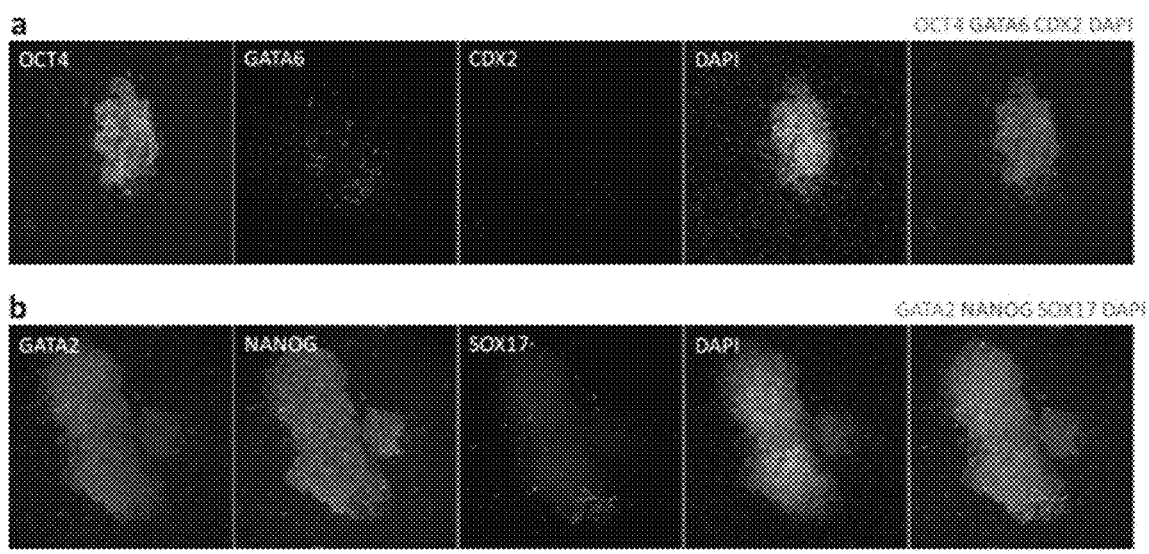
FIG. 13. Day 21 reprogrammed cells generated from human mesenchymal stem cells (hMSCs) via Sendai virus-mediated reprogramming. a, Immunostaining analysis of OCT4, GATA6 and CDX2 on day 21 reprogrammed cells generated from hMSCs. b, Immunostaining analysis of GATA2, NANOG and SOX17 on day 21 reprogrammed cells generated from hMSCs.

On day 21, cells were immunostained to determine expression of OCT4, GATA6 and CDX2 (FIG. 13a) or GATA2, NANOG and SOX17 (FIG. 13b).

The results demonstrate that reprogramming intermediates can be obtained from alternative somatic cells, in this case hMSCs, and have similar gene expression profiles of markers PCT4, GATA6, CDX2, GATA2, NANOG and SOX17 to those obtained as described in Example 3. These results indicate that reprogramming intermediates generated from alternative somatic cells also exhibit epiblast (EPI), trophectoderm (TE), and/or primitive endoderm (PE) transcriptional signatures. The results also indicate that iBlastoids could likely be derived from reprogramming intermediates obtained via different reprogramming methods, specifically different somatic cell types.

Example 13—Reprogramming of Human Peripheral Blood Mononuclear Cells (hPBMCs) Via Sendai Virus-Mediated Reprogramming Reprogramming of hPBMCs was conducted using Cyto-Tune-iPS 2.0 Sendai reprogramming kit according to the manufacturer's instructions (ThermoFisher, lot #2170052). To perform the reprogramming, $2.5-5 \times 10^5$ hPBMCs were counted and transferred into a 12-mL round-bottom tubes. The reprogramming mixture was prepared by adding calculated volumes of the Sendai viruses at the at the multiplicity of infection (MOI) as follows, KOS MOI=5, c-MYC MOI=5, KLF4 MOI=6 into 1 mL of PBMC medium.

After transferring the reprogramming mixture into the hPBMCs-containing round bottom tubes, the cells were centrifuged at 1000×g for 30 minutes at room temperature. Additional 1 mL of PBMC medium was added onto the centrifuged cells and the contents were resuspended and transferred onto 1 well of a 12-well plate for overnight incubation at 37° C. (Day 0). On the next day (Day 1), the medium was replaced with fresh PBMC medium. On Day 3 the cells were plated onto Matrigel-coated plates at a 1:3 ratio in fresh PBMC medium. On day 4 and day 6, medium replacement was performed by removing half of the spent medium and replace with fresh StemPro™34 medium (PBMC medium without cytokine). On day 8 of reprogramming, the cells were transitioned into either StemPro™34 medium or Stem™Pro34 medium supplemented with 10% FBS with medium replacement performed every other day from this point onwards. Cells were collected at Day 18 and Day 21 for further analysis. Further details of the media used in these experiments is provided in Example 2.

Figure 14:
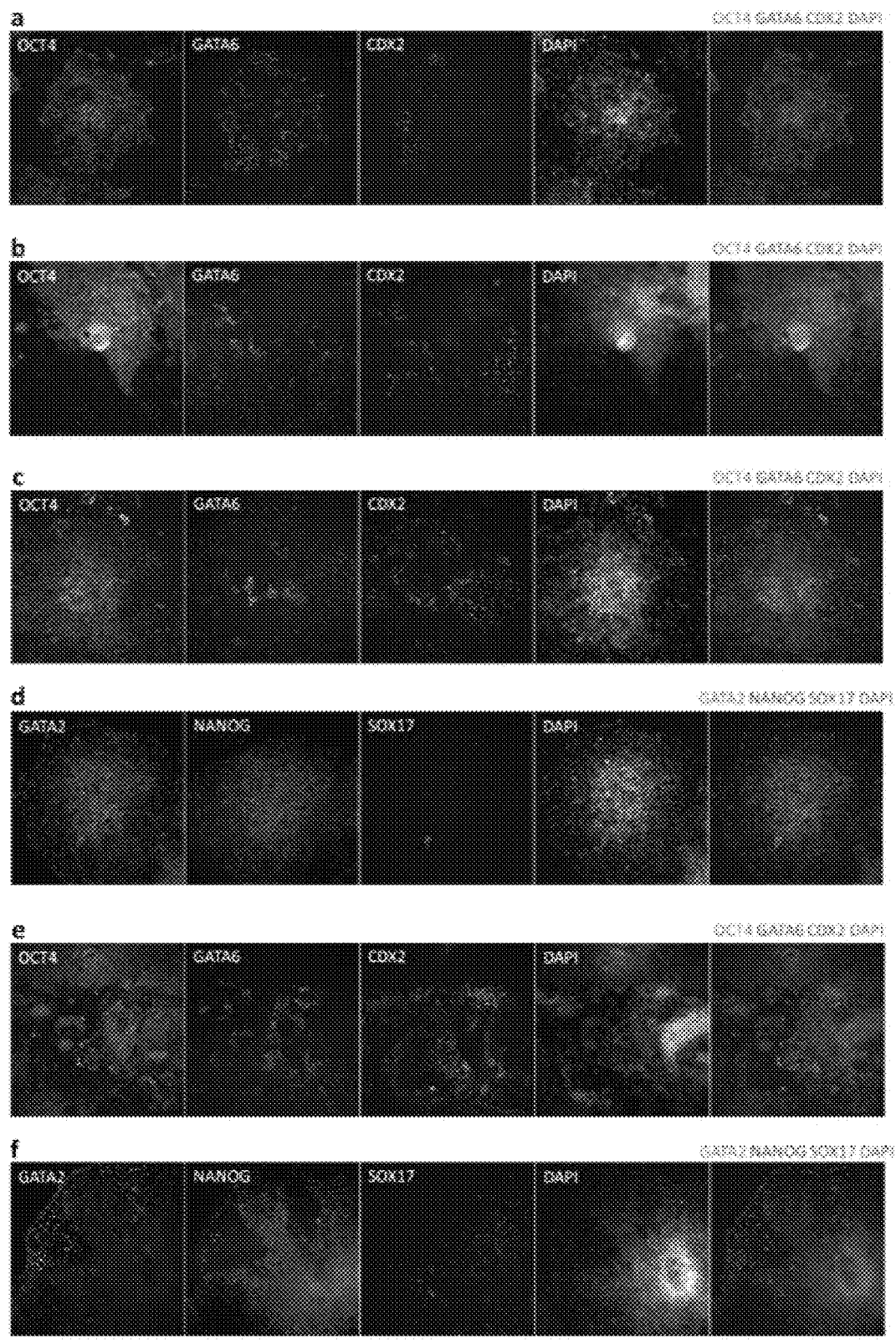
FIG. 14. Day 18 and day 21 reprogrammed cells generated from human peripheral blood mononuclear cells (hPBMCs) via Sendai virus-mediated reprogramming. a, Immunostaining analysis of OCT4, GATA6 and CDX2 on day 18 reprogrammed cells generated from hPBMCs in StemPro™34 medium. b, Immunostaining analysis of OCT4, GATA6 and CDX2 on day 21 reprogrammed cells generated from hPBMCs in StemPro™34 medium. c, Immunostaining analysis of OCT4, GATA6 and CDX2 on day 18 reprogrammed cells generated from hPBMCs in StemPro™34 medium supplemented with 10% FBS. d, Immunostaining analysis of GATA2, NANOG and SOX17 on day 18 reprogrammed cells generated from hPBMCs in StemPro™34 medium supplemented with 10% FBS. e, Immunostaining analysis of OCT4, GATA6 and CDX2 on day 21 reprogrammed cells generated from hPBMCs in StemPro™34 medium supplemented with 10% FBS. f, Immunostaining analysis of GATA2, NANOG and SOX17 on day 21 reprogrammed cells generated from hPBMCs in StemPro™34 medium supplemented with 10% FBS.

On days 18 and 21, cells were immunostained to determine expression of OCT4, GATA6 and CDX2 (FIG. 14a-c) or GATA2, NANOG and SOX17 (FIG. 14d-f).

The results demonstrate that reprogramming intermediates can be obtained from alternative somatic cells, in this case human peripheral blood mononuclear cells, and have similar gene expression profiles of markers OCT4, GATA6, CDX2, GATA2, NANOG and SOX17 to those obtained as described in Example 3. The results indicate that reprogramming intermediates generated from alternative somatic cells also exhibit epiblast (EPI), trophectoderm (TE), and/or primitive endoderm (PE) transcriptional signatures. These results also indicate that iBlastoids can likely be derived from reprogramming intermediates obtained via different reprogramming methods, specifically different somatic cells types.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method of producing a multi-layered cellular structure or blastocyst-like structure, the method comprising the following steps in order:
   a) increasing the protein expression or amount of one or more factors in a population of somatic cells, wherein the factors are for reprogramming the somatic cells towards a dedifferentiated or pluripotent state;
   b) culturing the cells for a sufficient time and under conditions to allow the reprogramming of the cells towards a dedifferentiated or pluripotent state to obtain a population of reprogramming intermediate cells;
   c) contacting the reprogramming intermediate cells with a culture medium comprising an activator of WNT pathway signalling selected from the group consisting of glycogen synthase kinase 3 (GSK-3↓ inhibitor), at least one transforming growth factor beta (TGF-β) inhibitor, a histone deacetylase (HDAC) inhibitor, epidermal growth factor (EGF), and bone morphogenic protein 4 (BMP4) under conditions that allow aggregation;
   d) culturing the cells in the culture medium for a sufficient time and under conditions that allow aggregation and/or allow the cells to exhibit at least one characteristic of a blastocyst-like structure,
   thereby producing a multi-layered cellular or blastocyst-like structure.

2. The method of claim 1, wherein the culture medium in step c) further comprises a Rho-kinase (ROCK) inhibitor.

3. The method of claim 1, wherein the protein expression, or amount, of the factors for reprogramming the somatic cells towards a pluripotent state, is increased by introducing at least one nucleic acid comprising a nucleotide sequence encoding at least one factor for reprogramming the somatic cells towards a pluripotent state, or encoding a functional fragment thereof, in the cell.

4. The method of claim 1, wherein the cell is cultured under the conditions of step b) for at least 1 day, or at least 2, 3, 4, 5, 6, 7, 8, 9, 10, 11, 12, 13, 14, 15, 16, 17, 18, 19, 20, 21, days or at least 22, at least 24, at least 28 or more days.

5. The method of claim 1, wherein the markers characteristic of the somatic cell are reduced prior to the step of culturing the reprogrammed somatic cells under conditions that allow aggregation to obtain a multi-layered cellular structure or blastocyst-like structure; or prior to the step of contacting the cells with a culture medium in step c).

6. A method of producing a multi-layered cellular structure or blastocyst-like structure, the method comprising the following steps in order:

a) increasing the protein expression or amount of one or more factors in a population of somatic cells, wherein the factors are for reprogramming the somatic cells towards a dedifferentiated or pluripotent state;
b) culturing the cells for a sufficient time and under conditions to allow the reprogramming of the cells towards a dedifferentiated or pluripotent state;
c) contacting the cells with a culture medium comprising an activator of WNT pathway signalling (selected from the group consisting of glycogen synthase kinase 3 (GSK-3) inhibitor), at least one transforming growth factor beta (TGF-β) inhibitor, a histone deacetylase (HDAC) inhibitor, epidermal growth factor (EGF), and bone morphogenic protein 4 (BMP4) under conditions that allow aggregation;
d) culturing the cells in the culture medium for a sufficient time and under conditions that allow aggregation and/or allow the cells to exhibit at least one characteristic of a blastocyst-like structure, wherein step b) comprises culturing the cells towards a dedifferentiated or pluripotent state in a medium that induces upregulation of the epiblast(EPI, trophectoderm (TE) and primitive endoderm (PE) lineage transcriptional signatures.

7. The method of claim 1, wherein the conditions that allow aggregation may comprise culturing on any culture plate, culture vessel or culture system that allows three-dimensional aggregation of cells.

8. The method of claim 1, wherein the multi-layered cellular structure or blastocyst-like structure comprises an inner cell layer and an outer cell layer, the inner cell layer comprises cells that exhibit one or more characteristics of cell of the epiblast (EPI) and/or the primitive endoderm (PE) lineage, and the outer cell layer comprises cells that exhibit one or more characteristics of a cell of the trophectoderm (TE).

9. The method of claim 1, wherein the multi-layered cellular structure or blastocyst-like structure comprises an inner cell layer wherein the inner cell layer further comprises a cluster of cells that exhibit one or more characteristics of the PE.

10. The method of claim 1, wherein the multi-layered cellular structure or blastocyst-like structure comprises an inner cell layer that comprises cells that exhibit one or more characteristics of cell of the epiblast (EPI) and/or the primitive endoderm (PE) lineage, wherein the characteristic of an EPI cell is presence of any one or more of the markers NANOG, OCT4 (also known as POU5F1) or SOX2.

11. The method of claim 1, wherein the multi-layered cellular structure or blastocyst-like structure comprises an outer cell layer that comprises cells that exhibit one or more characteristics of a cell of the trophectoderm (TE), wherein the characteristic of a TE cell is presence of one or more the markers CDX2 and GATA2 and/or a flattened or elongated epithelial morphology.

12. The method of claim 1, wherein the multi-layered cellular structure or blastocyst-like structure comprises an inner cell layer that comprises cells that exhibit one or more characteristics of cell of the epiblast (EPI) and/or the primitive endoderm (PE) lineage, wherein the characteristic of a PE cell is presence of the marker SOX17 or GATA6.

13. The method of claim 1, wherein the multi-layered cellular structure or blastocyst-like structure exhibits the main morphological features of human blastocysts at E5-7, preferably E6-7.

14. The method of claim 1, wherein the multi-layered cellular structure or blastocyst-like structure comprises a cell free cavity, or blastocoel-like cavity.

15. A method of producing a multi-layered cellular structure or blastocyst-like structure, the method comprising:
culturing an iPSC and iTSC cell under conditions that allow assembly and aggregation of the cells to obtain a multi-layered cellular structure, wherein the cells are cultured in culture medium for promoting cells to exhibit at least one characteristic of a blastocyst-like structure and wherein the culture medium comprises: an activator of WNT pathway signalling selected from the group consisting of glycogen synthase kinase 3 (GSK-3I inhibitor), at least one transforming growth factor beta (TGF-β) inhibitor, a histone deacetylase (HDAC) inhibitor, epidermal growth factor (EGF), and bone morphogenic protein 4 (BMP4);
thereby producing a multi-layered cellular or blastocyst-like structure.

16. The method of claim 15, wherein the iPSC and iTSCs are derived from human cells.

17. The method of claim 15, wherein the conditions allowing assembly and aggregation of the cells comprise co-culturing of the iPSCs and iTSCs in any culture vessel which promotes self-organisation and assembly of the cells.

18. The method of claim 6, wherein the culture medium in step c) further comprises a Rho-kinase (ROCK) inhibitor.

19. The method of claim 6, wherein the protein expression, or amount, of the factors for reprogramming the somatic cells towards a pluripotent state, is increased by introducing at least one nucleic acid comprising a nucleotide sequence encoding at least one factor for reprogramming the somatic cells towards a pluripotent state, or encoding a functional fragment thereof, in the cell.

20. The method of claim 6, wherein the cell is cultured under the conditions of step b) for at least 1 day, or at least 2, 3, 4, 5, 6, 7, 8, 9, 10, 11, 12, 13, 14, 15, 16, 17, 18, 19, 20, 21, days or at least 22, at least 24, at least 28 or more days.

21. The method of claim 6, wherein the conditions that allow aggregation comprise culturing on any culture plate, culture vessel or culture system that allows three-dimensional aggregation of cells.

22. The method of claim 15, wherein the culture medium comprises: a GSK-3 inhibitor in the form of CHIR99021, at least one TGF-β inhibitor selected from SB431542 and A83-01, a HDAC inhibitor in the form of valproic acid, EGF and BMP4.

23. The method of claim 15, wherein the medium further comprises a ROCK inhibitor.

24. The method of claim 22, wherein the medium further comprises a ROCK inhibitor in the form of Y-27632.

25. The method of claim 1, wherein the multi-layered cellular structure or blastocyst-like structure comprises an inner cell layer wherein the inner cell layer further comprises a cluster of cells that exhibit one or more characteristics of the PE and wherein the cells that exhibit one or more characteristics of the PE are, or are predominantly, peripheral to the cells that exhibit one or more characteristics of a cell of the epiblast.

26. The method of claim 15 wherein the iPSC and iTSCs are obtained by reprogramming of human somatic cells.

* * * * *

SEQUENCE LISTING

<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: hGAPDH Forward

<400> SEQUENCE: 1
ctgggctaca ctgagcacc                                                   19

<210> SEQ ID NO 2
<211> LENGTH: 21
<212> TYPE: DNA

```
<213> ORGANISM: Artificial Sequence
<220> FEATURE:
<223> OTHER INFORMATION: hGAPDH Reverse

<400> SEQUENCE: 2
aagtggtcgt tgagggcaat g                                      21

<210> SEQ ID NO 3
<211> LENGTH: 22
<212> TYPE: DNA
<213> ORGANISM: Artificial Sequence
<220> FEATURE:
<223> OTHER INFORMATION: CSH1 Forward

<400> SEQUENCE: 3
catgactccc agacctcctt ct                                     22

<210> SEQ ID NO 4
<211> LENGTH: 22
<212> TYPE: DNA
<213> ORGANISM: Artificial Sequence
<220> FEATURE:
<223> OTHER INFORMATION: CSH1 Reverse

<400> SEQUENCE: 4
atttctgttg cgtttcctcc at                                     22

<210> SEQ ID NO 5
<211> LENGTH: 21
<212> TYPE: DNA
<213> ORGANISM: Artificial Sequence
<220> FEATURE:
<223> OTHER INFORMATION: ITGA1 Forward

<400> SEQUENCE: 5
gctcctcact gttgttctac g                                      21

<210> SEQ ID NO 6
<211> LENGTH: 19
<212> TYPE: DNA
<213> ORGANISM: Artificial Sequence
<220> FEATURE:
<223> OTHER INFORMATION: ITGA1 Reverse

<400> SEQUENCE: 6
cgggccgctg aaagtcatt                                         19

<210> SEQ ID NO 7
<211> LENGTH: 23
<212> TYPE: DNA
<213> ORGANISM: Artificial Sequence
<220> FEATURE:
<223> OTHER INFORMATION: TBXT Forward

<400> SEQUENCE: 7
tatgagcctc gaatccacat agt                                    23

<210> SEQ ID NO 8
<211> LENGTH: 22
<212> TYPE: DNA
<213> ORGANISM: Artificial Sequence
<220> FEATURE:
<223> OTHER INFORMATION: TBXT Reverse

<400> SEQUENCE: 8
cctcgttctg ataagcagtc ac                                     22
```

```
<210> SEQ ID NO 9
<211> LENGTH: 19
<212> TYPE: DNA
<213> ORGANISM: Artificial Sequence
<220> FEATURE:
<223> OTHER INFORMATION: EOMES Forward

<400> SEQUENCE: 9
gtgcccacgt ctacctgtg                                              19

<210> SEQ ID NO 10
<211> LENGTH: 21
<212> TYPE: DNA
<213> ORGANISM: Artificial Sequence
<220> FEATURE:
<223> OTHER INFORMATION: EOMES Reverse

<400> SEQUENCE: 10
cctgccctgt ttcgtaatga t                                           21

<210> SEQ ID NO 11
<211> LENGTH: 20
<212> TYPE: DNA
<213> ORGANISM: Artificial Sequence
<220> FEATURE:
<223> OTHER INFORMATION: MIXL1 Forward

<400> SEQUENCE: 11
ggcgtcagag tgggaaatcc                                             20

<210> SEQ ID NO 12
<211> LENGTH: 21
<212> TYPE: DNA
<213> ORGANISM: Artificial Sequence
<220> FEATURE:
<223> OTHER INFORMATION: MIXL1 Reverse

<400> SEQUENCE: 12
ggcaggcagt tcacatctac c                                           21
```